(12) United States Patent
Reid et al.

(10) Patent No.: US 11,446,412 B2
(45) Date of Patent: *Sep. 20, 2022

(54) PATCH GRAFT COMPOSITIONS FOR CELL ENGRAFTMENT

(71) Applicant: The University of North Carolina at Chapel Hill, Chapel Hill, NC (US)

(72) Inventors: Lola M. Reid, Chapel Hill, NC (US); Wencheng Zhang, Chapel Hill, NC (US); Eliane Wauthier, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 491 days.

This patent is subject to a terminal disclaimer.

(21) Appl. No.: 16/006,496

(22) Filed: Jun. 12, 2018

(65) Prior Publication Data

US 2019/0015556 A1    Jan. 17, 2019

Related U.S. Application Data

(60) Provisional application No. 62/518,380, filed on Jun. 12, 2017, provisional application No. 62/664,694, filed on Apr. 30, 2018.

(51) Int. Cl.
| | |
|---|---|
| *A61L 27/38* | (2006.01) |
| *A61L 27/52* | (2006.01) |
| *A61L 27/58* | (2006.01) |
| *A61L 27/56* | (2006.01) |
| *A61L 27/36* | (2006.01) |
| *A61L 27/20* | (2006.01) |
| *A61L 27/26* | (2006.01) |
| *C12N 5/071* | (2010.01) |
| *C12N 5/0775* | (2010.01) |
| *A61L 27/22* | (2006.01) |

(52) U.S. Cl.
CPC .......... *A61L 27/3886* (2013.01); *A61L 27/20* (2013.01); *A61L 27/227* (2013.01); *A61L 27/26* (2013.01); *A61L 27/3604* (2013.01); *A61L 27/3641* (2013.01); *A61L 27/3813* (2013.01); *A61L 27/3834* (2013.01); *A61L 27/3839* (2013.01); *A61L 27/52* (2013.01); *A61L 27/56* (2013.01); *A61L 27/58* (2013.01); *C12N 5/067* (2013.01); *C12N 5/0662* (2013.01); *C12N 5/0668* (2013.01); *C12N 5/0676* (2013.01); *C12N 2506/1346* (2013.01)

(58) Field of Classification Search
CPC ...... A61L 27/3886; A61L 27/52; A61L 27/58; A61L 27/56; A61L 27/3839; A61L 27/3834; A61L 27/3813; A61L 27/3641; A61L 27/20; A61L 27/26; C12N 5/0668; C12N 5/0662; C12N 2506/1346
See application file for complete search history.

(56) References Cited

U.S. PATENT DOCUMENTS

| | | | |
|---|---|---|---|
| 4,683,195 A | 7/1987 | Mullis et al. | |
| 7,396,537 B1* | 7/2008 | Krupnick | A61K 47/34 424/400 |
| 9,272,073 B2* | 3/2016 | Ladet | A61L 27/52 |
| 9,447,381 B2 | 9/2016 | Gerecht et al. | |
| 2005/0048033 A1 | 3/2005 | Fraser | |
| 2007/0041952 A1* | 2/2007 | Guilak | A61L 27/3654 424/93.7 |
| 2008/0044900 A1 | 2/2008 | Mooney et al. | |
| 2008/0248005 A1 | 10/2008 | Phan | |
| 2008/0248570 A1 | 10/2008 | Turner et al. | |
| 2011/0081397 A1* | 4/2011 | Skalla | A61L 31/146 424/423 |
| 2011/0165219 A1* | 7/2011 | Barkai | A61L 27/3633 424/425 |
| 2011/0274666 A1 | 11/2011 | Turner et al. | |

(Continued)

FOREIGN PATENT DOCUMENTS

WO    WO 2007/070660 A2    6/2007

OTHER PUBLICATIONS

Ding et al., Diabetes, 58:1797-1806 (2009) (Year: 2009).*
Wang et al., Stem Cell, 31(9):1966-1979 (2013) (Year: 2013).*
Ayenehdeh et al., Immunol. Letters., 188:21-31 (2017) (Year: 2017).*
Coronel et al., Curr. Op. Biotechnol., 24:900-908 (2013) (Year: 2013).*
Davis et al., Biomater., 33:6691-6697 (2012) (Year: 2012).*
Figliuzzi et al., World J. Stem Cells, 6(2):163-172 (2014) (Year: 2014).*
Utech et al., J. Mater. Sci., 51:271-310 (2016) (Year: 2016).*
Office Action issued in co-pending U.S. Appl. No. 16/006,448, dated Mar. 27, 2020.

(Continued)

*Primary Examiner* — Kade Ariani
(74) *Attorney, Agent, or Firm* — Foley & Lardner LLP

(57) ABSTRACT

Compositions and methods of transplanting cells by grafting strategies into solid organs (especially internal organs) are provided. These methods and compositions can be used to repair diseased organs or to establish models of disease states in experimental hosts. The method involves attachment onto the surface of a tissue or organ, a patch graft, a "bandaid-like" covering, containing epithelial cells with supporting early lineage stage mesenchymal cells. The cells are incorporated into soft gel-forming biomaterials prepared under serum-free, defined conditions comprised of nutrients, lipids, vitamins, and regulatory signals that collectively support stemness of the donor cells. The graft is covered with a biodegradable, biocompatible, bioresorbable backing used to affix the graft to the target site. The cells in the graft migrate into and throughout the tissue such that within a couple of weeks they are uniformly dispersed within the recipient (host) tissue. The mechanisms by which engraftment and integration of donor cells into the organ or tissue involve multiple membrane-associated and secreted forms of MMPs.

26 Claims, 26 Drawing Sheets
(2 of 26 Drawing Sheet(s) Filed in Color)
Specification includes a Sequence Listing.

(56) References Cited

U.S. PATENT DOCUMENTS

| | | |
|---|---|---|
| 2012/0225814 A1 | 9/2012 | Hanjaya-Putra et al. |
| 2013/0197663 A1* | 8/2013 | MacEwan ............... A61F 2/105 623/23.72 |
| 2014/0301985 A1 | 10/2014 | Reid et al. |
| 2018/0078356 A1 | 3/2018 | Pekkan et al. |
| 2018/0361028 A1 | 12/2018 | Reid et al. |
| 2019/0151499 A1 | 5/2019 | Humayun et al. |

OTHER PUBLICATIONS

Karumbaiah, et al., Chondroitin Sulfate Glycosaminoglycan Hydrogels Create Endogenous Niches for Neural Stem Cells, Bioconjugate Chemistry, vol. 26, No. 12, pp. 2336-2349 (Dec. 2015).

Hayes, et al., "Chondroitin sulfate sulfation motifs as putative biomarkers for isolation of articular cartilage progenitor cells," J Histochem Cytochem., vol. 56, No. 2, pp. 125-138 (Feb. 2008).

Lozoya et al., "Regulation of Hepatic Stem/Progenitor Phenotype by Microenvironment Stiffness in Hydrogel Models of the Human Liver Stem Cell Niche," Biomaterials, vol. 32, No. 30, pp. 7389-7402 (2011).

Gattinoni, et al., "T memory stem cells in health and disease," Nature Medicine, vol. 23, No. 1, pp. 18-27 (Jan. 2017).

Trounson, et al., "Stem Cell Therapies in Clinical Trials: Progress and Challenges," Cell Stem Cell, vol. 17, pp. 11-22 (2015).

Sun, et al.. "Advances in skin grafting and treatment of cutaneous wounds," Science, vol. 346, pp. 941-945 (2014).

Lainas, et al., "Liver regeneration and recanalization time course following reversible portal vein embolization," J. Hepatology, vol. 49, pp. 354-362 (2008).

Lanzoni, et al., "Concise Review: Clinical Programs of Stem Cell Therapies for Liver and Pancreas," Stem Ceils 31, pp. 2047-2060 (2013).

Nevi, et al., "Hyaluronon coating improves liver engraftment of transplanted human biliary tree stem/progenitor cells," Stem Cell Research & Therapy 8, vol. 68, 14 pages (2017).

Turner, et al., "The future of cell transplant therapies: a need fortissue grafting," Transplantation vol. 90, pp. 807-810 (2010).

Kubota, et al., "Clonogenic hepatoblasts, common precursors for hepatocytic and biliary lineages, are lacking classical major histocompatibility complex class 1 antigen," vol. 97, No. 22, p. 12132-12137 (Jun. 2000).

Hindley, et al., "Organoids from adult liver and pancreas: Stem cell Biology and Biomedical Utility," Developmental Biology, vol. 420, pp. 251-261 (2016).

Rezanejad, et al., "Heterogeneity of SOX9 and HNF1β in Pancreatic Ducts Is Dynamic," Stem Cell Reports, vol. 10, No. 3, pp. 725-738 (2018).

Powell, et al., "Interactions of heparin/heparan sulfate with proteins: appraisal of structural factors and experimental approaches," Glycobiology, vol. 14, No. 4, p. 17R-30R (Apr. 2004).

Bo-Ra Son, et al., "Migration of Bone Marrow and Cord Blood Mesenchymal Stem Cells In Vitro Is Regulated by Stromal-Derived Factor-1-CXCR4 and Hepatocyte Growth Factor-c-met Axes and Involves Matrix Metalloproteinases," Stem Cells—Tissue-Specific Stem Cells, vol. 24, pp. 1254-1264 (2006).

"Corrected" International Search Report and Written Opinion issued in related International Patent Application No. PCT/US2018/036960, dated Nov. 19, 2018.

Carpino, et al., "Biliary Tree Stem/Progenitor Cells in Glands of Extrahepatic and Intraheptic Bile Ducts: An Anatomical in situ Study Yielding Evidence of Maturational Lineages," Journal of Anatomy, vol. 220, pp. 186-199 (2012).

International Search Report and Written Opinion issued in related International Patent Application No. PCT/US2018/036960, dated Oct. 25, 2018.

Office Action issued in co-pending U.S. Appl. No. 16/006,448, dated Sep. 30, 2019.

Non-Final Office Action issued in co-pending U.S. Appl. No. 16/006,464 dated Jun. 23, 2020.

Non-Final Office Action issued in co-pending U.S. Appl. No. 16/006,482 dated Jul. 10, 2020.

Non-Final Office Action issued in U.S. Appl. No. 16/006,504, dated Mar. 26, 2021.

Nagase et al., "Structure and Function of Matrix Metalloproteinases and TIMPs," Cardiovascular Research, vol. 69, pp. 562-573 (2006).

Almalki et al., "Effects of Matrix Metalloproteinases on the Fate of Mesenchymal Stem Celis," Almalki and Agrawal Stem Cell Research & Therapy, vol. 7, No. 129, 12 pages (2016).

Melamed, et al., "Modulation of Matrix Metalloproteinase-9 (MMP-9) Secretion in by Lymphopoiesis," International Immunology, vol. 18, No. 9, pp. 1355-1362 (Jul. 2016).

Parks, et al., "Matrix Metalloproteinases as Modulators of Inflammation and Innate Immunity," Nature Reviews/Immunology, vol. 4, pp. 617-629 (Aug. 2004).

Ong, et al., "Complex Regulation of Neutrophil-Drived MMP-9 Secretion in Central Nervous System Tuberculosis," Journ. of Neuroinflammation, vol. 14, No. 31, 12, pages (2017).

Malik, et al., "Peptic Ulcer Disease," National Library of Medicine, NIH, Jan. 29, 2021, 8 pages.

Ranasinghe et al., "Crohn Disease," National Library of Medicine, NIH, Jun. 9, 2020, 7 pages.

Descoteaux-Friday, et al., "Chronic Diarrhea," National Library of Medicine, NIH, Nov. 17, 2020, 11 pages.

Final Office Action issued in U.S. Appl. No. 16/006,464, dated Jan. 27, 2021.

Final Office Action issued in U.S. Appl. No. 16/006,482, dated Feb. 2, 2021.

Ghosh et al., "Cell Adaptation to a Physiologically Relevant ECM Mimic with Different Viscoelastic Properties", Biomaterials, vol. 28, pp. 671-670 (2007).

Non-Final Office Action issued in U.S. Appl. No. 16/006,448, dated Feb. 1, 2021.

Non-Final Office Action issued in U.S. Appl. No. 16/006,460, dated Dec. 24, 2020.

Risbud et al., "Hydrogel-Coated Textile Scaffolds as Candidate in Liver Tissue Engineering: II. Evaluation of Spheroid Formation and Viability of Hepatocytes", J. Biomater, Sci Polymer Edn, vol. 14, No. 7, pp. 719-231, (2003).

De Laet et al., "Recommendations for the Management of Tyrosinaemia Type 1", Orphanet Journal of Rare Diseases, vol. 8, No. 8, 9 pages (2013).

Foreign Search Report on PCT PCT/US2020/034250 dated Oct. 15, 2020.

Notice of Allowance issued in co-pending U.S. Appl. No. 16/006,464, dated May 12, 2021.

Extended Search Report issued in European Patent Application No. 18817374.4, dated Mar. 16, 2021.

Office Action issued in co-pending U.S. Appl. No. 16/006,448, dated Aug. 10, 2021.

Office Action issued in co-pending U.S. Appl. No. 16/006,460, dated Aug. 27, 2021.

Office Action issued in co-pending Russian application No. 2020100063, dated Nov. 9, 2021.

Office Action issued in co-pending U.S. Appl. No. 16/006,504, dated Nov. 12, 2021.

International Preliminary Report on Patentability issued in PCT/US2020/034250, dated Dec. 2, 2021.

Office Action issued in co-pending U.S. Appl. No. 16/006,482, dated Oct. 8, 2021.

Office Action issued in co-pending U.S. Appl. No. 16/006,460, dated Jul. 1, 2022.

* cited by examiner

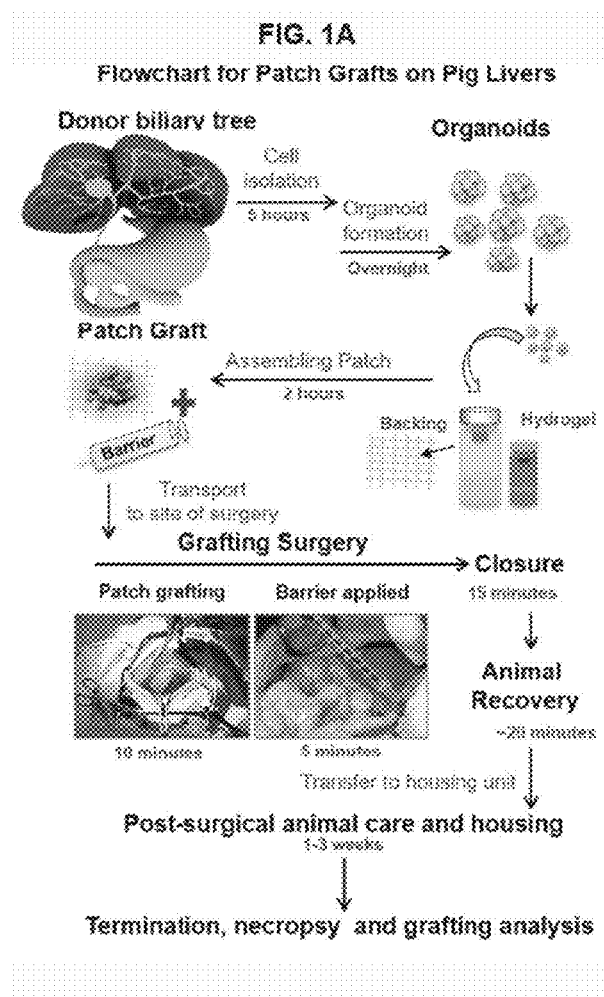
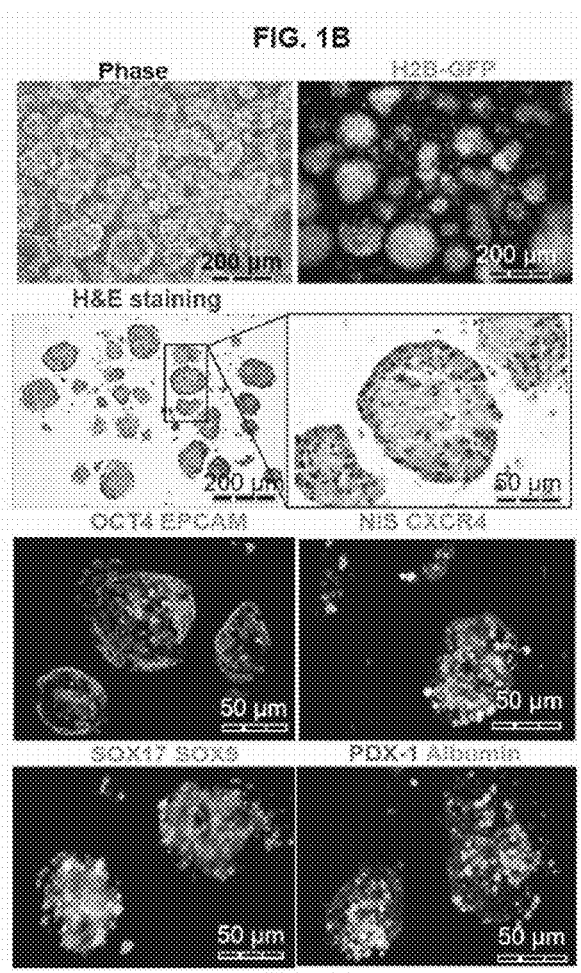

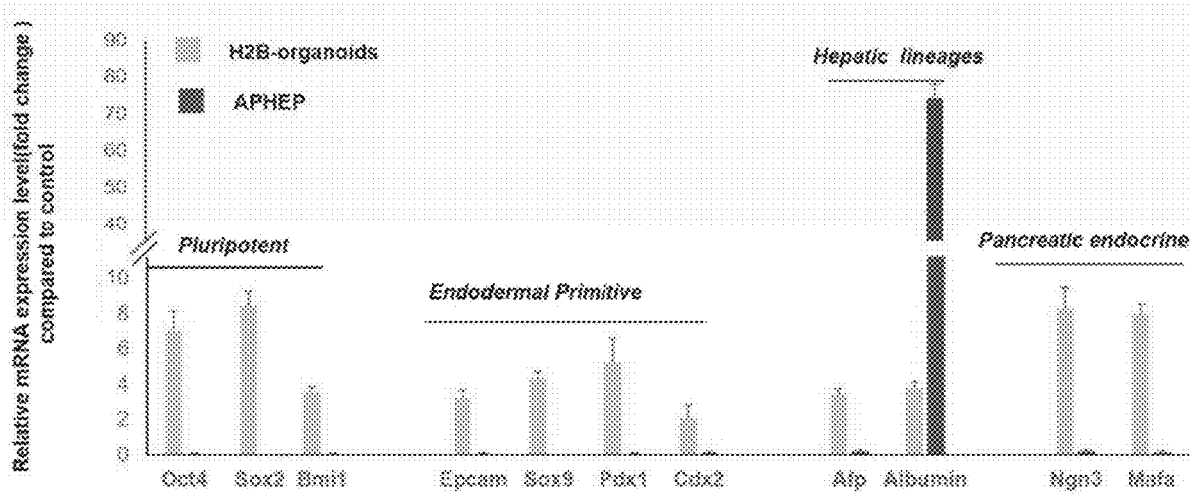

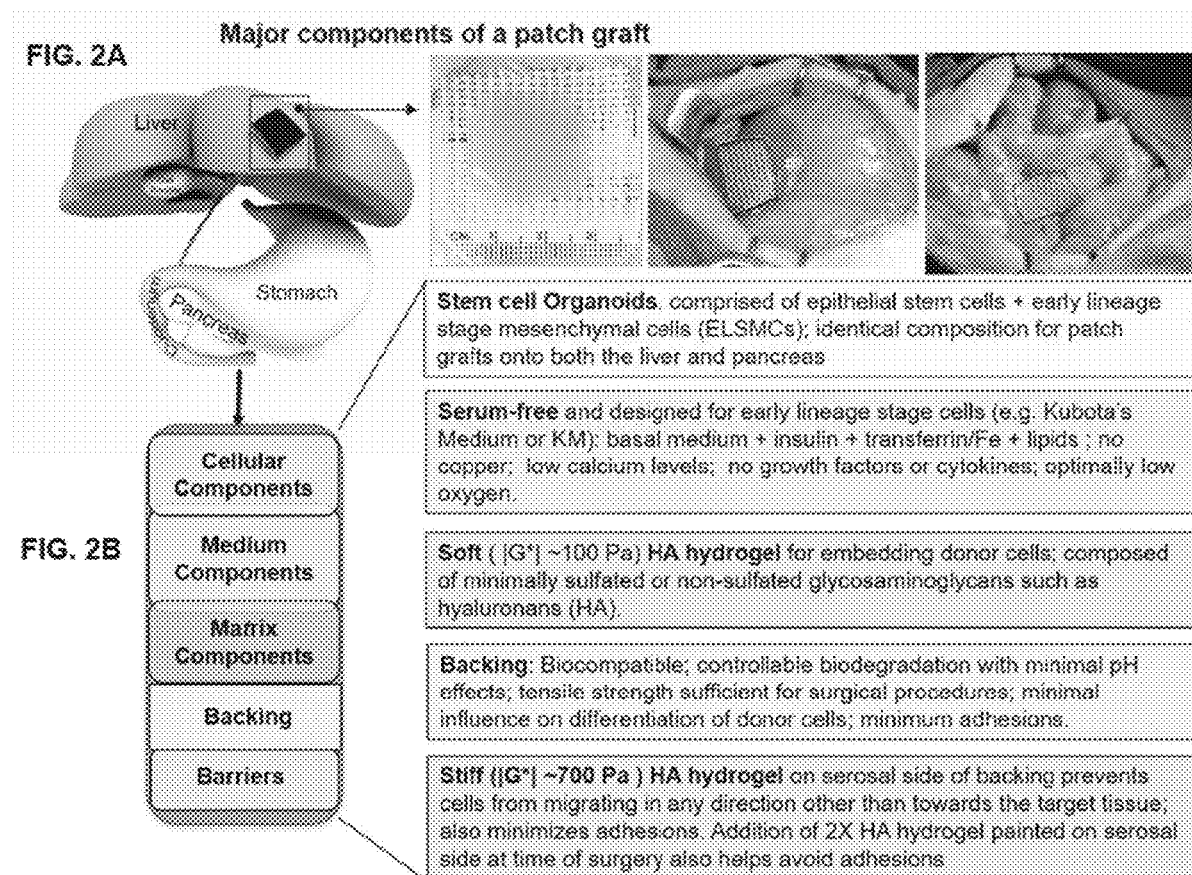

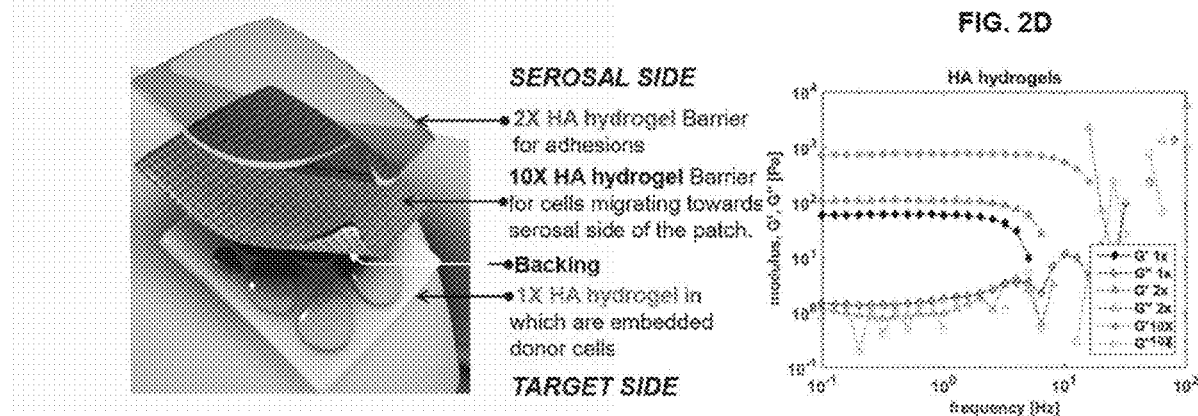
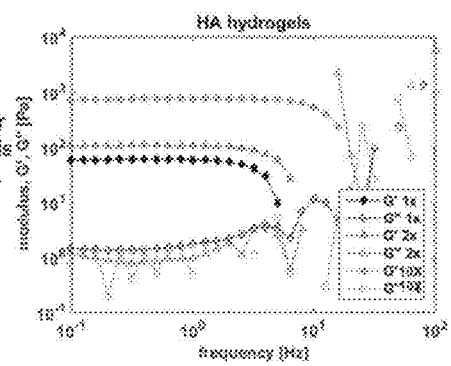
FIG. 2C
FIG. 2D
FIG. 2E Formulations and Rheological Features of HA Hydrogels
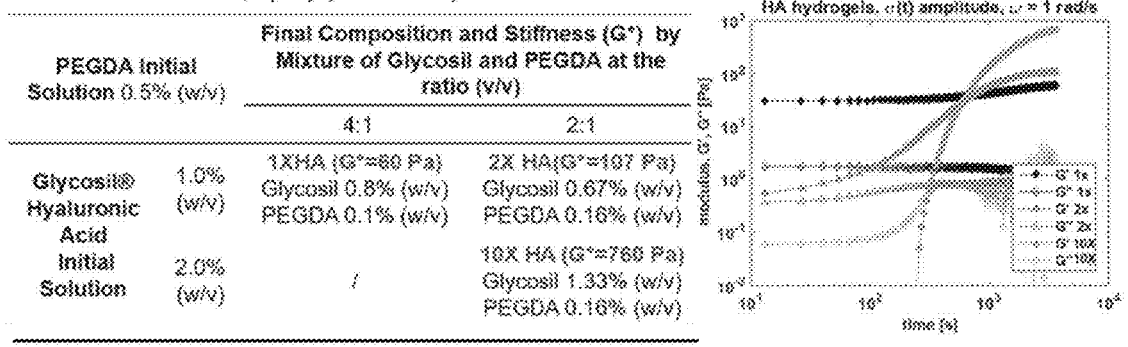

One Week

Two Weeks

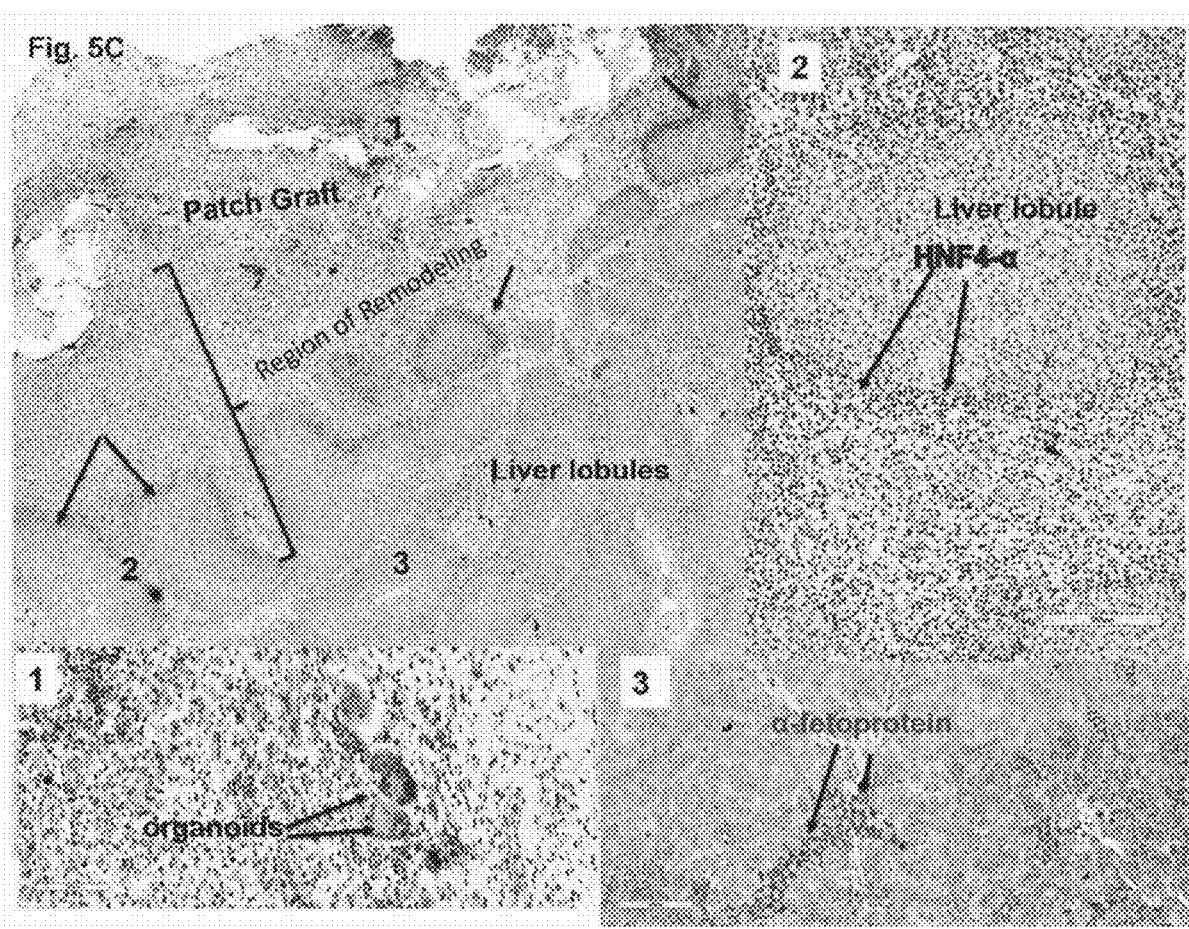

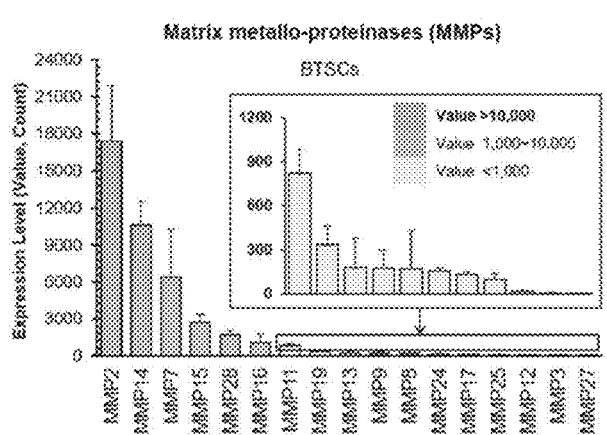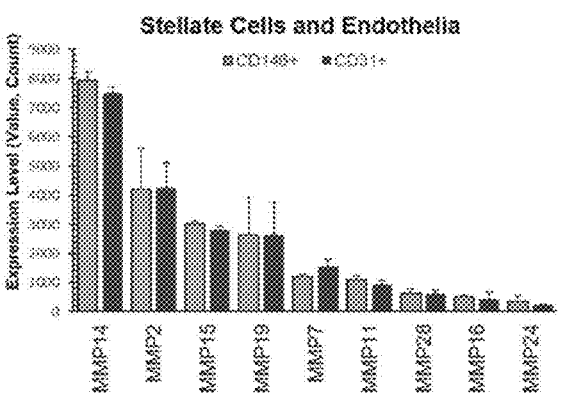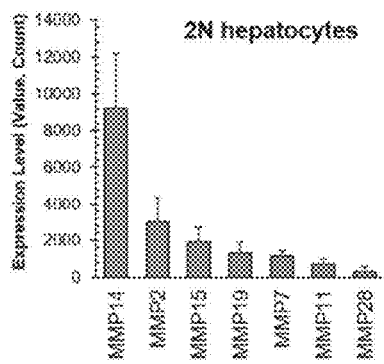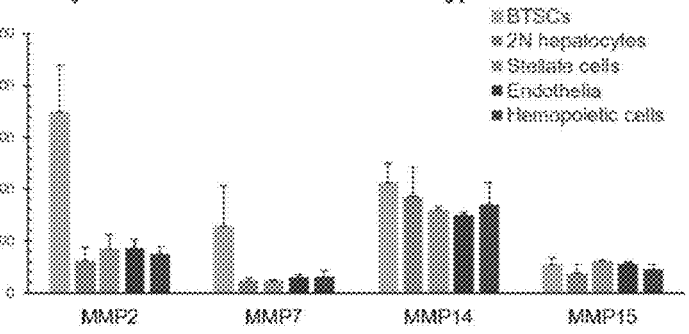

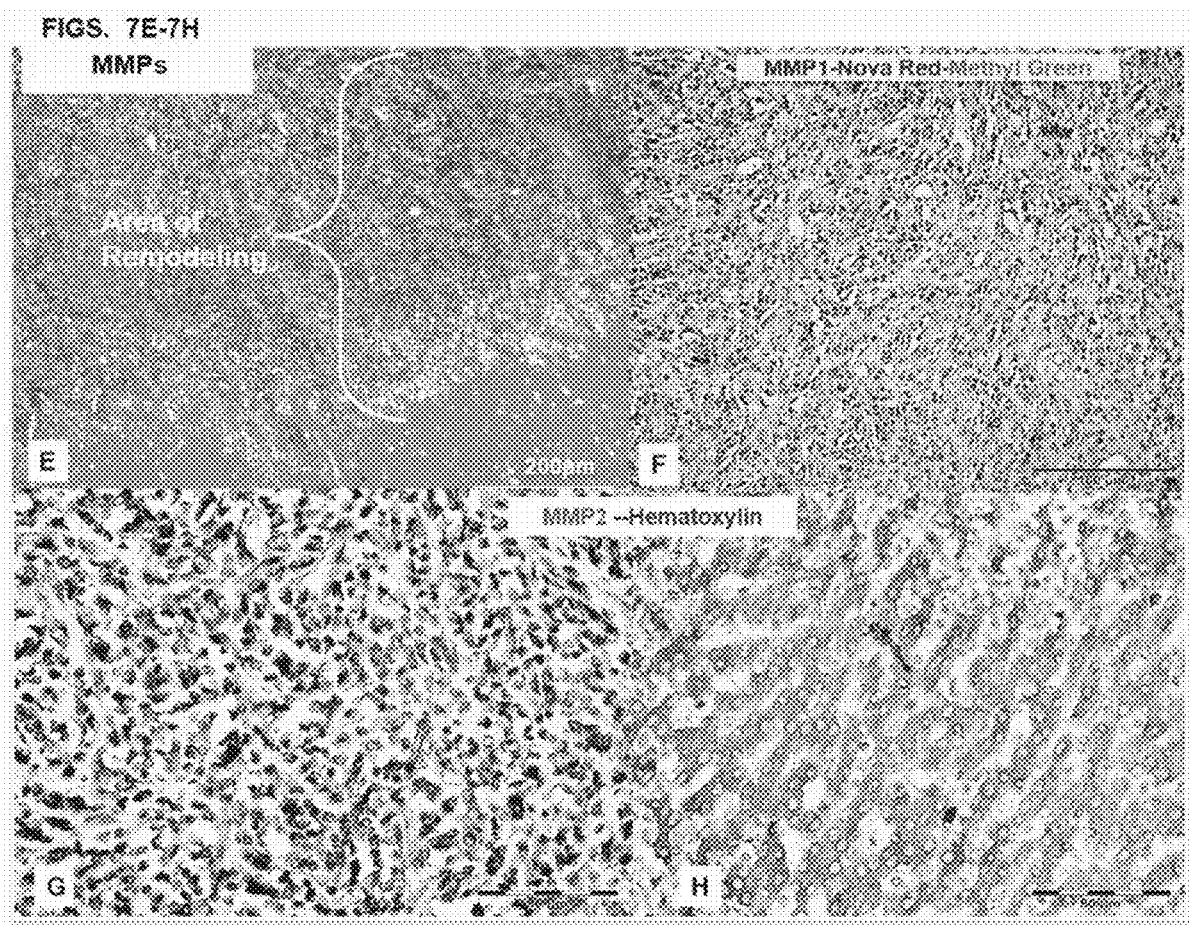

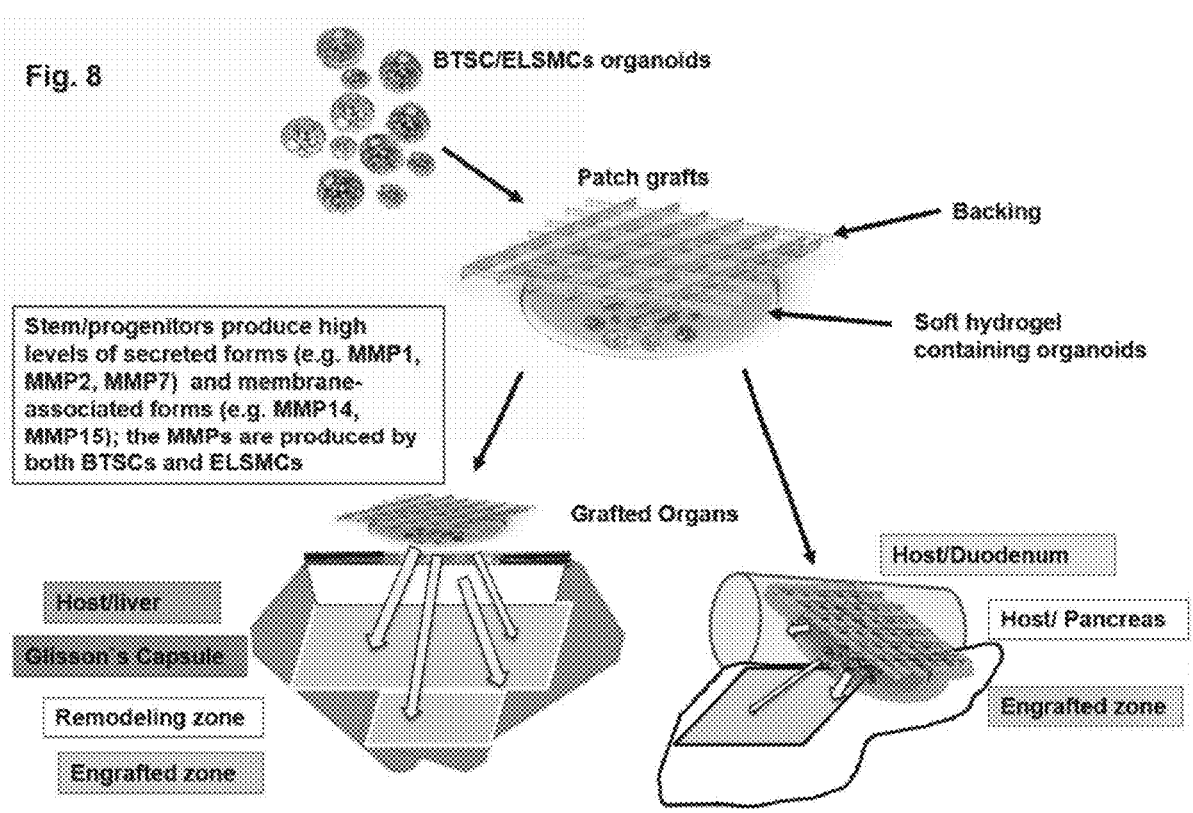

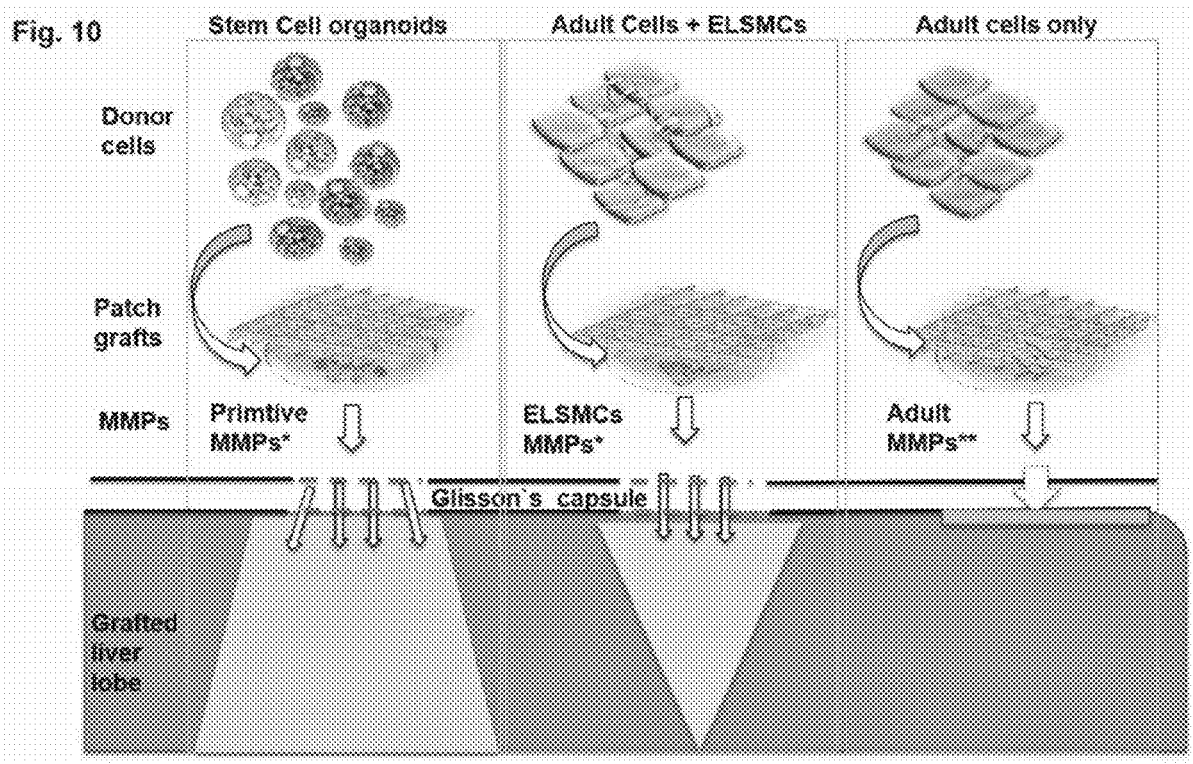

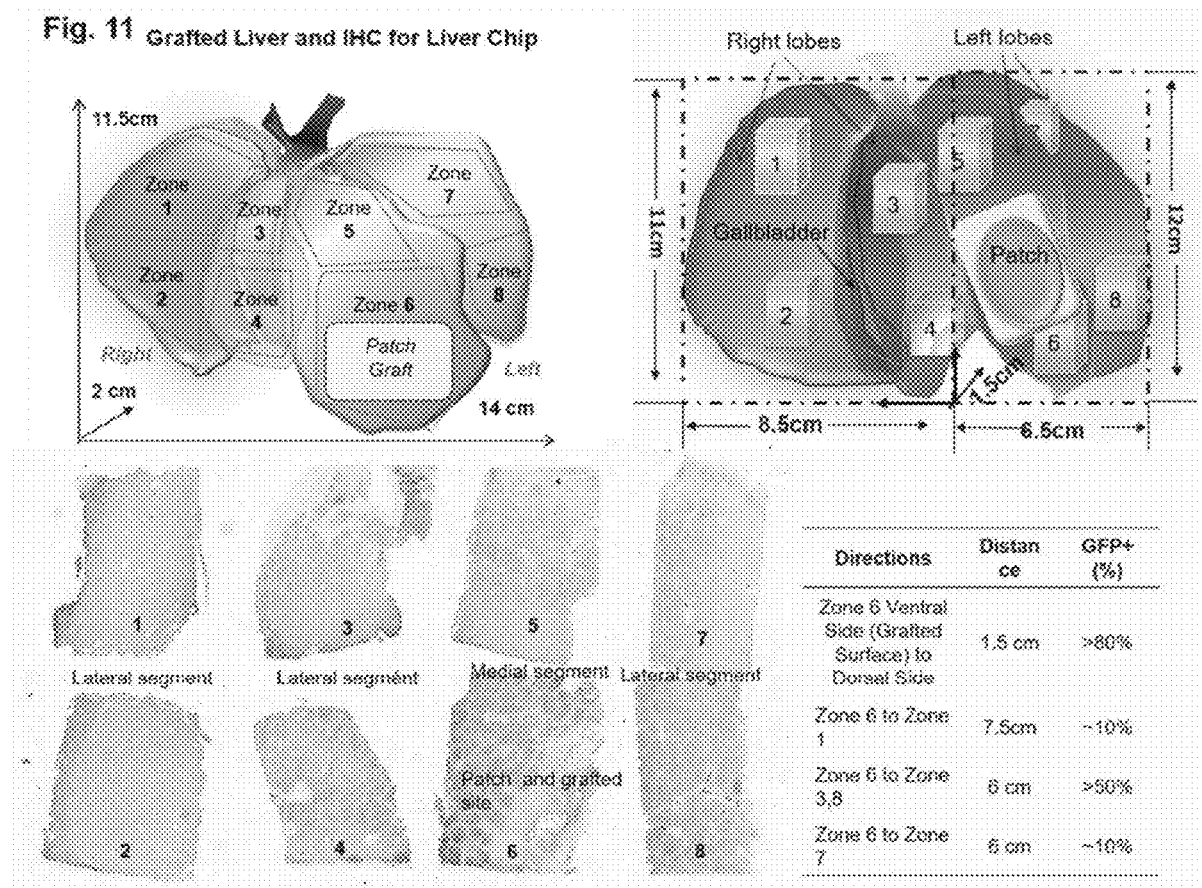

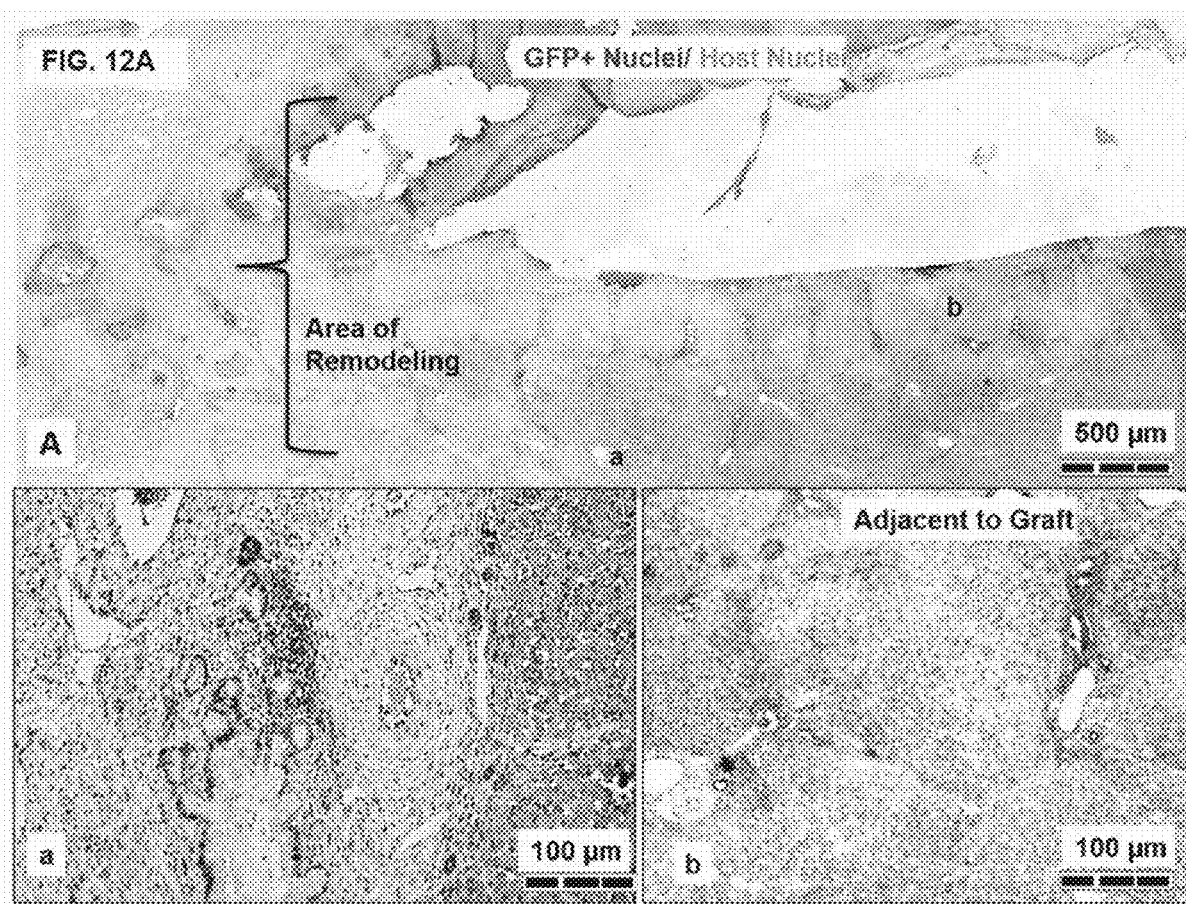

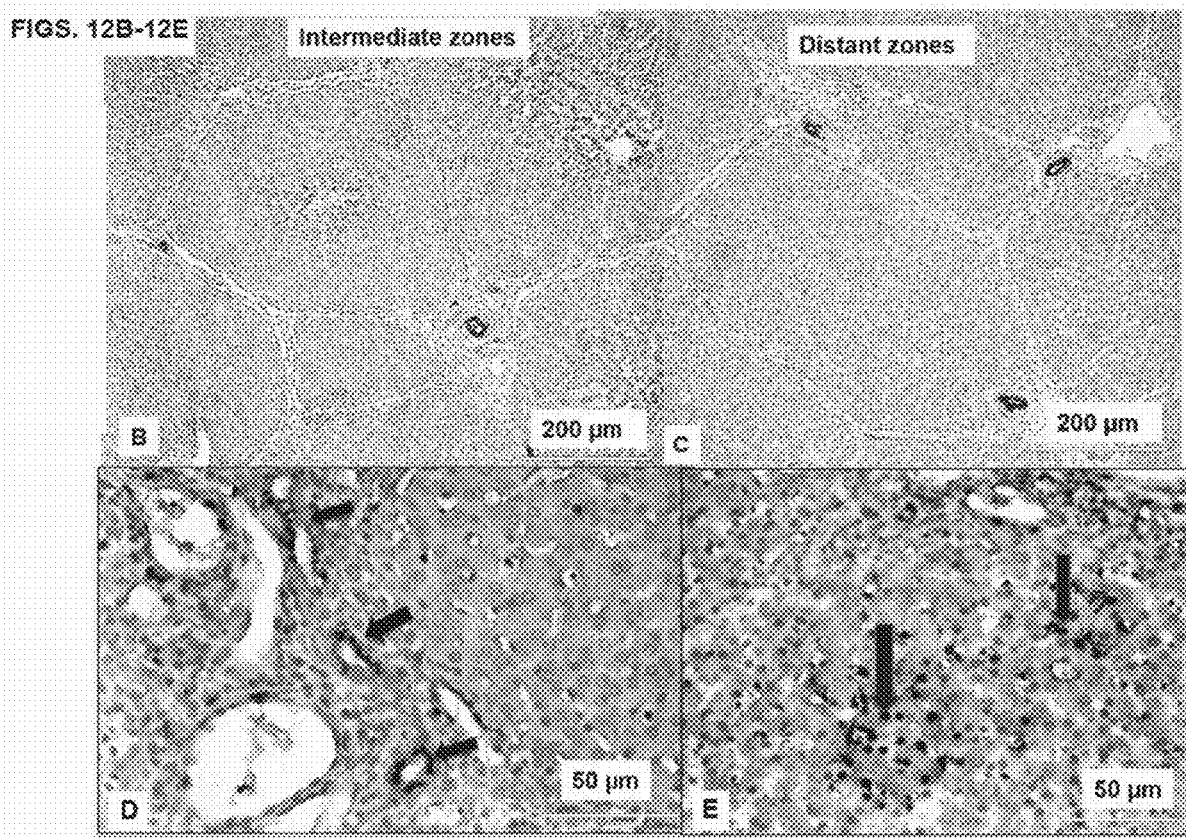

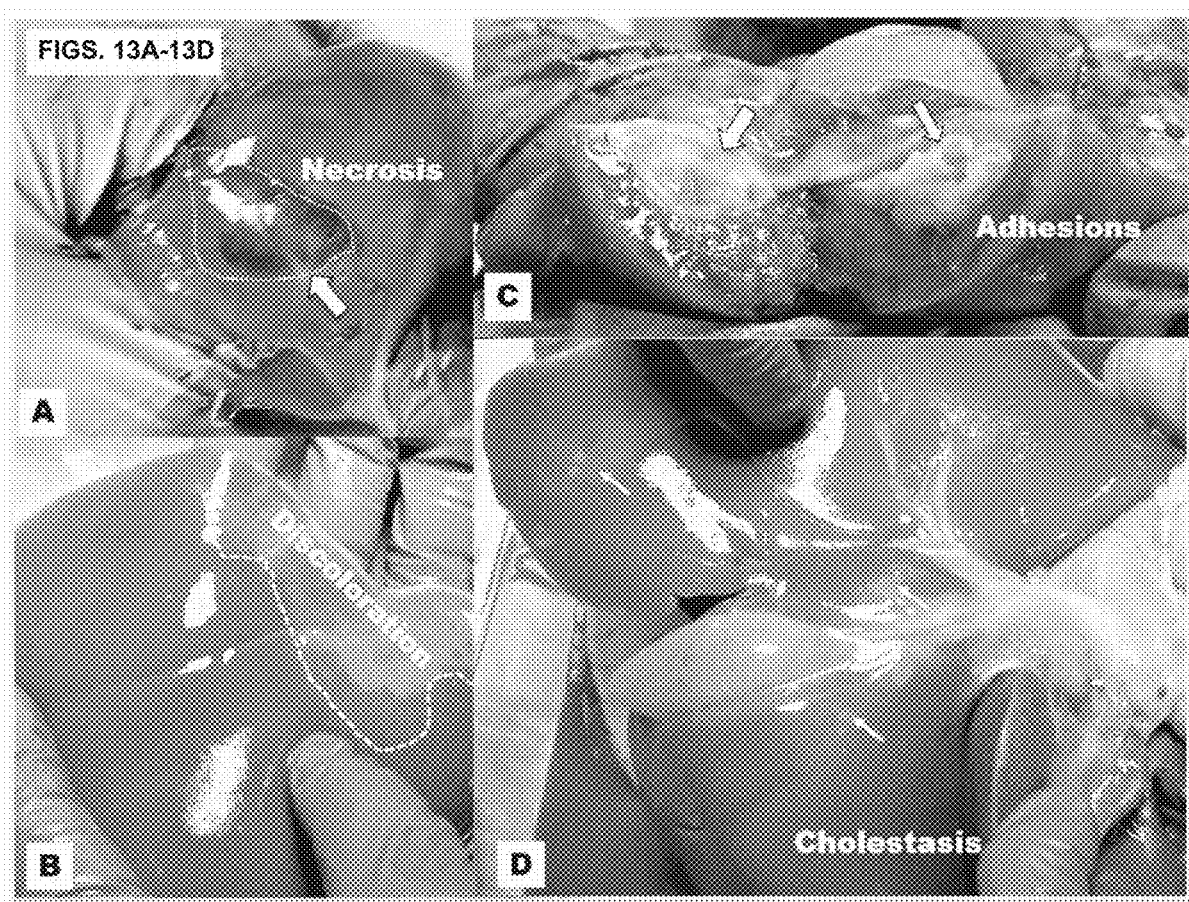

FIG. 14A

1) Brunner's Glands - A, B, C CD44, TRA-160, TRA-181, CK7

2) BTSCs, stage 1 -A, B, C, NIS, CD44

3) BTSCs, stage 2 -A, B, C, NIS, CD44, CD133, LGR5

4) BTSCs, stage 3 -A, B, C, CD44, CD133, LGR5, EpCAM

5L) Heptaic Stem Cells- A (weak), B, CD44, LGR5, CD133, EpCAM, NCAM

6L) Hepatoblasts -A (+/-), B, CD44, LGR5, CD133, EpCAM, ICAM-1, AFP, P450A7

7LH) Hepatocytes -albumin, transferrin, tyrosine aminotransferase, late P450s

7LC) Cholangiocytes-aquaporins, bile, CK7, CK19, primary cilia

OR 

5P) Pancreatic Stem Cells -A (weak), C, CD44, LGR5, CD133, EpCAM, NCAM

6P) Pancreatic Ductal Progenitors - C, CD44, LGR5, EpCAM, ICAM-1, HNF-1B

7P) Islets -NGN3, insulin, glucagon

8PA) Acinar cells- Amylase, lipase, chymotrypsin

A= pluripotency genes (e.g. OCT4, SOX2, Nanog, SALL4, Bmi-1, KLF4, KLF5, etc.)

B= transcription factors for liver (e.g. SOX9, SOX17, HNF-4alpha, etc.)

C= transcription factors for pancreas (e.g. SOX9, PDX1, NGN3, PTF1a, etc.)

FIG. 14B

Stages 1-5 (both 5L and 5P) of the epithelia are partnered with "early lineage stage mesenchymal cells" (ELSMCs):
All of these 3 cellular sub populations have negligible MHC antigens, have low forward scatter (that is have a small diameter, typically below 10 um) and low side scatter (meaning high nucleus to cytoplasmic ratio); they are comprised of at least 3 subpopulations:

Angioblasts-- CD117+, CD133+, VEGFr+, Van Willebrand factor+ (vWF), but negative for CD31 (also called PECAM)
Precursors to endothelia-- CD133+, VEGFr,+vWF+, CD31 +/- (i.e. low)
Precursors to stellate cells-- CD146+, alpha smooth muscle action (ASMA)+, desmin+, -ICAM-1$^+$VCAM-1$^+$ β3-integrin$^+$, but negative or minimally expressing vitamin A

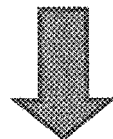

Pancreatic Ductal Progenitors --
Precursors to endothelia-- CD133+, VEGFr,+vWF+, CD31+
Precursors to stellate cells-- CD146+, alpha smooth muscle actin (ASMA)+, desmin+, ⁻ICAM-1$^+$VCAM-1$^+$ -β3-integrin$^+$, vitamin A (low)

Islets
Endothelia-- CD133+, VEGFr+, vWF+, CD31++ (also called PECAM), caveclin-1, basement membrane components (i.e. basal lamina containing type IV and VI collagen, laminin and forms of Heparan sulfate/Heparin proteoglycans (Igypicans, syndecans)

Acinar cells
Stellate cells-- CD146+, alpha smooth muscle actin (ASMA)+, desmin+, ⁻ICAM-1$^+$ VCAM-1$^+$, vitamin A+, HGF, fibrillary collagens (type 1 and 3), chondroitin sulfate proteoglycans (degree of sulfation of the proteoglycans increases with maturational stage, so late stage ones will be dermatan sulfate proteoglycans)

FIG. 14B
(CONTINUED)

Stages 1-5 (both 5L and 5P) of the epithelia are partnered with "early lineage stage mesenchymal cells" (ELSMCs): All of these 3 cellular sub populations have negligible MHC antigens, have low forward scatter (that is have a small diameter, typically below 10 um) and low side scatter (meaning high nucleus to cytoplasmic ratio); they are comprised of at least 3 subpopulations:

Angioblasts--CD117+, CD133+, VEGFr+, Van Willebrand factor+ (vWF), but negative for CD31 (also called PECAM)
Precursors to endothelia--CD133+, VEGFr,+vWF+, CD31 +/- (i.e. low)
Precursors to stellate cells --CD146+, alpha smooth muscle actin (ASMA)+, desmin+, ⁻ICAM-1⁺VCAM-1⁺, β3-integrin⁺, but negative or minimally expressing vitamin A

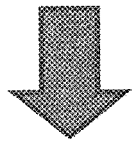

Hepatoblasts
Precursors to endothelia--CD133+, VEGFr,+vWF+, CD31+
Precursors to stellate cells --CD146+, alpha smooth muscle actin (ASMA)+, desmin+, ⁻ICAM-1⁺-VCAM-1⁺ β3-integrin⁺, vitamin A (low)

Diploid Hepatocytes
Endothelia-- CD133+, VEGFr+, vWF+, CD31++ (also called PECAM), caveolin-1, basement membrane components (i.e. basal lamina containing type IV and VI collagen, laminin and forms of heparan sulfate proteoglycans (HS-PGs) that increase in sulfation with maturation

Polyploid Hepatocytes
Fenestrated endothelia- CD133+, VEGFr+, vWF+, CD31+++, caveolin-1, but absence of basement membrane though presence of HS-PGs that are highly sulfated and so are referred to as heparin proteoglycans

Cholangiocytes
Stellate cells-- CD146+, alpha smooth muscle actin (ASMA)+, desmin+, ⁻ICAM-1⁺, VCAM-1⁺, vitamin A+, HGF, fibrillar collagens (type 1 and 3), chondroitin sulfate proteoglycans (degree of sulfation of the proteoglycans increases with maturational stage, so late stage ones will be dermatan sulfate proteoglycans)

SEQUENCE LISTING

<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
atcctgggct acactgagga c                                           21

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagtggtcgt tgagggcaat g                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttccttcctc catggatctg                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atctgctgga ggctgaggta                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gccctgcagt acaactccat                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctgatcatg tcccgtaggt                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgaagctgga caaggagaag                                                20
```

-continued

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctgaacacc ttcccaaaga                                                 20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accagagaat gctatccaga ac                                              22

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcactcgct ccaaacagg                                                  19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccttggccct gaacaaaata                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atttctttcc cagggagtgg                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cggttcgagc aagaataagc                                                 20

<210> SEQ ID NO 14
```

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtaatccggg tggtccttct                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcattgatgc cacaaccatt                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgaaaagccc cggaactaat                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggctgctcat tgagaggagt                                               20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atgttcccga actccaagg                                                19

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agaaccccca ggtctctgtc tt                                            22

<210> SEQ ID NO 20
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagtccgaaa cactccctca ca                                            22

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgcgtttctg gttgcttaca c                                             21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acttcttgct cttggccttg g                                             21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agtctgccaa gctgctgata                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agccttggga aatctctggc                                               20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agtgatactg gattggcgtt g                                             21

<210> SEQ ID NO 26
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 26
tagggagcct tccaatgtgt                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcttcagcaa ggaggaggtc                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctcgctctc cagaatgtgc                                                    20
```

PATCH GRAFT COMPOSITIONS FOR CELL ENGRAFTMENT

CROSS REFERENCE TO RELATED APPLICATIONS

This application claims priority under 35 U.S.C. § 119(e) to U.S. Application No. 62/518,380, filed Jun. 12, 2017, and to U.S. Application No. 62/664,694, filed Apr. 30, 2018, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Aug. 14, 2018, is named 069961-2804_SL.txt and is 6,662 bytes in size.

FIELD OF THE INVENTION

The present invention is directed generally to the field of transplantation of cells or tissue engrafting. More specifically, from solid organs or tissues into solid organs or tissues, especially to internal organs. The invention concerns compositions and methods providing strategies for the rapid transplantation, engraftment and integration of cells into solid organs and tissues to treat diseases or conditions of solid organs or tissues, or to establish model systems of a disease.

Representative examples of this potential are cell therapies for treatment of hepatic or pancreatic diseases.

BACKGROUND OF THE INVENTION

There has long been a need for grafting strategies for cells from solid organs, strategies distinct from those used for transplantation of hemopoietic cells or for mesenchymal stem/progenitors. Turner, R., et al. *Transplantation* 90, 807-810 (2010); Gattinoni, L. et al. *Nature Medicine* 23, 18-27 (2017); Trounson A. et al. *Cell Stem Cell* 17, 11-22 (2015); Sun B. K. et al. *Science* 346, 941-945 (2014); Lainas, P. et al. *J Hepatol* 49, 354-362 (2008). Transplantation of hematopoietic cells and of mesenchymal cells is done routinely by delivery of cells via a vascular channel and is dependent on activation of adhesion molecules in transplanted cells when in relevant target sites because of micro-environmental signaling, a process referred to as "homing." Methods used for skin (with similar ones for ocular targets) employ grafting methods with cells applied directly to target sites. Sun B. K. et al. *Science* 346, 941-945 (2014). Many grafting methods for skin are utilizable for cells from solid internal organs but require substantial modifications to accommodate the microenvironment of these internal organs. Grafts must contend with mechanical forces exerted by interactions of tissues and organs on each other; examples include the effects of lungs during breathing, or the compression of the liver against the diaphragm, or the transient effects of mechanical forces exerted by the intestinal tract on neighboring tissues during processing of foods. Grafts, especially those for internal organs, are challenging to design because of concerns with respect to size, shape, and complexity in the structure of organs in addition to the dynamic mechanical forces evident.

For decades, cell therapies for cells from solid organs other than skin were attempted using transplantation via a vascular route or by direct injection into the tissue. Most transplanted cells, when delivered by either of these strategies, either die or are transported to ectopic sites, where they can live for months and create tissue in inappropriate sites, resulting potentially in adverse effects clinically. Turner, R., et al. *Transplantation* 90, 807-810 (2010); Lanzoni, G. et al. *Stem Cells* 31, 2047-2060 (2013). Engraftment in liver can be improved by coating the cells with hyaluronans and delivering them vascularly to the liver; the increased efficiency of engraftment is due to the liver's natural process of clearance of hyaluronans. Nevi et al. *Stem Cell Research & Therapy* 8, 68, 2017. However, this improvement is still less efficient than that with grafting strategies and, importantly, still allows for delivery of cells to ectopic sites.

There remains a need for improved methods of cell engraftment into solid organs. This disclosure fulfills this need and provides related advantages.

SUMMARY OF THE INVENTION

There has long been a need for grafting strategies for cells from solid organs (Turner, R., et al. Transplantation 90, 807-810 (2010), strategies distinct from those used for transplantation of hemopoietic cells, mesenchymal stem cells or for skin. Transplantation of hemopoietic cells and mesenchymal cells is done routinely via a vascular channel and is dependent on activation of adhesion molecules in relevant target sites because of micro-environmental signaling, a process referred to as "homing". Methods used for skin employ grafting methods with cells applied directly to target sites.

Transplantation of cells from solid organs other than skin have long used vascular delivery. This is not logical, since adhesion molecules on these cells are always activated and result in rapid (seconds) cell aggregation that can generate life-threatening emboli. Even if emboli are managed successfully to minimize health risks, the efficiency of cell engraftment is low, only ~20% for adult cells and even lower (<5%) for stem/progenitors. Most transplanted cells either die or are transported to ectopic sites, where they can live for months, creating tissue in inappropriate sites resulting in possible adverse effects clinically. The small percentage of cells that engraft into target sites integrate slowly, requiring weeks to months to become a significant portion of the tissue. There is improvement in engraftment in liver if cells are coated with hyaluronans and delivered vascularly due to the tissue's (e.g. liver's) clearance of hyaluronans. (Nevi et al. Stem Cell Research & Therapy 8, 68, 2017).

Applicants propose a radically different approach, one found even more successful than coating cells with hyaluronans: placing grafts directly onto the surface of the target site and using grafting biomaterials and the unique phenotypic traits of certain cells when they are in conditions of the graft biomaterials to enhance transplantation. This parallels some aspects of strategies of cell therapies for skin but requires substantial, modifications for internal organs given mechanical effects, abrasion or compression of organs near to each other, and given the unique fluid microenvironments around specific organs and the size, structure, and complexity of organs.

Described herein are novel patch graft compositions and methods for transplantation of cells into tissue and solid organs. In some embodiments, the methods and grafts are adapted for internal organs, with design features dependent on the level of maturity of the cells, especially whether cells are stem cells or mature cells. In some embodiments, the donor cells (optionally autologous or allogenic) for the patch grafts are disclosed herein incorporated into the graft biomaterials in optionally as a mixture of cells or the form of organoids, aggregates of epithelial stem cells and their native, lineage-stage appropriate mesenchymal cell partners—e.g. mesenchymal stem/progenitor cells such as early lineage stage mesenchymal cells (ELSMCs). In some embodiments, the donor cells are adult cells incorporated into the graft materials as cell suspensions of adult epithelia and partnered with mesenchymal stem/progenitor cells, optionally ELSMCs, at ratios designed to optimize their expression of membrane-associated and/or secreted matrix metallo-proteinases (MMPs). In some embodiments, other variables of importance are the grafting biomaterials and the backing material, both required to be neutral in effects on the differentiation of the donor cells.

Aspects of the disclosure relate to a patch graft for sustaining and maintaining a single cell population or a mixed population of cells, comprising: (a) a single cell type or a mixed population having two or more cell types, at least one of which is at an early lineage stage that is capable of expressing membrane-associated and/or secreted matrix metalloproteinases (MMPs), or which has MMPs included from another source (e.g., purified or recombinant MMPs), said cell population or mixed population supported in a medium present in a hydrogel matrix having a viscoelasticity sufficient to allow for migration of said mixed population, optionally, within or away from said hydrogel and/or within or away from the patch graft; (b) a backing comprising a biocompatible, biodegradable material having a viscoelasticity sufficient to inhibit a migration of said mixed population in a direction of said backing; and, optionally, (c) a hydrogel overlaid on a serosal (i.e. outside) surface of said backing, which is opposite to that in contact with said mixed population and, in embodiments where the patch graft is tethered to a target site, is opposite the side in contact with the target site (e.g. organ or tissue). In some embodiments, this layer prevents or inhibits adhesions by or from other tissues or organs. In some embodiments, the patch graft is configured to sustain and maintain said mixed population while inhibiting said at least one early lineage stage cell type from differentiating or further maturing to a later lineage stage that is no longer capable of expressing membrane-associated and/or secreted MMPs. The patch graft may be a single layer plus a backing or multiple layers.

In some embodiments, said backing is porous or non-porous. In some embodiments, the backing comprises a porous mesh, scaffold, or membrane. In some embodiments, the backing comprises silk; a synthetic textile; or a natural material such as amnion, placenta, or omentum; or a combination thereof. In some embodiments, said backing comprises a porous mesh infused with a hydrogel. In further embodiments, such an infusion prevents cell migration away from the target organ or tissue. In some embodiments, said backing comprises a solid material.

In some embodiments, one or more of said hydrogels comprise hyaluronans.

In some embodiments, said medium comprises Kubota's medium or another medium supportive of stem cells and able to maintain stemness.

In some embodiments, said mixed population comprises mesenchymal cells and epithelial cells. In some embodiments, said epithelial cells may be ectodermal, endodermal, or mesodermal. In some embodiments, said mesenchymal cells comprise early lineage stage mesenchymal cells (ELSMCs). In some embodiments, said ELSMCs comprise one or more of angioblasts, precursors to endothelia, precursors to stellate cells, and mesenchymal stem cells (MSCs). In some embodiments, said epithelial cells comprise epithelial stem cells. In some embodiments, said epithelial cells comprise biliary tree stem cells (BTSCs). In some embodiments, said epithelial cells comprise committed and/or mature epithelial cells. In some embodiments, said committed and/or mature epithelial cells comprise mature parenchymal cells. In some embodiments, said mature parenchymal cells comprise one or more of hepatocytes, cholangiocytes, and islet cells. In some embodiments, said mesenchymal cells and epithelial cells both comprise stem cells.

In some embodiment said mixed population comprises autologous and/or allogeneic cells.

In some embodiments, one or more cell types are genetically modified.

Further aspects related to methods employing the disclosed patch graft compositions. Accordingly, provided herein are methods of engrafting cells into a target tissue comprising, consisting of, or consisting essentially of contacting the target tissue with a patch graft disclosed herein above.

In some embodiments of the methods, the target tissue is selected from the group consisting of liver, pancreas, biliary tree, thyroid, thymus, gastrointestine, lung, prostate, breast, brain, bladder, spinal cord, skin and underlying dermal tissues, uterine, kidney, muscle, blood vessel, heart, cartilage, tendons, and bone tissue. In some embodiments of the methods, the target tissue is liver tissue. In some embodiments of the methods, the target tissue is pancreatic tissue. In some embodiments of the methods, the target tissue is biliary tree tissue. In some embodiments of the methods, the target tissue is gastrointestinal tissue. In some embodiments, the tissue is diseased, damaged, or has a disorder. In some embodiments of the methods, the target tissue is kidney tissue.

In some embodiments of the methods, the target tissue is an organ. In some embodiments of the methods, the organ is an organ of the musculoskeletal system, the digestive system, the respiratory system, the urinary system, the female reproductive system, the male reproductive system, the endocrine system, the circulatory system, the lymphatic system, the nervous system, or the integumentary system. In some embodiments of the methods, the organ is selected from the group consisting of liver, pancreas, biliary tree, thyroid, thymus, stomach, intestines, lung, prostate, breast, brain, bladder, spinal cord, skin and underlying dermal tissues, uterus, kidney, muscle, blood vessel, heart, cartilage, tendon, and bone. In some embodiments, the organ is diseased, damaged, or has a disorder.

Also provided herein are methods of treating a subject with a liver disease or disorder, the methods comprising, consisting of, or consisting essentially contacting the subject's liver a patch graft disclosed herein above. In some embodiments of the methods, the liver disease or disorder is liver fibrosis, liver cirrhosis, hemochromatosis, liver cancer, biliary atresia, nonalcoholic fatty liver disease, hepatitis, viral hepatitis, autoimmune hepatitis, fascioliasis, alcoholic liver disease, alpha 1-antitrypsin deficiency, glycogen storage disease type II, transthyretin-related hereditary amyloidosis, Gilbert's syndrome, primary biliary cirrhosis, primary sclerosing cholangitis, Budd-Chiari syndrome, liver trauma, or Wilson disease.

In other aspects, provided herein are methods of treating a subject with a disease or disorder of the pancreas, the methods comprising, consisting of, or consisting essentially of contacting the subject's pancreas with a patch graft disclosed herein above. In some embodiments of the methods, the disease or disorder of the pancreas is diabetes mellitus, exocrine pancreatic insufficiency, pancreatitis, pancreatic cancer, sphincter of Oddi dysfunction, cystic fibrosis, pancreas divisum, annular pancreas, pancreatic trauma, or hemosuccus pancreaticus.

In other aspects, provided herein are methods of treating a subject with a gastrointestinal disease or disorder, the method comprising, consisting of, or consisting essentially of contacting one or more of the subject's intestines with a patch graft disclosed herein above. In some embodiments, the gastrointestinal disease or disorder is gastroenteritis, gastrointestinal cancer, ileitis, inflammatory bowel disease, Crohn's disease, ulcerative colitis, irritable bowel syndrome, peptic ulcer disease, celiac disease, fibrosis, angiodysplasia, Hirschsprung's disease, pseudomembranous colitis, or gastrointestinal trauma.

In some aspects, provided herein are methods of treating a subject with a kidney disease or disorder, the methods comprising, consisting of, or consisting essentially of contacting one or more of the subject's kidneys with a patch graft disclosed herein above. In some embodiments of the methods, the kidney disease or disorder is nephritis, nephrosis, nephritic syndrome, nephrotic syndrome, chronic kidney disease, acute kidney injury, kidney trauma, cystic kidney disease, polycystic kidney disease, glomerulonephritis, IgA nephropathy, lupus nephritis, kidney cancer, Alport syndrome, amyloidosis, Goodpasture syndrome, or Wegener's granulomatosis.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1D provides information about porcine donor cells for the patch grafts. FIG. 1A is a schematic of the process and estimates of the time required for preparing organoids, assembling patch grafts and doing the surgeries. In FIG. 1B, donor cells for the stem cell patch grafts were isolated from cell suspensions of biliary tree tissue from transgenic pigs; the cells were prepared as organoids in serum-free Kubota's Medium and on low attachment culture dishes. Organoids of biliary tree stem cells (BTSCs) and of their early lineage stage mesenchymal cell (ELSMCs) partners, angioblasts and precursors to endothelia and to stellate cells. They are shown in a phase micrograph versus one demonstrating expression of the transgene, green fluorescent protein (GFP). All of the cells of the aggregate are green, since the transgene is in both the epithelial cells and the mesenchymal cells. The transgene was coupled to the histone (H-2B) locus. Histology of the stem cell organoids that were paraffin embedded, sectioned and stained with hematoxylin/eosin. (d) Magnified image of an organoid of BTSC and ELSMCs. FIG. 1C shows immunohistochemistry (IHC) demonstrating expression of stem cell, hepatic and pancreatic markers indicating that these cells are precursors to both liver and to pancreas. The IHC assays indicate outer layers with intermediate stage stem cell markers such as EpCAM and interior cells expressing very primitive genes such as pluripotency genes and endodermal transcription factors (e.g. SOX17, SOX9, PDX1). FIG. 1D is a representative qRT-PCR assays assessing expression of various genes in the organoids and indicating that cells are stem cells or early progenitors. The controls were mature hepatocytes from piglet livers.

FIGS. 2A-2F provides information about the major components of patch grafts. FIG. 2A is a schematic of a patch graft affixed to the liver of a pig, and on the right, the composition of the grafts. Early lineage stage cells, both the epithelia and the mesenchymal cells, are sources for production of matrix metallo-proteinases (MMPs), key regulators of engraftment. The matrix components of the graft biomaterials into which donor cells are placed are soft (~100 Pa), without (or with minimal) sulfation, such as hyaluronan hydrogels. The structure of the graft consist of layers of biomaterials and cells tethered to the target site. The medium components are devoid of serum, growth factors and cytokines influential to differentiation of the donor cells and should be ones tailored for survival and expansion of early lineage stage cells such as stem/progenitors. The backing has sufficient tensile strength to be used in surgical procedures but be neutral in its effects on the differentiation of the donor cells (e.g. ones with type I collagen should be avoided). The backing is impregnated or coated with a more rigid 10× hydrogel (~700 Pa) to serve as a barrier to orient the migration of donor cells towards the target tissue and to minimize adhesions. After attachment to the target site, a 2×HA hydrogel, one that is sufficiently fluid to be coated or painted onto the serosal surface, is added and used to further minimize adhesions. FIG. 2B depicts the graft affixed to the liver or the pancreas of a host. FIG. 2C is a schematic of the graft demonstrating the layers constituting the graft composition. FIG. 2D depicts the results of assays empirically assessing the rheological or viscoelastic properties (shear and compressive mechanical forces) of the specific hydrogel layers. FIG. 2E provides a formulation of the viscoelastic properties of the 3 layers of hydrogels. FIG. 2F is a close up image of a patch graft sutured to the surface of the liver of a pig.

FIG. 3A (Panels (a)-(d)) shows the results of Trichrome staining of the patch graft at one week. Trichrome identifies collagens (blue), cytoplasm (red) and nuclei (black), and it was used to identify Glisson's capsule (normally adjacent to the surface of liver lobules) and adhesions (on the serosal surface of the grafts). There is a high level of blue staining in the layers at the serosal surface and implicate adhesions to the graft. Also, the graft has separated from the host tissue at the interface between the backing and the host; this was found frequently due to the wealth of MMPs produced at this interface. The remodeling regions provide evidence of the loss of classic lobule structure of the liver; they result in a region in which the donor cells are migrating into the tissue and, in parallel, altering the host tissue structure. In low magnification images (a), Trichrome staining of grafts placed on to the liver validated that extensive remodeling of the Glisson capsule was occurring and resulted often in a separation between the graft and the host liver. In higher magnification images (b) the remodeling region is remarkably broad and consisting of areas (c) near to the graft where liver lobule structure is missing altogether and (d) regions within the remaining liver lobules that are undergoing breakdown in the remodeling process. FIG. 3B (Panels (a)-(b)) shows the results of Trichrome staining of the patch graft at three weeks. Hyaluronans in the graft have been resorbed leaving only the backing (a). With resorption of HA, the Glisson capsule reappears (b) and the liver lobules near to the graft have stabilized again into their typical histological patterns, such as lobule and acini for liver. The arrow in (b) indicates the reappearance of collagens in the reformation of the Glisson capsule. FIG. 3C (Panels (a)-(c)) and FIG. 3D (Panels (a)-(c)) shows the results of hematoxylin/eosin staining of a section from the grafts at one week post grafting (C) and two weeks post grafting (D). The figures at the top are 40×. At sites within the figure (a,b,c) are enlargements that are magnified at 100×; the rectangular image below each of these is magnified at 200×. Shown are 3 sites of the graft: (a) a site within the backing and associated graft biomaterials; (b) a site at the interface between graft and host tissue; and (c) a site within the liver lobules. The hematoxylin/eosin staining yields images that contribute to an appreciation of the engraftment and migration process that incorporates features of inflammatory processes.

FIG. 4A is a low magnification image of the patch graft on the surface of a pig liver after one week. The dashed line indicates the interface of the graft and host liver. Donor GFP+ cells (with pink nuclei; white arrows indicate areas with large numbers of the donor GFP+ stem cells) were visualized by labeling with an antibody to GFP and secondarily with one coupled to Novo Red, a red fluoroprobe. Nuclei were stained blue with 4,6-Diamidino-2-phenylindole (DAPI) enabling recognition of host cells having only blue nuclei and donor ones having pink nuclei (merge of DAPI and the Novo Red). FIG. 4B (Sections (a)-(b)) show Host tissue (a) extending into the hyaluronans (HA, the black background) of the graft; tissue by the backing contains occasional organoids (inset) but with most donor cells dispersed into single cells; large numbers of dispersed donor GFP+ stem cells (b) are seen throughout the host tissue. There is no evidence for the Glisson capsule in this area that constitutes the region of remodeling. FIG. 4C demonstrates that engraftment and migration of donor cells was rapid; within a week, all donor cells were within the host liver; there were donor cells both near the graft site and also on the opposite side of the liver lobe (estimate of the distance is at least 1.5 cm from the graft). Ongoing studies are analyzing regions of the piglet livers at greater distances (i.e. other lobes of the liver) to define more precisely how far the migration can go by the donor cells within a defined period of time. Shown are donor cells (pink nuclei) near lobules of host mature hepatocytes (forest green color from auto-fluorescence of lipofuscins) on the distant side of the liver lobe from that of the graft site. FIG. 4D (Panels (a)-(b)) shows that maturation of donor cells to adult fates occurred in parallel with HAs being resorbed. Enlargement of a region containing donor GFP+ cells (single cells with pink nuclei) near to host hepatocytes (a), forest green in color (autofluorescence of lipofuscins), and readily distinguished from mature donor—derived (b) hepatocytes that are lavender in color (merge of the pink—GFP, blue—DAPI, and the green—lipofuscins), that is they were lineage restricted from donor GFP+ stem cells. With other IHC assays (data not shown), the bright, spring green color of cells amidst the plates of both host and donor hepatocytes proved to be endothelia and stellate cells.

FIGS. 5A-5C compares engraftment and maturation of cells in the liver patch grafts after one week and two weeks post-transplantation. FIG. 5A is an examination of porcine liver at 1 week after patch grafting. Sirius red stain, an azo dye staining collagens was used and immunohistochemistry for pan-cytokeratin (pCK) and Sox9; and immunofluorescence (IF) stains were performed on serial 3-μm sections. At the patch graft site, grafted donor cells merged with liver lobules. In the upper panels (original magnification=5×), patch grafts are composed of mesenchymal and epithelial pCK+ cells (arrows). In middle panels, a higher magnification is provided (20×). Epithelial cells show an immunophenotype that is typical of biliary tree stem cells (BTSCs) expressing biliary cytokeratins (pCK) and the endodermal stem cell marker Sox9. BTSCs within the patch graft are arranged in cell strings reassembling bile ductules (arrows) and are in direct continuity with hepatocyte plates of the adjacent liver lobule (arrowheads). Host hepatocytes in lobules are pCK and Sox9 negative. In lower panels (Original magnification=20×), the immunofluorescence for GFP allows one to identify individual grafted cells and their progeny. Hepatocytes in lobules adjacent to the patch graft were GFP positive indicating that these were donor cells derived that had merged with host liver parenchyma. At the interface between patch graft and liver lobules, pCK+/GFP+ ductules (that is donor derived cholangiocytes) were in direct continuity with GFP+/pCK+ cells (donor-derived hepatocytes) within the lobules (arrowheads) suggesting a maturation of grafting cells towards an hepatocyte fate. FIG. 5B is an examination of porcine livers 2 weeks after patch grafting. IF stains reveal that GFP+ cells are present within lobules distant to the graft site. They are dispersed uniformly and so are in a mix of host cells (ones with blue nuclei from DAPI) and of donor cells (pink/purple nuclei from merge of the blue from DAPI and the red of the GFP label). They co-express mature hepatocyte markers such as Hepatocyte Nuclear Factor (HNF) 4α (a mix of green and pink/purple nuclei) and albumin (green cytoplasm and with pink/purple nuclei). Separate or merged channels were included. Nuclei were displayed in blue (DAPI). Original Magnification: 40×. FIG. 5C (Panels 1-3) is an evaluation of porcine livers a week after patch grafting and demonstrating the broad region of remodeling that occurs at the interface between the patch graft and the host tissue. The section in the low magnification image and in the enlarged image of 1 is hematoxylin/eosin (lightly stained); that in 2 is stained with Vector-SG providing a blue/gray color; that in 3 is stained for alpha-fetoprotein with hematoxylin/eosin background. Specific sites within 5 C are numbered and correlate with enlargements that indicate the changes occurring within the lobules. The host liver lobules and acini are breaking down due to the wealth of MMPs flooding into the area along with the donor cells. The donor cells are observed at the boundary regions of the lobules, sites also demonstrating liver-specific markers such as HNF4-a and α-fetoprotein, meaning that the cells are maturing to a liver fate. These traits were not expressed by the BTSCs and so these are indications that the donor cells are undergoing maturation to an hepatic fate.

FIG. 6A is a low magnification (panoramic scan) image of GFP+ donor cells that have engrafted into much of the pancreas and into the submucosa of the duodenum (a region containing Brunner's Glands). Immunofluorescent staining of pig pancreas, liver, and duodenum in the site of the patch graft. GFP (green), Insulin (red), DAPI (blue). Donor-derived GFP+ cells occur in the proximity of the site where the patch graft was positioned, and appear integrated in the pancreas parenchyma. The silk mesh of the SERI surgical scaffold is observed interposed among pancreas, liver, and duodenum. FIG. 6B shows that donor cells mature to functional islets. At higher magnification, donor-derived GFP+/Insulin+beta cells (yellow—from merge of the GFP and of the red from staining for insulin) are observed intermingled with host GFP−/Insulin+(red) beta cells in the pancreas parenchyma. Surrounding the islet cells are a large number of GFP+ cells displaying a morphology consistent with that of pancreatic exocrine cells, including acinar and ductal cells. Supporting this interpretation are the findings in C and D that, indeed, these cells are producing amylase, a classic acinar marker. FIG. 6C and FIG. 6D show evidence of functional acinar cells derived from donor stem cells. Immunofluorescent staining of a serial section from the same tissue block in the site of the patch graft and with focus on the region of engrafted GFP+ donor cells. Amylase (green), Insulin (red), Glucagon (white—not visible in the panoramic scan in C, but visible at the higher magnification in D), DAPI (blue). Amylase+ acinar cells are the vast majority of the exocrine tissue of the pancreas. By comparing the staining presented in the serial sections at low and high magnifications, it is deduced that most of the donor-derived GFP+ cells in the pancreas have acquired an amylase+ acinar fate.

FIGS. 7A-7H offers a characterization of matrix-metalloproteinases (MMPs). MMPs are comprised of a large gene family of calcium-dependent, zinc-containing enzymes that dissolve extracellular matrix components. There are at least 24 isoforms known in pigs of which a subset are secreted factors (e.g. MMP1, MMP2, MMP7, MMP9) and a subset are membrane-associated (e.g. MMP14, MMP15). MMP1 was identified by IHC, especially in the areas of remodeling, but not by RNA-seq, since there has not yet been an annotated form of porcine MMP1 available for RNA seq analyses. FIG. 7A, FIG. 7B, FIG. 7C, and FIG. 7D show isoforms of secreted and membrane-associated categories were expressed by both stem/progenitors and mature cells. Quantitation of the expression levels indicated that the membrane-associated forms were similar for both stem/progenitors and mature cells (note the comparisons in FIG. 7D). By contrast, secreted forms were expressed at very high levels in stem/progenitors and at low or negligible levels in mature cell types. The cell populations of adult cells analyzed were isolated from suspensions of piglet livers and biliary tree tissue and comprised of CD45+ cells (hemopoietic cells), CD146+ cells (stellate cells), CD31+ cells (endothelia), EpCAM+/CD45− cells (adult diploid hepatocytes and cholangiocytes. These EpCAM+/CD45− cells are the mature parenchymal cells found in piglet livers. The BTSCs were isolated from the biliary tree by the protocols given in the examples. FIG. 7E shows representative MMP expression in regions of remodeling with a BTSC/ELSMCs graft. In a section adjacent to the patch graft of BTSCs/ELSMCs were stained with Trichrome indicating the region (bracket) of remodeling. The region appears as linear stripes of red and blue being cells and matrix components undergoing dissolution by the "sea" of MMPs. The stripes end at the edges of lobules that are still mostly intact but beginning to "fray" at their boundaries from the effects of the MMPs derived from the invading cells. FIG. 7F shows representative images of IHC assays for MMP1 (Novo-red+). Methyl green is the background stain. The liver's lobular/acinar structure has dissolved into the undulating swirls of cells and marked by the strong expression of MMP1, a secreted isoform of MMPs. FIG. 7G shows a section stained for MMP2 (Novo-red+). Hematoxylin is the background stain. The liver's lobular/acinar structure has disappeared and has been replaced by a mix of cells with strong staining for MMP2 (rust brown color). FIG. 7H shows the remodeling process ongoing within the liver lobules. The liver lobules have become strips of cells interspersed by invading cells; MMP2+ expression (rust colored) is very high and contributing to the loss of lobular/acinar structures. With clearance of hyaluronans (by 2-3 weeks), the lobular structures reappeared.

FIG. 8 is a schematic demonstration of the engraftment and integration phenomena in liver and on pancreas.

FIG. 9A (Panels (a)-(b)) shows Trichrome staining of normal pig liver. Bar is 200 µm for low magnification image (a) and 50 µm for the higher magnification image (b). Note the collagens in the Glisson capsule and the boundaries between hepatic acini. FIG. 9B (Panels (a)-(b)) shows Trichrome staining of patch graft of normal, adult hepatocytes partnered with mature mesenchymal cells (MMCs), endothelia and stellate cells, did not engraft. In the low magnification image (a) note that the Glisson capsule is intact, and cells remain atop the capsule. (b) at the higher magnification, there is evidence of some remodeling (plasticity phenomena) of cells in the lobule next to the graft (the mottled red color within the hepatocytes). This plasticity is assumed due to the membrane-associated MMPs known to be present on both stem cells and adult cells. FIG. 9C (Panels (a)-(c)) shows IHC assays on patch graft of normal, adult hepatocytes partnered with mature mesenchymal cells (MMCs). At the higher magnification (a), it is evident that engraftment has not occurred. This section was stained with antibody to RBMY-1 and with hematoxylin as the counterstain (b). The Glisson capsule is intact and so are the boundary zones between lobules, and (c) negative control (staining without primary antibody) to indicate non-specific staining. FIG. 9D (Panels (a)-(c)) shows Trichrome staining of patch graft of normal, adult hepatocytes partnered with ELSMCs that here were porcine mesenchymal stem cells (MSCs) played the role of a cellular source of MMPs. The graft is separating at the interface between the graft and the host tissue. The bracket indicates the region of remodeling. Note that the liver lobules have lost the matrix that normally constitutes boundary zones between them and appear frayed at the edges. In the higher magnification (a) are seen donor cells (pale red compared with the dark red ones in the centers of the lobules) throughout the image; in (b) is an enlargement of a region showing that the Glisson capsule is considerably thinner under the patch (compare with region to the left of the box) and in (c). Extensive remodeling was evident in the cells adjacent to the graft (c). FIG. 9E (Panels (a)-(d)) shows a patch graft of hepatocytes partnered with ELSMCs (porcine MSCs) after one week. The section (a) was stained with antibody to RBMY-1 (brown) and with methyl green as the counter stain. The donor cells engrafted (regions of rust red color) and matured into adult parenchymal cells in the acini near to the graft. The section (b) shows an enlargement of the image near to the remains of the thinned Glisson capsule showed that donor cells (dark brown nuclei) were interspersed uniformly with host cells (nuclei were methyl green color). The section (c) is the negative control for (b). The section (d) was stained with antibody to GFP (coupled with Novus red and yielding a rust brown color) and with methyl green as the counter stain. Most of the cells have engrafted and formed a band of dark red, donor (mature) hepatocytes within the host liver acini. The Glisson capsule remained but was diminished in thickness. Migration much beyond the region of the liver near to the graft was not observed within the three-week time-frame of the experiments.

FIG. 10 is a schematic comparing engraftment of stem cells versus adult cells.

FIG. 11 shows evidence that the engraftment process involves migration of cells to considerable distances within the host tissue. Here is demonstrated that for grafts of BTSCs/ELSMCs organoids at one week post-transplantation. The schematic of the liver divided into 8 different zones is used to indicate the regions evaluated for the presence of donor cells. Sections are prepared from the regions 1-8 and then stained to enable identification of donor cells. In the table are summarized the findings showing the distances between the graft and each region and the proportion of GFP+ cells found. The images to the left of the table are scans of a representative section from each zone. The dark brown staining is strongest in 6 near to the graft and is fainter with increasing distance from the graft, the palest being zone 1.

FIGS. 12A-12E provides evidence for migration of donor cells throughout the host liver. GFP+ cells stained with Novo-red (rust brown color); host cells are stained with methyl green. FIG. 12A (Panels (a)-(b)) is a low magnification image of interface of graft and the host liver. The separation of the graft from the host liver was often seen (note this also in FIG. 3) and was shown correlated with exceptionally high levels of secreted MMPs. Enlargement of the regions (a) and (b) are given below. Note the areas in the low magnification image and in the enlargement in (b) in which staining is mottled and with areas showing a washed out appearance and that proved due to hyaluronan levels in the tissue. FIG. 12B depicts the intermediate zones to which the cells migrated. Donor cells are throughout the tissue, both in bile ducts and in the parenchyma of the acini. FIG. 12C shows the distance zones to which the cells migrated. Note that only the bile ducts are stained. FIG. 12D provides enlargements showing donor cells in bile ducts. FIG. 12E provides enlargements within the parenchyma to show that the donor cells have GFP labeling in the nuclei.

FIGS. 13A-13D shows the adverse conditions obtained for patch grafts with certain backings (see also Tables 1 and 2). These included necrosis, adhesions, and sites of cholestasis found to occur when grafts were placed too close to some ducts such that the swelling caused occlusion of the ducts.

FIG. 14 shows a chart of both lineage stages for epithelial cells (FIG. 14A) and mesenchymal cells (FIG. 14B) and the corresponding biomarker profiles.

BRIEF DESCRIPTION OF THE TABLES

Figure 2F:

TABLE 1 provides a summary of surgical or other approaches for patch grafting.

TABLE 2 provides a comparison of backings tested for the exemplary patch grafts.

TABLE 3 provides a summary of the antibodies used for IHC and IF in the examples.

TABLE 4 provides a summary of the primers (SEQ ID NOS 1-28, respectively, in order of appearance) used for qRT-PCR assays.

DETAILED DESCRIPTION

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting of the invention. All publications, patent applications, patents and other references mentioned herein are incorporated by reference in their entirety.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2012) *Molecular Cloning: A Laboratory Manual*, 4rd edition; the series Ausubel et al. eds. (2012) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (2014) *Antibodies, A Laboratory Manual*, 2d edition; Freshney (2011) *Culture of Animal Cells: A Manual of Basic Technique*, 6th edition; Gait ed. (1984) *Oligonucleotide Synthesis*; U.S. Pat. No. 4,683,195; Hames and Higgins eds. (1985) *Nucleic Acid Hybridization*; Anderson (1999) Nucleic Acid Hybridization; Hames and Higgins eds. (1984) *Transcription and Translation; Immobilized Cells and Enzymes* (IRL Press (1986)); Perbal (1984) *A Practical Guide to Molecular Cloning*, Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It also is to be understood, although not always explicitly stated, that the reagents described herein are merely exemplary and that equivalents of such are known in the art.

Definitions

As used in the description of the invention and the appended claims, the singular forms "a," "an" and "the" are intended to include the plural forms as well, unless the context clearly indicates otherwise.

The term "about," as used herein when referring to a measurable value such as an amount or concentration (e.g., the percentage of collagen in the total proteins in the biomatrix scaffold) and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

As used herein, the term "patch graft" refers to a composition of cells embedded or comprised in an appropriate biomaterial that allows for transplanting donor cells (allogeneic or autologous) to the host. In some embodiments, the term refers to a composition of cells embedded or comprised in an appropriate biomaterial that allows for transplanting donor cells to the host. Biomaterials are ones that can be prepared under defined conditions (e.g., a basal medium optionally supplemented and/or a medium of nutritional factors, vitamins, amino acids, carbohydrates, minerals, insulin, transferrin/Fe, and/or lipids (purified free fatty acids complexed with purified albumin plus a lipoprotein carrier molecule such as high density lipoprotein)) and comprised, optionally solidified, into a soft gel (under 200 Pa, optionally approximately 100 Pa), and covered with a backing that has sufficient tensile strength to enable surgical attachment or otherwise tethered to a tissue or organ of the host and yet be of a chemistry with minimal effects on the differentiation of the donor cells. To be avoided are supplements with factors that might drive differentiation of the cells, especially the early lineage stage mesenchymal cells (ELSMCs); these include serum, growth factors and cytokines affecting ELSMCs, and mature matrix components (e.g. type I collagen).

The term "backing," as used herein, refers to a material that serves as a backing or barrier on the surface of the patch graft capable of tethering the graft to a target site and/or facilitating migration of the cells therein to the target site and/or preventing or inhibiting migration of the cells toward the backing. The backing is or comprises a "biodegradable, biocompatible material," "biocompatible, biodegradable material," or any variation thereof referring to a material which (i) is biocompatible with the subject into which it is being transplanted, (ii) exhibits mechanical resilience to withstand the compressive and shear forces that occur on organs and tissues (especially internal ones), which in turn enables this material to function as a surgical tissue, and (iii) has a neutral or minimal effect on the differentiation status of cells that come in contact with the material. In some embodiments, the backing of the patch graft comprises such a material. In such embodiments, the mechanical resilience of (ii) should be such that the backing can be tethered the graft to the target site. In further such embodiments, backing directs cell migration toward the target site—e.g. by affecting the differentiation of those cells migrating in directions away from the target site or by physically blocking said migration. In this regard, suitable materials include but are not limited to Seri-silk, optionally contour Seri-Silk, or derivatives thereof, aminions or extracts thereof (for example, of the side facing the fetus and/or a patch or textile comprised of PGA and/or PLLA. Non-limiting examples of suitable patches of synthetic materials include a woven patch comprised of 91% PGA-co-9% PLLA, a knit patch comprised of 91% PGA-co-9% PLLA, or a non-woven patch comprised of 100% PGA. More generally, suitable backings may include forms of *Bombyx* moth silk such as Seri$^R$ Surgical Silk Scaffolds (Sofregen, New York, N.Y.), other derivatives of *Bombyx* moth silk, and synthetic textiles, such as forms of Polyglycolic acid-co-poly-L-lactic acid (PGA/PLLA).

In some embodiments, the backing is also bioresorbable. As used herein, "bioresorbable" refers to a material that can be broken down by the body of a host or recipient of the graft and does not require mechanical removal. In some embodiments, the bioresorbable backing is bioresorbable within a span of about 2 to about 10 weeks, about 2 to about 20 weeks, about 2 to about 52 weeks, about 4 to about 16 weeks, about 4 to about 12 weeks, or about 4 to about 8 weeks. In some embodiments, the bioresorbable backing is bioresorbable within a span of about 4 to about 8 weeks; about 4 to about 12 weeks, about 4 to about 16 weeks, about 4 to about 20 weeks, and about 4 to about 52 weeks.

As used herein, the biomaterials of the graft, and independent of the backing, include ones that can form hydrogels. The term "gel" refers to a solid jelly-like material that can have properties ranging from soft and weak to hard and tough. Gels are defined as a substantially dilute cross-linked system, which exhibits no flow when in the steady-state. By weight, gels are mostly liquid, yet they behave like solids due to a three-dimensional cross-linked network within the liquid. It is the crosslinking within the fluid that gives a gel its structure (hardness, stiffness, mechanical, or viscoelasticity properties) and contributes to its adhesivity. In this way gels are a dispersion of molecules of a liquid within a solid in which the solid is the continuous phase and the liquid is the discontinuous phase. A "hydrogel," also referred to herein as a "hydrogel matrix," is a non-limiting example of a gel comprised of a macromolecular polymer gel constructed of a network of polymer chains. Hydrogels are synthesized from hydrophilic monomers or hydrophilic dimers (e.g. in the case of hyaluronan) by either chain or step growth, along with network formation. A net-like structure along with void imperfections enhance the hydrogel's ability to absorb large amounts of water via hydrogen bonding. As a result, hydrogels develop characteristic firm yet elastic mechanical properties. They are able to undergo spontaneous formation of new bonds when old bonds are broken within a material. The structure of the hydrogels along with electrostatic attraction forces drive new bond formation through non-covalent hydrogen bonding.

The biomaterials used for the grafts have mechanical properties, stiffness, that can be more rigorously defined as the viscoelasticity of the biomaterials. See https://en.wikipedia.org/wiki/Viscoelasticity. The graft biomaterials conducive to engraftment must be very soft (for example, about 100 Pa), conditions permissive for the donor cells to remain immature (Lozoya et al. Biomaterials 2011; 32 (30): 7389-7402.) and so be able to produce membrane-associated and/or secreted forms of MMPs.

As used herein, the term "viscoelasticity" refers to the property of materials that exhibit both viscous and elastic characteristics when undergoing deformation. Viscous materials, like honey, resist shear flow and strain linearly with time when a stress is applied. Elastic materials strain when stretched and quickly return to their original state once the stress is removed. Viscoelastic materials have elements of both of these properties and, as such, exhibit time-dependent strain. Whereas elasticity is usually the result of bond stretching along crystallographic planes in an ordered solid, viscosity is the result of the diffusion of atoms or molecules inside an amorphous material. Though there are many instruments that test the mechanical and viscoelastic response of materials, broadband viscoelastic spectroscopy (BVS) and resonant ultrasound spectroscopy (RUS) are more commonly used to test viscoelastic behavior because they can be used above and below ambient temperatures and are more specific to testing viscoelasticity. These two instruments employ a damping mechanism at various frequencies and time ranges with no appeal to time-temperature superposition. Using BVS and RUS to study the mechanical properties of materials is important to understanding how a material exhibiting viscoelasticity will perform As used herein, the term "hyaluronan," or "hyaluronic acid," refers to a polymer of disaccharide units comprised of glucosamine and glucuronic acid [1-3] linked by β1-4, β1-3 bonds and salts thereof. Thus, the term hyaluronan refers to both natural and synthetic forms of hyaluronans. The naturally occurring hyaluronan (HA), water-soluble polysaccharide comprising disaccharide units of D-glucuronic acid (GlcUA) and N-acetyl-D-glucosamine (GlcNAc), which are alternately linked, forming a linear polymer. High molecular weight HA may comprise 100 to 10,000 disaccharide units. HAs often occur naturally as the sodium salt, sodium hyaluronate. HA; sodium hyaluronate, and preparations of either HA or sodium hyaluronate are often referred to as "hyaluronan." Non-limiting examples of acceptable hyaluronate salts, include potassium hyaluronate, magnesium hyaluronate, and calcium hyaluronate.

Other glycosaminoglycans (GAGs) can also be used in the hydrogel. These include forms of chondroitin sulfate (CSs) and dermatan sulfates (DSs), polymers of glucuronic acid and galactosamine, and heparan sulfates (HSs) and heparins (HPs), polymers of glucuronic acid and glucosamine. The extent and pattern of sulfation of these GAGs are critical, since the sulfation patterns dictate the formation of complexes with multiple families of proteins (e.g. coagulation proteins, growth factors, cytokines, neutrophilic enzymes). See, e.g., Powell A K, Yates E A, Fernig D G, Turnbull J E. Interactions of heparin/heparan sulfate with proteins: appraisal of structural factors and experimental approaches. Glycobiology. 2004 April; 14(4): 17R-30R] Those appropriate for patch grafts that optimize engraftment comprise hyaluronans, non-sulfated GAGs, and ones with minimal sulfation such as forms of chondroitin sulfates found in stem cell niches, as shown in Karumbaiah L, et al. Chondroitin Sulfate Glycosaminoglycan Hydrogels Create Endogenous Niches for Neural Stem Cells. Bioconjug Chem. 2015 Dec. 16; 26(12):2336-49 and Hayes A J, et al. Chondroitin sulfate sulfation motifs as putative biomarkers for isolation of articular cartilage progenitor cells. J Histochem Cytochem. 2008 February; 56(2):125-38 (incorporated herein by reference).

As used herein, the term "cell" refers to one or more cells in the graft. The cells of the present disclosure are eukaryotic. In some embodiments, this cell is of animal origin, optionally from a human organ, and can be a stem cell, a mature somatic cell, progenitor cell, or intermediates in the lineage stages from the stem cells to the mature cells. The term "population of cells" or "cells" refers to a group of one or more cells of the same or different cell type with the same or different origin; this term is used interchangeably herein with the term "donor cells," which intend cells that may be autologous or allogeneic. In some embodiments, this population of cells may be derived from a cell line, from freshly isolated cells, or in some embodiments, this population of cells may be derived from a portion of an organ or tissue, optionally from a donor or a recipient.

The term "stem cell" refers to cell populations that can self-replicate (produce daughter cells identical to the parent cell) and that are multipotent, i.e. can give rise to more than one type of adult cell. The term "progenitor cell" or "precursor" as used herein, is broadly defined to encompass progeny of stem cells and their descendants. Progenitors are cell populations that can be multipotent, bipotent, or unipotent but have minimal (if any) ability to self-replicate. Committed progenitors are ones that are unipotent and can differentiate into a particular lineage leading to only one mature cell type. Non-limiting examples of stem cells include but are not limited to embryonic stem (ES) cells, induced pluripotent stem (iPS) cells, germ layer stem cells, determined stem cells, (ectodermal, mesodermal or endodermal), perinatal stem cells, amniotic fluid-derived stem cells, mesenchymal stem cells (MSCs), angioblasts, and those derived from umbilical cord, Wharton's jelly, and/or placenta. Intermediates between stem cells and committed progenitors include cell populations such as hepatoblasts and pancreatic ductal progenitors and other forms of transit amplifying cells that may be multipotent but have extensive proliferative potential but more limited (if any) self-replicative ability.

The term "mesenchymal cells" refers to cells derived from the mesenchyme, including but not limited to angioblasts, precursors to endothelia, precursors to stellate cells, endothelia, stellate cells, stromal cells, various subpopulations of mature and progenitor cells, and mesenchymal stem cells (MSCs) which are multipotent stromal cells and various subpopulations of mature and progenitor mesenchymal cells. The MSCs are cell populations prepared by culture selection processes from tissues (Cathery et al. Stem Cells 2018; PMID:29732653; Graceb et al. Biochimie 2018: PMID 29698670; Caplan A I. Stem Cells Int. 2015; PMID: 26273305. There are at least two major categories of mature mesenchymal cells: (a) Mature mesenchymal cells (stellate/stromal cells) that produce and are surrounded by forms of extracellular matrix that comprise fibrillar collagens (e.g. type I, III, V) and associated matrix components (fibronectins, chondroitin sulfate proteoglycans, dermatan sulfate proteoglycans) and bound signals (e.g. growth factors, cytokines) that form a complex and bound signals (e.g. growth factors/cytokines) that form a complex associated with cells that are typically linear (string-like) cell populations. Non-limiting examples of such cells include stellate cells, tendon, stroma, and myofibroblasts. (b) Mature mesenchymal cells such as endothelia that produce and are surrounded by forms of extracellular matrix that comprise network collagens (e.g. type IV, type VI, VIII, X) and associated matrix molecules (laminins, heparan sulfate proteoglycans, heparin proteoglycans) and bound signals (e.g. growth factors, cytokines) that together are associated with cells having more squamous or cuboidal or cobblestone morphologies. Nonlimiting examples of such cells include endothelia and myoepithelial.

The precursors to these mesenchymal cell types include but are not limited to angioblasts which are multipotent and that can differentiate into lineages of endothelia (the late stages of which are fenestrated endothelia) or stellate cells (the late stages of which are myofibroblasts (stroma). The precursors also include mesenchymal stem cells (MSCs) which are multipotent cells and can differentiate into fibroblasts (stroma), osteoblasts (bone cells), chondrocytes (cartilage cells), myocytes (muscle cells) and adipocytes (fat cells)). The MSCs may optionally be prepared by culture selection methods (Cathery et al. Stem Cells 2018; PMID: 29732653; Graceb et al. Biochimie 2018: PMID 29698670; Caplan A I. Stem Cells Int. 2015; PMID: 26273305.

The term "epithelial cell expansion" is correlated with the diameter of a colony of epithelial cells that typically form colonies with cuboidal or cobblestone morphologies and with estimates of growth being the composite of the diameters of the cells of the colony. By contrast, estimates of growth of mesenchymal cell colonies are correlated with the density of the colony, since the mesenchymal cells are more migratory and motile, and the colony density is a reflection of the net sum of cells that remain within the colony boundaries.

The term "epithelial cells" refers to cells derived from the epithelium, specialized cells that provide diverse functions for the tissue and/or the systemic needs of a host. They are recognized by their ability to migrate as precursors or immature cells; with maturation, they become stationary and form layers of squamous or cobblestone-like or columnar polarized cells with apical, basal and lateral sides, and that are bound to each other by an assortment of junctions (connexins, tight junctions, adherens). Their expansion potential is indicated by the diameter of a colony (not by its density). The mature epithelial cells provide diverse functions such as secretion of specialized products or contributions to metabolism (hepatocytes, cholangiocytes), detoxification (hepatocytes), production of enzymes (acinar cells), production of endocrine factors (e.g. islets or other endocrine cells)), electrical activity (neuronal cells), and absorption (intestinal cells).

The term "biliary tree stem cells" (BTSCs) refers to epithelial stem cells found throughout the biliary tree and located within peribiliary glands (PBGs), Brunner's Glands, both extramural and intramural, as well as within the crypts of gallbladder villi. They have the ability to transition into committed hepatic and/or pancreatic progenitor cells The hepatic descendants enter into the liver sinusoids via canals of Hering; the pancreatic progenitors are found within pancreatic duct glands (PDGs), regions of the biliary tree located within the pancreas.

Thus far, at least 7 subpopulations of stem cell populations have been identified with overlapping traits and ranging from extremely primitive BTSCs to stem cell populations definable as hepatic or pancreatic stem cells. Description of what is known for these is given below. The most primitive ones are found in both the extramuralperibiliary glands—ones tethered to the surface of the bile ducts—and; the intramural peribiliary glands—ones found within the bile duct walls. The intramural peribiliary glands (PBGs) near to the fibromuscular layer in the centers of the bile duct walls can also be considered crypts (with parallels to intestinal crypts), niches in which are found the most primitive stem cell populations. The largest numbers of the PBGs within the biliary tree network are found within the hepato-pancreatic common duct and within the large intrahepatic bile ducts. No PBGs occur in the gallbladder, and instead the stem cell niches within the gallbladder are the bottoms of the gall bladder villi that contain intermediate to late stage stem cell populations that are precursors to hepatic stem cells. The BTSCs are precursors to both liver and to pancreas. They give rise to hepatic stem cells, precursors to liver, and to pancreatic stem cells, precursors to pancreas, and these are found throughout the biliary tree but in numbers influenced by whether near to the liver versus the pancreas. Thus, small numbers of pancreatic stem cells and large numbers of hepatic stem cells are located in the PBGs of the large intrahepatic bile ducts, whereas small numbers of hepatic stem cells and large numbers of pancreatic stem cells are located in the PBGs of the hepato-pancreatic common duct.

Summaries of genetic signatures are presented in the Figures. In general, all of the BTSCs subpopulations express generic biomarkers that include endodermal transcription factors for both liver and pancreas (e.g. SOX9, SOX17, PDX1), pluripotency genes (e.g. OCT4, SOX2, NANOG, SALL4, KLF4/KLF5, BMI-1); one or more of the hyaluronan receptor isoforms (standard and/or variant isoforms) of CD44; CXCR4; and cytokeratins 8 and 18. Stem cell subpopulations within the biliary tree and PBGs include (1) Brunner's Glands stem cells in the submucosa of the duodenum and that express CK7, TRA-160 and 181 and with traits distinguishable from stem cells in the intestine; (2) early stage intramural Biliary Tree Stem Cell (BTSCs) that express sodium iodide symporter (NIS) and CXCR4, OCT4, SOX2, NANOG, but do not express LGR5 or EpCAM; (3) intermediate stage intramural BTSCs that express less of NIS but gain expression of LGR5 but not EpCAM; (4) late stage intramural BTSCs (the only BTSCs found in the gallbladder) and also found in high numbers in the large intrahepatic bile ducts and in the hepato-pancreatic common duct. They express both LGR5 and EpCAM. These are precursors to hepatic stem cells (in the liver and expressing SOX17 but not PDX1) and to the pancreatic stem cells (in the hepato-pancreatic common duct and expressing PDX1 but not SOX17); (5) hepatic stem cells may be found in the canals of Hering, in PBGs of the large intrahepatic bile ductules, in PBGs in the extrahepatic biliary tree; and in the PBGs of the hepato-pancreatic common duct, but the highest numbers are those at intrahepatic sites. The hepatic stem cells retain the ability to self-replicate and to be multipotent. The biomarkers for these cells include SOX9, SOX17, HNF-4 alpha, ITGB1 (CD29), ONECUT 2, SALL4, LGR5, CD44, epithelial cell adhesion molecule (EpCAM) found in the cytoplasm and at the plasma membrane, neural cell adhesion molecule (NCAM), CD133 (prominin), negligible levels (or none) of albumin, a complete absence of alpha-fetoprotein (AFP), an absence of P450 A7, and an absence of secretin receptor (SR). Hepatic stem cells and hepatoblasts express cytokeratins 8, 18 and 19; (6) pancreatic stem cells are found in small numbers throughout the biliary tree (even in the PBGs in the large intrahepatic bile ducts) but are found in high numbers in PBGs of the hepato-pancreatic common duct. They have the pluripotency genes and expression for the other genes noted for all of the stem cell populations, but they differ in no longer having SOX17; the subpopulations that will lineage restrict to islets express NGN3. They express EpCAM throughout the cells and at the plasma membrane and express low (or no) insulin. Maturation of them is correlated with increasing insulin expression as well as with expression of other islet hormones (e.g. glucagon). Those maturing into acinar populations will express MUC6 and amylase.

It is noted that hepatic and pancreatic stem cells may also be found in their respective source organs when they are early in development (e.g. as ESCs or otherwise), and that any of those cells disclosed herein may be alternatively generated through induction (i.e. as iPSCs).

As used herein, the term "supportive" is used to describe cells which are able to assist in the propagation of cells from another lineage stage or provide assistance to neighboring cells through the production of "paracrine signals", factors active in their effects on neighboring cells in terms of survival, expansion, migration, differentiation, and maturation. For example, supportive mesenchymal cells may be defined by their ability to influence epithelial cells, optionally through the secretion of matrix metallo-proteinases (MMPs) and/or one or more paracrine signals or growth factors. Many of these are summarized in recent reviews. (Cathery et al. Stem Cells 2018; PMID:29732653; Graceb et al. Biochimie 2018: PMID 29698670; Caplan A I. Stem Cells Int. 2015; PMID: 26273305.

The term "lineage stage partners" refers herein to mesenchymal cells and/or epithelial cells that are lineage stage appropriate to support engraftment of the cells. For the hepatic or biliary tree stem cells, these are comprised of angioblasts (CD117+, CD133+, VEGFr+, CD31-negative) and their immediate descendants, precursors to endothelia (CD133+, VEGFr+, CD31+, Van Wildebrand Factor (vWF+)) and precursors to stellate cells (CD146+, ICAM-1+, alpha-smooth muscle actin+ (ASMA), vitamin A-negative). They can be mimicked, in part and/or to some extent, by use of mesenchymal stem cells (MSCs), such as but not limited to ones derived from bone marrow or fat tissue. Not to be bound by theory, it is believed that such cells should be used immediately after isolation from tissue or after minimal passaging ideally under serum-free conditions. These cells are collectively referred to herein as early lineage stage mesenchymal cells (ELSMCs).

Intermediates in the lineage network are referred to as "transit amplifying cells," which are cells that can be bipotent (or multipotent), have considerable proliferative potential but demonstrate little (if any) true self-replication, have low to moderate (or even no) pluripotency gene expression, and express traits indicating commitment to an hepatic (e.g. albumin, alpha-fetoprotein) or a pancreatic (e.g. insulin, MUC6, amylase) fate. These include hepatoblasts (the network giving rise to liver) and pancreatic ductal progenitors (the network giving rise to pancreas).

As used herein, the term "pancreatic ductal progenitors" refers to bipotent cells found within pancreatic ductal glands (PDGs) within the pancreas and giving rise to acinar cells and islets. In our studies, we find that they express SOX9, PDX1, PTF1a, HNF1β, EpCAM, LGR5, ICAM-1, CD44, and subpopulations express NGN3 or MUC6 or amylase. They have been extensively characterized by others. See, e.g., Rezanejad H, Ouziel-Yahalom L, Keyzer C A, Sullivan B A, Hollister-Lock J, Li W C, Guo L, Deng S, Lei J, Markmann J, Bonner-Weir S. Heterogeneity of SOX9 and HNF1β is dynamic. Stem Cell Reports. 2018 Mar. 13; 10(3):725-738.

As used herein, the term "hepatoblasts" refers to bipotent hepatic cells that can give rise to hepatocytic and cholangiocytic lineages and are found in or adjacent to canals of Hering or in PBGs within the large intrahepatic bile ducts. They have an extraordinary ability to proliferate (that is expand) but with less ability (if any) to self-replicate relative to that observed in hepatic stem cells or BTSCs. These cells are characterized by a biomarker profile that overlaps with, but is distinct from, hepatic stem cells or biliary tree stem cells. They express SOX9, low (or even negligible) levels of SOX17, high levels of LGR5, HNF4-alpha, and EpCAM, found primarily at the plasma membrane, and expressing P450A7, cytokeratin 7, secretin receptor, consistent expression of albumin in all hepatoblasts, high levels of alpha-fetoprotein (AFP), intercellular adhesion molecule (ICAM-1) but no expression of NCAM, and negligible or no expression of pluripotency genes (e.g. SALL4, KL4/KLF5, OCT4, SOX2, NANOG).) and no expression of mature hepatic parenchymal markers (e.g. P450s such as P4503A).

As used herein the term "committed progenitor" refers to a unipotent progenitor cell that gives rise to a single cell type, e.g. a committed hepatocytic progenitor cell. In some embodiments, they do not express pluripotency genes. The committed hepatocytic progenitors are recognized by expression of albumin, AFP, glycogen, ICAM-1, various enzymes involved with glycogen synthesis, and the gap junction gene, connexin 28. These give rise to hepatocytes. A committed biliary (or cholangiocytic) progenitor gives rise to cholangiocytes and is recognized by expression of EpCAM, cytokeratins 7 and 19, aquaporins, CFTR (Cystic Fibrosis Transmembrane Conductance Regulator), and membrane pumps associated with production of bile. In some embodiments, a committed islet progenitor expresses insulin, glucagon, and other islet hormones albeit at low levels; with maturation the expression levels of the islet hormones increase but with particular cells expressing preferentially certain hormones.

As used herein, the term "aggregates" refers to a plurality of cells that are amassed together. The aggregates may vary in both size and shape or may be substantially uniform in size and/or shape. The cell aggregates used herein can be of various shapes, such as, for example, a sphere, a cylinder (preferably with equal height and diameter), or rod-like among others. Although other shaped aggregates may be used, in one embodiment of the disclosure, it is generally preferable that the cell aggregates be spherical or cylindrical. The term "non-aggregated" refers to individual, or single-celled, stem and/or progenitor cells or mature cells. In some embodiments, the compositions provided herein can comprise substantially aggregated cells, substantially non-aggregated cells, or a mixture thereof.

The term "organoid" refers herein to a particular cellular aggregate of donor epithelial cells with mesenchymal cells that is self-assembled by simple panning methods described herein. In some embodiments, the mesenchymal cells are supportive mesenchymal cells. In some embodiments, the organoids are formed after culturing on low attachment dishes and under serum-free, defined conditions tailored to the lineage stage(s) of the aggregated cells in suspension. Others prepare organoids utilizing particular matrix extracts, such as Matrigel. Indeed, this substance is known to be the industry standard. See Hindley et al. Dev. Biology 2016; 420:251-261. PMID:27364469. The conditions described in which these organoids are maintained will not work successfully for the use of these organoids in the patch grafts described in this invention. The factors, such as those found in Matrigel, will stop or substantially reduce the MMP production by the cells which is required for the success of these patch grafts. Moreover, Matrigel cannot be a components of conditions for cells to be used clinically in people or for veterinary purposes.

The term "culture" or "cell culture" means the maintenance of cells in an artificial, in vitro environment. A "cell culture system" is used herein to refer to culture conditions in which a population of cells may be grown ex vivo (outside of the body)

"Culture medium" is used herein to refer to a nutrient solution for the culturing, growth, or proliferation of cells. Culture medium may be characterized by functional properties such as, but not limited to, the ability to maintain cells in a particular state (e.g. a pluripotent state, a proliferative state, quiescent state, etc.), to mature cells—in some instances, specifically, to promote the differentiation of progenitor cells into cells of a particular lineage. Non-limiting examples of culture media are serum supplemented media (SSM) being any basal medium supplemented with serum at levels that are typically about 10% to about 20%/a. The serum can be autologous (the same species as the cells) or, more commonly, serum from animals that are routinely slaughtered for commercial purposes (e.g. chickens, cows, pigs, etc.). Notably, the present embodiments involving stem cells employ media that avoids incorporation of serum and/or serum components that drive differentiation. Kubota's medium, a serum-free medium designed for endodermal stem/progenitors and comprised of a basal medium (nutrients, amino acids, vitamins, salts, carbohydrates) with no copper, low calcium (<0.5 mM) and supplemented with selenium, zinc, insulin, transferrin, lipids but no cytokines or growth factors. Other media found supportive of stem cells might also be usable, but they must avoid any factors that cause the cells to differentiate, since the maturational process will result in muting of production of membrane-associate and/or secreted MMPs.

Basal media are buffers used for cell culture and are comprised of amino acids, sugars, lipids, vitamins, minerals, salts, trace elements, and various nutrients in compositions that mimic the chemical constituents of interstitial fluid around cells. In addition, cell culture media are usually comprised of basal media supplemented with a small percentage (typically 2-10%) serum. For the grafting technologies described herein, conditions are used to maintain the cells as stem cells or early progenitor cells and so there is an avoidance of serum or any of the typical supplements that might drive the cells towards a mature cell fate. In addition to the customary basal media, various nutritional supplements, lipids (mixture of free fatty acids complexed with albumin and carrier molecules such as high density lipoprotein). Only two hormone/growth factors are added: insulin needed for carbohydrate metabolism, and transferrin, needed as a Fe carrier for the polymerases. Kubota's medium, a serum-free medium designed for endodermal stem/progenitors is comprised of a basal medium (with no copped, low calcium (<0.5 mM) supplemented with zinc, selenium, insulin, transferrin, lipids but no cytokines or growth factors. Other growth factors and cytokines and especially serum are to be avoided since they will induce differentiation of the donor cells and, thereby, minimize the production of MMPs, which are required for the engraftment and migration processes.

"Kubota's Medium" as used herein refers to any medium containing no copper, calcium (<0.5 mM), selenium, zinc, insulin, transferrin/Fe, a mix of free fatty acids bound to purified albumin and, optionally, also high density lipoprotein (HDL). In some embodiments, Kubota's Medium comprises any medium (e.g., RPMI 1640 or DMEM-F12) with no copper, low calcium (e.g., 0.3 mM), ~$10^{-9}$ M selenium, ~0.1% bovine serum albumin or human serum albumin (highly purified and fatty acid free), ~4.5 mM nicotinamide, ~0.1 nM zinc sulfate heptahydrate, ~$10^{-8}$ M hydrocortisone (optional component used for hepatic but not pancreatic precursors), ~5 µg/ml transferrin/Fe, ~5 µg/ml insulin, ~10 µg/ml high density lipoprotein, and a mixture of purified free fatty acids that are added after binding them to purified serum albumin. The free fatty acid mixture consists of ~100 mM each of palmitic acid, palmitoleic acid, oleic acid, linoleic acid, linolenic acid, and stearic acid. Non-limiting, exemplary methods for the preparation of this media have been published elsewhere, e.g., Kubota H, Reid L M, *Proc. Nat. Acad. Scien.* (USA) 2000; 97:12132-12137, the disclosure of which is incorporated herein in its entirety by reference.

In some embodiments, the conditions of these patch grafts are, therefore, counter to the routine use of media supplemented with a small percentage (typically 2-10%) serum. Serum has long been added to provide requisite signaling molecules (hormones, growth factors, cytokines) needed to drive a biological process (e.g. proliferation, differentiation). In some embodiments, serum is not included to avoid differentiation of the cells and/or avoid inactivating or muting production of MMPs, especially the secreted forms.

As used herein the term "amount effective" or "effective amount" refers to an amount that is sufficient to treat disease states or conditions (e.g. liver or pancreatic diseases). An effective amount can be administered in one or more administrations, applications or dosages. Such delivery is dependent on a number of variables including the time period during which the individual dosage unit is to be used, the bioavailability of the composition, the route of administration, etc. It is understood, however, that specific amounts of the compositions for any particular patient depends upon a variety of factors including the activity of the specific agent employed, the age, body weight, general health, sex, and diet of the patient, the time of administration, the rate of excretion, the composition combination, severity of the particular disease (e.g. liver or pancreatic disease) being treated and form of administration.

The terms "equivalent" or "biological equivalent" are used interchangeably when referring to a particular molecule, biological, or cellular material and intend those having minimal homology while still maintaining desired structure or functionality.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample; further, the expression level of multiple genes can be determined to establish an expression profile for a particular sample.

As used herein, the term "functional" may be used to modify any molecule, biological, or cellular material to intend that it accomplishes a particular, specified effect.

The term "gene" as used herein is meant to broadly include any nucleic acid sequence transcribed into an RNA molecule, whether the RNA is coding (e.g., mRNA) or non-coding (e.g., ncRNA).

As used herein, the term "generate" and its equivalents (e.g. generating, generated, etc.) are used interchangeable with "produce" and its equivalents when referring to the method steps that bring the organoid of the instant disclosure into existence.

The term "isolated" as used herein refers to molecules or biologicals or cellular materials being substantially free from other materials.

The terms "nucleic acid," "polynucleotide," and "oligonucleotide" are used interchangeably and refer to a polymeric form of nucleotides of any length, either deoxyribonucleotides or ribonucleotides or analogs thereof. Polynucleotides can have any three dimensional (3D) structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double and single stranded molecules. Unless otherwise specified or required, any aspect of this technology that is a polynucleotide encompasses both the double stranded form and each of two complementary single stranded forms known or predicted to make up the double stranded form.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the term "subject" and "patient" are used interchangeably and are intended to mean any animal. In some embodiments, the subject may be a mammal. In some embodiments, the mammal is bovine, equine, porcine, canine, feline, simian, murine, human, or rat. In some embodiments, the subject is a human.

The term "tissue" is used herein to refer to tissue of a living or deceased organism or any tissue derived from or designed to mimic a living or deceased organism. The tissue may be healthy, diseased, injured by trauma, damaged and/or have genetic mutations. The term "natural tissue" or "biological tissue" and variations thereof as used herein refer to the biological tissue as it exists in its natural state or in a state unmodified from when it was derived from an organism. A "micro-organ" refers to a segment of "bioengineered tissue" that mimics "natural tissue."

The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue. Exemplary tissues include, but are not limited to those derived from liver, pancreas, biliary tree, lung, intestines, thyroid, thymus thymus, bladder, kidneys, prostate, uterus, breast, skin and underlying dermal tissues, brain, spinal cord, blood vessels (e.g. aorta, iliac vein,), heart, muscle, including any combination thereof.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

ABBREVIATIONS

AFP, α-fetoprotein; ALB, albumin; BTSCs, biliary tree stem cells: CD, common determinant: CD44, hyaluronan receptors; CD133, prominin; CFTR, cystic fibrosis transmembrane conductance regulator; CK, cytokeratin protein: CXCR4, CXC-chemokine receptor 4 (also called fusin or CD184: also called platelet factor 4; EGF, epidermal growth factor; ELSMCs, early lineage stage mesenchymal cells, consisting of angioblasts and their descendants, precursors to endothelia and to stellate cells; EpCAM, epithelial cell adhesion molecule; FGF, fibroblast growth factor; HBs, hepatoblasts; HGF, hepatocyte growth factor; HpSCs, hepatic stem cells: KM, Kubota's Medium, a serum-free medium designed for endodermal stem cells; KRT, cytokeratin gene; LGR5, Leucine-rich repeat-containing G-protein coupled receptor 5 that binds to R-spondin; MMPs, matrix metallo-proteinases, a large family of proteinases associated with dissolution of extracellular matrix, with cell migration and with regenerative responses; NANOG, a transcription factor critically involved with self-renewal; NCAM, neural cell adhesion molecule; NIS, sodium/iodide symporter; OCT4, (octamer-binding transcription factor 4) also known as POU5F1 (POU domain, class 5, transcription factor 1), a gene expressed by stem cells; PDX1, pancreatic and duodenal homeobox 1, a transcsription factor critical for pancreatic development: PBGs, peribiliary glands, stem cell niches for biliary tree stem cells; SALL4, Sal-like protein 4 found to be important for self-replication of stem cells; SOX, Sry-related HMG box; SOX2, a transcription factor that is essential for maintaining self-renewal, or pluripotency in embryonic and determined stem cells. SOX9, transcription factor associated with endodermal tissues (liver, gut and pancreas; SOX17, a transcription factor essential for differentiation of liver; VEGF, vascular endothelial cell growth factor; vWF, Von Willebrand Factor.

Modes of Practicing the Present Disclosure

In the examples provided herein, Applicants establish patch grafting, a novel method for transplantation of cells into internal organs with design features dependent on whether cells are stem cells or mature cells. Applicants demonstrate these methods herein with grafts of biliary tree stem cells (BTSCs), precursors to both liver and pancreas, and transplanted onto liver or pancreas. The hosts used for developing these methods are breeds of swine, Sus scrofa domestics. They are major animal species used in translational research, surgical models, and procedural training and are used increasingly as alternatives to monkeys in preclinical studies.

Exemplary success was achieved with organoids of biliary tree stem cells (BTSCs), precursors to liver and to pancreas, partnered with early lineage stage mesenchymal cells (ELSMCs), and comprised in soft (~100 Pa) hyaluronan (HA) hydrogels. HA hydrogels, containing organoids, were placed onto Seri-silk backings (a mesh material) impregnated on their serosal sides with more rigid HA hydrogel (~700 Pa), and were surgically or otherwise tethered to the surface of the liver or pancreas. Within a week, grafts caused remodeling of organ capsules and adjacent tissue and, optionally, distant parenchymal tissue followed by a merger of donor and host cells. By two weeks, donor cells had matured to functional adult fates such as hepatocytes (albumin) or islets (β-cells-insulin). By three weeks, with clearance of HAs, organ capsules and normal tissue histology returned. The engraftment/migration/integration processes proved dependent on multiple plasma membrane-associated and secreted matrix-metallo-proteinases expressed by the cells.

These results of these examples are in contrast to those from past efforts to transplant cells from solid organs into internal organs, in which transplantation was accomplished either by direct injection or by delivering cells via a vascular route (see reviews by Bhatia et al., Lanzoni et al., Weber, and others). The past methods of transplantation result in small numbers of cells being engrafted, in risks of emboli that can be life threatening, and in significant levels of ectopic cell distribution. These problems have caused cell therapies for internal solid organs to be used minimally or not at all.

The patch graft strategy offers an alternative method for cell therapies, ones that can enable the delivery of adequate cell numbers and of their integration into the tissue to offer significant restoration of function(s). The examples demonstrate safety so long as biomaterials and the backing used were supportive of maintenance of some or all of the donor cells as immature and so able to produce the relevant repertoire of MMPs. A common source of failure was any factor(s) resulting in differentiation of the donor cells. Not to be bound by theory, it is contemplated herein that purified MMPs may be incorporated into graft biomaterials and/or cells may be transformed to secrete MMPs using a recombinant expression system or other genetic modification technique, as an alternative to providing a cells in the graft which naturally produce the requisite MMPs. In such embodiments, the combination of MMPs incorporated or transduced via construct should include those identified in the expression profiles provided in the examples below.

Composition of a Patch Graft

Aspects disclosed herein relate to a patch graft comprising a layer comprising a single population or two or more populations of cells (e.g. donor cells which may be autologous or allogeneic) and a source of MMPs and a backing comprising a biocompatible, biodegradable material, which may be used to tether the graft to a target site. In some embodiments, the population or populations of cells include a population of epithelial cells and a population of mesenchymal cells. In some embodiments, the populations of cells must be maintained in a particular state or "lineage stage" as part of the graft, meaning that they do not differentiate or mature further until incorporation into the organ. This can be achieved by balancing variables relating to the cell source, MMP content, medium used, and backing qualities. Each of these aspects is described in greater detail herein below.

Not to be bound by theory, it is believed that patch grafts can be successful with (1) an optimal cell population or mixture of cells—e.g. donor epithelial cells and a supporting mesenchymal stem/progenitor cell population that generates membrane-associated and/or secreted MMPs—in a medium and hydrogel that does not lead to differentiation of the supporting mesenchymal stem/progenitor cell population or that otherwise contains appropriate MMPs, and (2) a backing suitable to tether the graft to the target site and prevent migration of the cells in the graft toward the backing, away from the target site.

Exemplary Cells

Not to be bound by theory, the cells may be at any maturational lineage stage including embryonic stem (ES) cells, induced pluripotent stem (iPS) cells, determined stem cells, committed progenitors, transit amplifying cells, or mature cells. However, in certain embodiments, a source of MMPs must be present in the patch graft. Thus, contemplated herein are cellular sources of the MMPs for use in the patch grafts. Such cellular sources must be at an early lineage stage that is capable of expressing membrane-associated and/or secreted matrix metalloproteinases. An non-limiting example of such an early lineage stage are early lineage stage mesenchymal stem cells (ESMLCs).

In some embodiments, the cells to be grafted are epithelial cells partnered with mesenchymal cells. In some embodiments, the epithelial cells comprise epithelial stem cells. In some embodiments, the epithelial cells comprise committed and/or mature epithelial cells. In some embodiments, the committed and/or mature epithelial cells comprise mature parenchymal cells. In some embodiments, the mature parenchymal cells comprise one or more of hepatocytes, cholangiocytes, or islet cells. In some embodiments, the mesenchymal cells comprise ELSMCs. In some embodiments, the ELSMCs comprise one or more of angioblasts, precursors to endothelia, precursors to stellate cells, and MSCs. In some embodiments, the epithelial cells and mesenchymal cells are lineage stage partners of one another. In some embodiments, the epithelial cells and the mesenchymal cells are not lineage stage partners of one another, e.g. are not at approximately the same lineage stage or maturation stage, respectively. In some embodiments, the epithelial cells are mature cells. In some embodiments, the mesenchymal cells are ELSMCs.

In some embodiments, at least one of the epithelial cells and the mesenchymal cells are derived from a donor. In some embodiments, the donor is a subject in need of a tissue transplant. In some embodiments, the donor is the source of healthy cells for a tissue transplant. In some embodiments, at least one of the epithelial cells and the mesenchymal cells are autologous to an intended recipient of the patch graft. In some embodiments, all of the cells (i.e. epithelial and mesenchymal) are autologous to the intended recipient of the graft. In some embodiments, the donor of cells may be one other than the recipient (allograft) or may also be the subject (autologous) having the internal organ in a diseased or dysfunctional condition, optionally, wherein are obtained from a portion of the internal organ that is not diseased or dysfunctional and/or that the cells have been genetically modified to restore function.

In another aspect, the mesenchymal cells are lineage-stage partners of the donor cells, e.g. at a comparable or corresponding lineage stage. In another aspect, the mesenchymal cells are not lineage-stage appropriate partners of the donor cells. The mesenchymal lineage stage cells may be angioblasts, early lineage stage precursors to endothelia and/or stellate cells, mesenchymal stem cells, endothelia or stellate cells, or derivatives of these cell populations.

For stem cell transplants, epithelial cells should be partnered with their native, lineage stage partner mesenchymal cells (angioblasts and/or precursors to endothelia or to stellate cells). For adult epithelial cells, appropriate partners include early lineage stage mesenchymal cells (ELSMCs) that are comprised of angioblasts and/or precursors to stellate cells and to endothelial cells. Applicants have shown that one can use preparations of mesenchymal stem cells (MSCs) in combination with adult cells to achieve engraftment. In some embodiments, certain MSCs may be preferable to others. Not to be bound by theory, it is believed that grafts may be optimized by selecting combinations of cells which require minimal, if any culturing of the cells and that will avoid serum and matrix components that might drive differentiation of the cells.

Not to be bound by theory, it is further understood that the epithelial-mesenchymal relationship is important, since the paracrine signaling supports the production of MMPs. However, mature epithelial cells partnered with mature endothelia will survive in the graft and will be functional cells but will not engraft. Thus, if the mature epithelial cells are partnered with mature stroma to form a graft, the resulting grafts are likely to become fibrotic.

For treatment of a diseased or dysfunctional organ, cells may be from a donor other than the recipient (allografts) or may also be autologous transplants and so from the subject having the internal organ in a diseased or dysfunctional condition, optionally, wherein are obtained from a portion of the internal organ that is not diseased or dysfunctional and/or that the cells have been genetically modified to restore function.

For establishing a model system to study a disease, cells can be ones that have the disease and that are transplanted onto/into normal tissue in an experimental host.

In some embodiments, the epithelial cells may be stem cells combined with supportive mesenchymal cells, optionally ELSMCs, to form organoids, which optionally self-assemble. These organoids may be embedded or comprised in a hyaluronan hydrogel. The stem and/or progenitor cells of the present disclosure can include any stem and/or progenitor cell known in the art, including for example, an embryonic stem cell (ESC), an embryonic germ cell (EGC), an induced pluripotent stem cell (iPSC), a pancreatic stem cell (PSC), hepatic stem cell (HpSC), biliary tree stem cell (BTSC), an hepatoblast, a pancreatic ductal progenitor, a committed pancreatic progenitor cell, or a committed hepatic progenitor cell. In some embodiments, the cell populations comprise only stem cells such as pancreatic stem cells, hepatic stem cells, biliary tree stem cells (BTSCs) or Brunner's Glands stem cells. In other embodiments, the cells comprise only multipotent progenitor subpopulations such as hepatoblasts or pancreatic ductal progenitor cells, or the graft can contain committed, unipotent progenitors (e.g. hepatocytic or biliary or islet or acinar committed progenitor cells). In other embodiments, the cells comprise a mixture of stem cells and progenitors.

If adult epithelial cells are used, then they may be mixed at relevant ratios with ELSMCs into the grafting biomaterials. The ratios of cell mixture may be determined so as to mimic the target tissue. Alternatively or in addition, the ratios may be determined through self-assembly of the organoids. The organoids or cell mixtures are embedded in the soft grafting biomaterials such as the soft hyaluronan hydrogel. If a stem cell graft, then the stem and/or progenitor cells of the present disclosure can include any stem and/or progenitor cell known in the art, including for example, an embryonic stem cell (ESC), an embryonic germ cell (EGC), an induced pluripotent stem cell (iPSC), a Brunner's Glands stem cells (BGSCs), a biliary tree stem cell (BTSC), a pancreatic stem cell (PSC), an hepatic stem cell (HpSC), transit amplifying cells (e.g. hepatoblasts or pancreatic ductal progenitors), and committed, unipotent progenitors (e.g. a committed pancreatic progenitors or hepatocytic or cholangiocytic progenitor). In some embodiments, the cell populations comprise only stem cells. In other embodiments, the cells comprise only progenitor subpopulations. In other embodiments, the cells comprise a mixture of stem cells and progenitors or a mixture of stem/progenitor cells and more mature cells. In yet others, there can be a chimeric mix of adult cells (e.g. hepatocytes, cholangiocytes, enterocytes, islets) and ELSMCs.

The stem cell and/or progenitor cells can be identified by any method known to one who is skilled in the art. Non-limiting examples include using a combination of assays defining self-replicative ability and ones demonstrating multipotency by morphological analysis, by gene and/or protein expression, cell surface markers, and the like. In some embodiments, the stem and/or progenitor cells express at least one marker indicative of early stage liver cell lineage cell (e.g., SOX 17, HNF-4alpha, HNF6, HES1, CK19,) and at least one marker indicative of early stage pancreatic cell lineage (e.g., PDX1, PROX1, NGN3, HNFβ1). For example, stem and/or progenitor cells, in particular BTSCs, can be identified by expression of SOX9, SOX17, PDX1, CD133, NCAM, sonic hedgehog (SHH), sodium iodide symporter (NIS), LGR5, LGR6, EpCAM, various isoforms of CD44, CXCR4, and various pluripotency genes (e.g. OCT4, SOX2, NANOG, KLF4, KLF5, SALL4, BMi-1) or any combination thereof.

In some embodiments, the stem and/or progenitor cells express at least one marker indicative of early parental stage cell lineages such as parental lineages for liver and pancreas. Thus they would express one(s) shared by both hepatic and pancreatic lineages (e.g. SOX9, LGR5/LGR6, EpCAM, CD133, CK19) and one(s) for hepatic lineages (e.g., SOX 17, HNF-4-alpha, HNF6, HES1) and one(s) for early stage pancreatic cell lineages (e.g., PDX1, PROX1, NGN3, HNFβ1). For example, stem and/or progenitor cells, in particular BTSCs, can be identified by expression of SOX9, SOX17, PDX1, CD133, NCAM, sonic hedgehog (SHH), sodium iodide symporter (NIS), LGR5, LGR6, EpCAM, and various pluripotency genes (e.g. OCT4, SOX2, NANOG, KLF4, KLF5, SALL4, BMi-1) or any combination thereof.

Generation of Mature Cell Types

The stem and/or progenitor cells can also be differentiated into a more mature cell type, if one is desired. This can be done in vitro by spontaneous differentiation and/or by directed differentiation. Directed differentiation can involve use of a defined media, genetically modifying the stem and/or progenitor cells to express a gene of interest, or combinations thereof.

Non-limiting examples of defined media to differentiate cells include the hormonally-defined media (HDM) used for differentiation of endodermal stem cells to adult fates. Supplements can be added to Kubota's Medium to generate a serum-free, hormonally defined medium (HDM) that will facilitate differentiation of the normal hepatic or biliary tree stem cells to specific adult fates. These include supplementation with calcium to achieve at or above 0.6 mM concentration, 1 nM tri-iodothyronine (T3), $10^{-12}$ M copper, 10 nM of hydrocortisone and 20 ng/ml of basic fibroblast growth factor (bFGF). The medium conditions over and above these needed to selectively yield hepatocytes (HDM-H) versus cholangiocytes (HDM-C) versus pancreatic islets (HDM-P) are:
1) HDM-H: supplementation further with 7 μg/L glucagon, 2 g/L galactose, 10 ng/ml epidermal growth factor (EGF) and 20 ng/ml hepatocyte growth factor (HGF);
2) HDM-C: supplementation further with 20 ng/ml vascular endothelial cell growth factor (VEGF) and 10 ng/ml HGF; and
3) HDM-P: prepared without glucocorticoids and further supplemented with 1% B27, 0.1 mM ascorbic acid, 0.25 μM cyclopamine, 1 μM retinoic acid, 20 ng/ml of FGF-7 for 4 days, then changed with one supplemented with 50 ng/ml exendin-4 and 20 ng/ml of HGF for 6 more days of induction.

The HDM provided herein can be supplemented with additional growth factors including, but not limited to, Wnt signals, epidermal growth factors (EGFs), fibroblast growth factors (FGFs), hepatocyte growth factors (HGFs), insulin-like growth factors (IGFs), transforming growth factors (TGFs), nerve growth factors (NGFs), neurotrophic factors, various interleukins, leukemia inhibitory factors (LIFs), vascular endothelial cell growth factors (VEGFs), platelet-derived growth factors (PDGFs), stem cell factors (SCFs), colony stimulating factors (CSFs), GM-CSFs, erythropoietin, thrombopoietin, heparin binding growth factors, IGF binding proteins, and/or to placental growth factors.

The HDM provided herein can be supplemented with cytokines including, but not limited to interleukins, lymphokines, monokines, colony stimulating factors, chemokines, interferons and tumor necrosis factor (TNF).

Applicants have shown that hyaluronans can influence stem and/or progenitor cells to express factors that regulate critical cell adhesion molecules needed for cell attachment and cell-cell interactions and to prevent the stem and/or progenitor cells from internalization of those attachment factors following cell suspension preparations, cryopreservation, or with transplantation. Non-limiting examples of such attachment factors include integrins. Integrins are a large family of heterodimeric transmembrane glycoproteins that function to attach cells to extracellular matrix proteins of the basement membrane, ligands on other cells, and soluble ligands. Integrins contain a large and small subunit, referred to as α and β, respectively. This subunits form αβ heterodimers and at least 18α and eight β subunits are known in humans, generating 24 heterodimers. In some embodiments, the stem and/or progenitor cells express higher levels of integrin subunits, for example, ITGα1, ITGα2, ITGα2B, ITGα3, ITGα4, ITGα5, ITGα6, ITGα7, ITGα8, ITGα9, ITGα10, ITGα11, ITGαD, ITGαE, ITGαL, ITGαM, ITGαV, ITGαX, ITGβ1, ITGβ2, ITGβ3, ITGβ4, ITGβ5, ITGβ6, ITGβ7 and ITGβ8. In one preferred embodiment, the stem and/or progenitor cells express higher levels of integrin subunit beta 1 (ITGβ1) and/or integrin subunit beta 4 (ITGβ4). Takada Y. et al. (2007) *Genome Biol.* 8(5): 215.

In some embodiments, the stem and/or progenitor cells of the present disclosure differ from naturally occurring stem and/or progenitor cells at least in that they express an integrin subunit in an amount that is at least 10%, 15%, 20%, 25%, 30%, 35%, 40%, 45%, 50%, 55%, 60%, 65%, 70%, 75%, 80%, 85%, 90%, 95%, 100%, 200% greater than the amount of the integrin subunit in unmodified stem and/or progenitor cells. It is contemplated that an increase in an integrin subunit can help the stem and/or progenitor cell to attach, form cell-cell interactions, and to prevent the stem and/or progenitor cells from internalization should this be desired.

MMPs

The MMPs are one of the key factors facilitating engraftment and integration. MMPs are comprised of many isoforms (at least 28; in the pigs, 24 isoforms are known) of which some are secreted (e.g. MMP1, MMP2, MMP7, MMP9) and some are plasma membrane associated (e.g. MMP14, MMP15). Not to be bound by theory, it is believed that a mix of these is required for engraftment, especially a mix of the secreted forms. All cells examined produce varying amounts of both secreted and membrane associated forms, but stem/progenitors produce very high levels of the secreted forms. Engraftment is dependent on these secreted MMPs (and with some known synergies with the membrane-associated forms). A cellular source of these is the practical way to provide the requisite MMPs to achieve engraftment. As an alternative approach, Applicants contemplate incorporation of purified/recombinant forms of the MMPs into the graft biomaterials and/or genetic engineering of cells in the graft to produce the requisite MMPs.

The cells can successfully engraft as long as there are sources, ideally cellular sources, of multiple matrix metallo-proteinases (MMPs), optionally one or both of secreted and membrane-associated ones. MMPs are produced by all cell types, both immature and mature cells, but they vary as to which isoforms are produced and at what level of expression of particular MMPs. Representative secreted ones include MMP1, MMP2, MMP7 and MMP9. Representative membrane-associated ones include MMP14 and MMP15. Empirically it has been found that the highest production of secreted MMPs is by early lineage stage cells, stem cells and early progenitors. The biomaterials of the graft support the ability of both the epithelial and mesenchymal cells to produce these multiple forms of matrix metallo-proteinases (MMPs) that dissolve capsules around organs or tissues and enable migration of cells by means of dissolution of multiple forms of extracellular matrix components.

More generally, matrix metallo-proteinases (MMPS) are a large family of zinc-dependent proteinases that are involved in breakdown and modulation of extracellular matrix component and that are involved in implantation, invasion, angiogenesis, vascularization, and migration in normal and pathogenic processes. There are at least 28 isoforms that comprise matrixins, adamalysins, astacins, serralysins, etc. Their roles have been characterized in normal processes such as the implantation of the placenta, as well as in pathogenic ones such as invasion and metastases of cancers.

The studies described herein offer evidence for entirely new roles of MMPs that contribute to engraftment, migration and integration of transplanted cells. Stem/progenitors, both epithelial ones and mesenchymal ones, express multiple MMP isoforms that are especially potent in these roles. Maturation of the cells results in muting the expression of one or more of the potent stem/progenitor-cell-associated MMPs and so diminishing the invasion and migration processes. Adult cells also express MMPs, primarily ones that are membrane bound (MT-MMPs), said MMPs are involved in plasticity processes but not the wholesale engraftment and integration of cells into tissues. However, there are some synergies between the MT-MMPs and the secreted forms. The net sum of this realization is that the graft biomaterials, backing and other conditions must be ones that, among other characteristics, optimize expression of the various MMPs, such as the secreted MMPs, enabling the grafting and migration processes to occur. Therefore, factors driving differentiation of the transplanted cells will, in parallel, mute the complex MMP responses. This realization means that factors to be avoided include serum (which drives differentiation), soluble signals that drive differentiation (e.g. certain growth factors, cytokines and hormones); extracellular matrix components that drive differentiation (e.g. collagens, adhesion molecules, highly sulfated glycosaminoglycans/ proteoglycans); and mechanical forces contribute to rigidity (the viscoelasticity properties, which drive differentiation) of the graft.

In some embodiments, one or more of the cells in the mixture is a source of secreted and/or membrane-associated MMPs. The secreted MMPs may optionally be produced naturally by the one or more of the epithelial or mesenchymal cells or optionally be produced due to transformation of the one or more of the epithelial or mesenchymal cells with a recombinant expression vector or genetic editing for MMP production. In some embodiments, such as but not limited to those involving stem/progenitor cell populations that naturally secrete MMPs, variables that mute MMP expression— optionally membrane-associated and/or secreted MMP expression—are controlled in the patch graft. Non-limiting examples of such variables include variables that result in maturation of stem/progenitor cells, such as but not limited to serum supplementation to media or to the graft biomaterials, hormones or other soluble signals that influence differentiation of the epithelial and/or mesenchymal cells, oxygen levels (as anaerobic conditions keep the cells immature, whereas higher oxygen levels promote differentiation), and the rigidity of graft materials (as rigidity or mechanical forces such as shear force and compression may drive differentiation).

For stem cell grafts, both the epithelial cells and their mesenchymal cell partners are optimally stem cells or progenitors, since both provide contributions of multiple types of MMPs. To engraft adult cells, the one of the epithelial or mesenchymal cells should optimally provide a cellular source of membrane-associated and/or secreted MMPs, e.g. optionally using ELSMCs as the cellular source of membrane-associated and/or secreted MMPs. Thus, grafts in which both the epithelia and the mesenchymal cells are mature cell types are not successful for engraftment. If mature endothelia, then the epithelial cells are likely to survive and to proliferate and function but will not engraft; if mature stroma, then the grafts are likely to become fibrotic.

In summary, engraftment will occur if both epithelial-mesenchymal cell partners are stem/progenitors or if there at least one of the epithelial or mesenchymal cells is a stem cells, e.g. optionally using ELSMCs as a source of matrix-associated and/or secreted isoforms of matrix metalloproteases (MMPs), or if purified/recombinant forms of those MMPs are provided in the graft biomaterials. The early lineage stage mesenchymal cells (ELSMCs) appropriate for patch grafts can be angioblasts, precursors to endothelia, early lineage stage endothelia, precursors to stellate cells, early stage stellate cells, or mesenchymal stem cells (MSCs), or mixtures of these.

Thus, contemplated herein is a composition for use as a patch graft comprising at least a population of cells (e.g. epithelial and mesenchymal cells) and a source of MMPs (i.e. a population of cells at an early lineage stage that is capable of expressing membrane-associated and/or secreted matrix metalloproteinases (MMPs), optionally supported by the conditions of the medium and/or hydrogel.

Medium Components

For use in combination with the cells and source of MMPs disclosed herein, one can use any medium (comprising nutrients, vitamins, salts, etc.) plus critical soluble factors such as insulin, transferrin/Fe and lipids that is found useful for expansion and/or survival of stem/progenitors.

One must avoid all factors that cause the cells to mature, since maturation will result in a reduction or muting of expression of MMPs. The factors to be avoided include serum, soluble signals that drive differentiation, extracellular matrix components that drive differentiation, and rigidity or mechanical forces (compression, abrasion). A non-limiting example of such a media is Kubota's medium.

Thus, contemplated herein is a composition for use as a patch graft comprising at least a population of cells and a source of MMPs (e.g. a population of cells at an early lineage stage that is capable of expressing membrane-associated and/or secreted matrix metalloproteinases (MMPs), supported in a suitable medium, or purified MMPs). A non-limiting example of a suitable medium is Kubota's medium. Other stem cell mediums, such as those used for embryonic stem (ES) cells or induced pluripotent stem (iPS) cells may likewise be suitable as long as they do not contain soluble signals or matrix signals that will drive the differentiation of the cells that are the source of the MMPs or as long as MMPs are present or included from other sources.

Hydrogel

The patch graft comprises one or more hydrogel components. In some aspects, the biomaterials that can form hydrogels, or a parallel insoluble complex (e.g. a non-collagenous gelatin), comprise hyaluronans, thiol-modified hyaluronans, other glycosaminoglycans (GAGs), or combinations thereof. A trigger for solidification can be any factor eliciting cross-linking of the matrix components or gelation of those components that can gel. The cross-linker may comprise Poly(ethylene glycol) (PEG) or PEG-diacrylate (PEGDA) hydrogel or a disulfide-containing derivative thereof. Notably, biomaterials comprised in the hydrogel should be selected for the ability to support the stemness in the one or more cell populations disclosed for use in the patch graft, e.g. ELSMCs.

Matrix components supportive of maintenance of stemness can be used but not those components driving differentiation. Non-limiting examples of supportive components include hyaluronans or non-sulfated (or minimally-sulfated) glycosaminoglycans. These are especially useful since thy can be "tuned," that is modified to having varying levels of rigidity (optionally measured as viscoelasticity). Accordingly, in some aspects, the population of cells, optionally isolated cells of an internal organ, may be solidified ex vivo within the biomaterials prior to introducing the cells into the hosts, or in the alternative, injected as a fluid substance and allowed to solidify in vivo.

The very soft versions (e.g. ~100 Pa) of hydrogels are ideal for maintaining the donor cells in an immature state). More rigid versions (e.g. >500 Pa) can be used to cause the cells to mature enough to shut off MMP production and so block migration. More rigid versions can also minimize adhesions from neighboring tissues. In certain embodiments, the population of cells and the source of MMPs, optionally another population of cells (i.e. population of cells at an early lineage stage that is capable of expressing membrane-assocaited and/or secreted matrix metalloproteinases (MMPs)

Not to be bound by theory, it is believed that that forms of extracellular matrix found in amnions are able to keep the donor cells immature. Thus, amnions are contemplated both for use in the hydrogel and, optionally, as an alternative biocompatible, biodegradable material.

Notably materials known to cause maturation include certain components derived from mature extracellular matrix, such as but not limited to type I collagen. These materials should be excluded from all elements of the patch graft, including but not limited to the cells, the hydrogel, the medium, the backing, and/or any further components.

Thus, contemplated herein is a composition for use in the patch graft comprising at least a population of cells and a source of MMPs (i.e. a population of cells at an early lineage stage that is capable of expressing membrane-assocaited and/or secreted matrix metalloproteinases (MMPs), supported in a suitable medium and comprised in a hydrogel.

As noted above, rigidity can drive the ability of cells to differentiate. Further rigid hydrogels may have an effect on the ability of cells to migrate. As the cells must migrate into the organ, the hydrogel in which the cells are comprised should have a viscoelasticity sufficient to allow for migration of said cells, optionally, within or away from the hydrogel and/or the patch graft. Non-limiting examples of such viscoelasticity include by are not limited a viscoelasticity ranging from about 50 to about 100 Pa or about 250 Pa, for example at least about 50 Pa, at least about 100 Pa, at least about 150 Pa, at least about 200 Pa, at most about 250 Pa, at most about 200 Pa, at most about 150 Pa, at most about 100 Pa, and/or any individual value in between such as but not limited to about 50 Pa, about 100 Pa, about 150 Pa, about 200 Pa, and about 250 Pa.

Not to be bound by theory, it is believe that when the cells migrate from the patch graft into the target organ or tissue, they migrate with some of the hydrogel associated with them or coating them. The hydrogel shields the cells from the signals in the tissue microenvironment which would influence the cells to differentiate or mature, and enables the cells to remain immature. This facilitates the cells migrating through the parenchymal tissue. As the hyaluronans in the hydrogel gradually get degraded and removed, the cells begin to differentiate or mature and begin adult cell functions.

Methods of Generating Organoids

Not to be bound by theory, it has been determined that early stage lineage cells may have a high rate of graft success when incorporated into an organoid or an aggregate. Such organize may optionally comprise early lineage stages of both epithelial and of mesenchymal cells.

Thus, provided herein is a method of forming organoids, the method comprising, consisting of, or consisting essentially of culturing a mixture of epithelial cells and mesenchymal cells in a container suitable for tissue culture and in the presence of a culture medium, removing mature cells that attach to a surface of the container by panning, and recovering self-assembled organoids from the suspension of cells in the culture media. Also disclosed herein is a composition comprising an organoid generated as such.

In some embodiments, the procedure involves panning to eliminate mature cells by selective, rapid (15-30 minutes) attachment of them to regular culture dishes under serum-free conditions and at 37° C., since even under these conditions, the mature cells express various matrix components that enable cell attachment. Multiple rounds (e.g. 4-5) of such a panning process enriches the cell suspension for the earlier lineage stage cells. Then the cell suspension is transferred to low attachment dishes and again in serum-free medium, one designed for the early lineage stage cells, and left overnight in an incubator at 37° C. The conditions foster self-assembly of the lineage-stage-matched epithelial and mesenchymal cells into organoids. Organoids can be obtained from mixing of early stages of epithelia (ES cells, iPS cells, determined stem cells, transit amplifying cells, progenitors) with early stages of mesenchymal cells (angioblasts, precursors to endothelia, precursors to stellate cells).

Mixtures of adult epithelial cells with mature mesenchymal cells and chimeric mixtures of mature epithelial cells with early lineage stage mesenchymal cells (ELSMCs) do not usually generate organoids but can be used as mixtures of the cells in suspension in the graft biomaterials. If mature epithelia (e.g. hepatocytes, cholangiocytes, islets, acinar cells, enterocytes, etc.) are partnered with mature mesenchymal cells (e.g., endothelia, stellate cells, stromal cells, myofibroblasts), the mixtures will not result in successful integration of the grafts into the target site or organ but rather in ones that persist at the surface of the organs or tissues. If chimeric mixtures are used comprising adult and stem/progenitors (e.g. mature hepatocytes with angioblasts), then engraftment does occur, since there is a source of MMPs that enable engraftment and migration of the cells.

In another aspect, the isolated cells of the internal organ may be solidified ex vivo within the biomaterials prior to introducing the cells into the hosts, or in the alternative, injected as a fluid substance and allowed to solidify into a graft in vivo. Preferably, the cells are introduced at or near the diseased or dysfunctional tissue, and may be introduced via injection or grafted onto/into the tissue, or using an appropriate surgical method.

In another aspect, the biomaterials that can form hydrogels, or a parallel insoluble complex, can comprise hyaluronans, thiol-modified hyaluronans or other glycosaminoglycans (GAGs). A trigger for solidification can be any factor eliciting cross-linking of the matrix components or gelation of those components that can gel. The cross-linker may comprise Poly(ethylene glycol) (PEG) or PEG-diacrylate (PEGDA) hydrogel or a disulfide-containing derivative thereof.

In another aspect, this disclosure provides a methods of forming organoids by culturing a first type of cells (epithelia) with one or more second type of cells (mesenchymal cells), wherein the second type of cells is at a maturational stage to be an appropriate lineage partner of the first type of cells. In some embodiments, this can be achieved by removing mature cells that attach to culture dishes by panning; transferring the cells that did not attach to low attachment culture dishes and in an appropriate medium; and recovering organoids that self-assemble under these conditions. The first type of cells may be epithelial stem cells, committed progenitors of epithelial cells, or mature cells (e.g. hepatocytes). The second type of cells may be stem cells of the mesenchymal lineages (e.g. angioblasts, mesenchymal stem cells), progenitors of those lineages (e.g. endothelial or stellate cell progenitors), or a mixture of early lineage stage mesenchymal cells. Critically, such formation cannot occur under all conditions. For example, culturing in Matrigel does not generate suitable organoids for successful patch grafting. Though Matrigel-prepared organoids might engraft, the extent of engraftment will be muted relative to that with organoids prepared in defined conditions. Moreover, Matrigel cannot be a component of conditions that are to be used for clinical products.

In another aspect, this disclosure provides a method for engrafting cells into an organ comprising contacting a patch graft comprising multiple layers including a biocompatible, biodegradable backing that is neutral in effects on the differentiation of the donor cells; a second layer comprising one or more biomaterials, such as hyaluronans, that can be solidified such as into a hydrogel; a mixture of epithelial cells and supportive mesenchymal cells that are incorporated into the solidified biomaterial; and this Bandaid-like structure attached to a target site by sutures or surgical glue. On the serosal surface of the backing is added a layer of the solidified biomaterials prepared to achieve 400 Pa or higher, a level at least twice that found in the soft biomaterials into which the donor cells are incorporated. The cells within the patch graft are able to engraft and migrate into and throughout the tissue/organ and then to mature to relevant adult fates, dictated by the microenvironment in which they become located. The higher Pascal levels of the biomaterials embedded or comprised into a porous backing blocks the migration of the cells in the wrong direction and that added to the serosal surface of the graft minimizes adhesions of cells from other organs and tissues.

Organoids

According to one embodiment disclosed herein, organoids, floating aggregates of biliary tree stem cells (hereinafter "BTSCs") and early lineage stage mesenchymal cells (hereinafter "ELMCs") proved the most successful method of incorporating cells in the grafts. It is disclosed herein that BTSCs and ELMCs can self-select into organoids by panning to eliminate the mature stellate/stromal cells, and this a proved more efficient and effective in establishing lineage-stage appropriate epithelial-mesenchymal partners for the grafts. In another aspect, this disclosure provides a methods of forming organoids by culturing a first type of cells with a second type of cells, wherein the second type of cells is a stage appropriate lineage partner of the first type of cells, removing mature cells that attach to the culture dish by panning, and recovering the self-assembled organoids from the suspension of the culture. The first type of cells may be epithelial stem cells or committed epithelial cells. The second type of cells may be cells of the mesenchymal lineage, mesenchymal stem cells, or early lineage stage mesenchymal cells. Further aspects relate to the self-assembled organoid and uses thereof.

In some embodiments, either the donor cells and/or the supporting mesenchymal cells express matrix metallo-proteinases (hereinafter MMPs). Without being limited by theory, it is believed that the MMPs allows for merger of donor and host cells, and the dissolution of Glisson's capsule (or the equivalent capsule around the tissue or organ). The disclosure herein provides that in some embodiments, the early stage stem cells or ELMCs express high levels of MMPs, whereas the mature hepatocytes express low levels of MMPs. In some embodiments, partnering mature hepatocytes with mature sinusoidal endothelia (CD31+++, VEGF-receptor+, type IV collagen+ and negative for CD117) and those for adult cholangiocytes are associated with mature stellate and stromal cells (ICAM-1+, ASMA+, Vitamin A++, type I collagen+) results in cell aggregates that remain at the surface of the organ and cannot be effectively engrafted. In some embodiments, engraftment of mature epithelial cells requires that they are partnered with immature mesenchymal cells that produce the requisite MMPs for engraftment and migration.

According to one embodiment disclosed herein, organoids, floating aggregates of stem/progenitor cells, such as BTSCs and ELSMCs, proved the most successful presentation of cells for success at patch grafting. It is disclosed herein that BTSCs and ELSMCs can self-select into organoids by elimination of the mature mesenchymal cells by standard panning procedures for cells that attach to regular dishes under serum-free conditions, followed by culturing the remaining cells (those that did not attach) in low attachment dishes and in serum-free, defined medium. Organoids self-assemble under these conditions.

In another aspect, this disclosure provides a method of forming organoids by culturing a first type of cells, epithelia, with a second type of cells, mesenchymal cells, wherein the second type of cells is a stage appropriate lineage partner of the first type of cells, removing mature cells that attach to the regular culture dishes by panning procedures, and recovering the organoids that self-assemble from the suspension of the culture on culture dishes that are low attachment ones. The first type of cells may be epithelial stem cells, transit amplifying cells committed epithelial progenitors. The second type of cells may be stem cells of the mesenchymal cell lineages, transit amplifying cells or committed mesenchymal progenitors.

In some embodiments, either the donor cells and/or the supporting mesenchymal cells express matrix metallo-proteinases (hereinafter MMPs). Without being limited by theory, it is believed that the MMPs results in dissolution of the capsules around tissues or organs and allows for merger of donor and host cells. The disclosure herein provides that in some embodiments, the early stage stem cells or ELMCs express high levels of MMPs, whereas the mature hepatocytes express low levels of MMPs. In some embodiments, partnering mature hepatocytes with mature sinusoidal endothelia (CD31+++, VEGF-receptor+, type IV collagen+ and negative for CD117) and those for adult cholangiocytes are associated with mature stellate and stromal cells (ICAM-1+, ASMA+, Vitamin A++, type I collagen+) results in cell aggregates that remain at the surface of the organ and cannot be effectively engrafted. In some embodiments, engraftment of mature epithelial cells requires that they are partnered with immature mesenchymal cells that produce the requisite MMPs for engraftment and migration.

According to one embodiment disclosed herein, organoids, floating aggregates of stem/progenitor cells, such as BTSCs and ELSMCs, proved the most successful presentation of cells for success at patch grafting. It is disclosed herein that BTSCs and ELSMCs can self-select into organoids by elimination of the mature mesenchymal cells by standard panning procedures for cells that attach to regular dishes under serum-free conditions, followed by culturing the remaining cells (those that did not attach) in low attachment dishes and in serum-free, defined medium. Organoids self-assemble under these conditions.

In another aspect, this disclosure provides a method of forming organoids by culturing a first type of cells, epithelia, with a second type of cells, mesenchymal cells, wherein the second type of cells is a stage appropriate lineage partner of the first type of cells, removing mature cells that attach to the regular culture dishes by panning procedures, and recovering the organoids that self-assemble from the suspension of the culture on culture dishes that are low attachment ones.

The first type of cells may be epithelial stem cells, transit amplifying cells committed epithelial progenitors. The second type of cells may be stem cells of the mesenchymal cell lineages, transit amplifying cells or committed mesenchymal progenitors.

In some embodiments, for success with patch grafting strategies, either the donor cells and/or the supporting mesenchymal cells must express multiple matrix metallo-proteinases (hereinafter MMPs) and especially secreted forms of MMPs. Without being limited by theory, it is believed that multiple isoforms of the MMPs allows for the dissolution of the capsule around the organ or tissue followed by rapid migration of donor cells into the host tissue. The disclosure herein provides that the early stage epithelial stem cells and/or ELSMCs express high levels of membrane-associated and/or secreted MMPs, whereas the mature cells (e.g. hepatocytes) express low levels of secreted MMPs even if they express plasma membrane-associated MMPs. Engraftment of such adult cells (e.g. hepatocytes, cholangiocytes, islets, enterocytes, etc.) requires that the mesenchymal partner be a cellular source of MMPs, particularly the secreted forms of MMPs if engraftment is to occur. An alternative is to provide the relevant isoforms of MMPs, that is purified forms of them, in the biomaterials of the graft.

According to this disclosure, the numbers of cells that can be engrafted using a patch graft are considerable (>$10^8$) and dictated by the dimensions of the graft, the number and size of the organoids (or the number of cells—if not part of organoids), whether the donor cells are stem cells or mature cells, and the expression of secreted and membrane-associated MMPs (whether from the epithelia and/or from the mesenchymal cells). These findings are quite distinct from the limited numbers of cells (e.g. $10^5$-$10^6$) feasible with vascular delivery or by injection grafting.

It is disclosed herein that the making the grafts comprises mixing of cells with appropriate biomaterials that can become insoluble and keep cells localized to the target site. In another aspect, the isolated cells of the internal organ may be solidified ex vivo within the biomaterials prior to introducing the cells into the hosts, or in the alternative, injected as a fluid substance and allowed to solidify in vivo. In another aspect, the biomaterials that can form hydrogels, or a parallel insoluble complex, can comprise hyaluronans or other non-sulfated or minimally sulfated glycosaminoglycans, a thiol-modified sodium hyaluronate or plant derived material (e.g. alginates). A trigger for solidification can be any factor eliciting cross-linking of the matrix components or gelation of those that can gel. The cross-linker may comprise polyethylene glycol diacrylate or a disulfide-containing derivative thereof. Preferably, the insoluble complex of cells and biomaterials possesses a viscoelasticity ranging from about 0.1 to 200 Pa, preferably about 0.1 to about 1 Pa, about 1 to about 10 Pa, about 10-100 Pa, or about 100 to about 200.

Preferably, the cells are introduced at or near the diseased or dysfunctional tissue, and may be introduced via injection or surgical delivery. Without being limited by theory, it is an hypothesis herein that more rigid HA hydrogels, (e.g. >500 Pa), triggers differentiation of the cells and reduces engraftment due, in part, to the reduction in expression of MMPs with maturation and, in parallel reduction in ability to migrate.

Backing

There are multiple options for the biocompatible, biodegradable backing with neutrality to the maturational state of the donor cells. They include forms of *Bombyx* moth silk such as Seri$^R$ Surgical Silk Scaffolds or Contour Seri-Silk (Sofregen, New York, N.Y.), other derivatives of *Bombyx* moth silk, amnion derivatives, omentum, placenta, and synthetic textiles or materials, such as forms of Polyglycolic acid-co-poly-L-lactic acid (PGA/PLLA). Critical to the effectiveness of the backing is that it has minimal effects on the differentiation of the donor cells. Thus, many forms of backings used clinically are not useful for patch grafting, since they are comprised of components (e.g. forms of mature types of extracellular matrix) that induce differentiation of the donor cells.

The backing must have sufficient tensile strength to permit attaching the graft to the target site by sutures or by surgical glue. It should be comprised of a biocompatible, biodegradable material that is capable of degrading within a couple of months but with degradation products that do not alter the maturational state of the donor cells. Thus, the products should have minimal effects on the pH or on other facets of the environment. The backing must also be able to fit to the surface of the target site; so flexible backing will facilitate using the grafts on sites of significant curvature. Seri-Silk is a non-limiting example of a suitable material for the backing. An aminion derived alternative is also contemplated as a suitable material for the backing, such as but not limited to the aminion derived material produced by Osiris Therapeutics, Inc (Columbia, Md.).

Backing may be sourced from a porous scaffold, such as Seri-silk, or a non-porous membrane, such as amnion or placental membrane or omentum, or can be a porous or non-porous synthetic textile, or a combination thereof. If the backing is porous it should be infused/impregnated with a biomaterial to seal it and so inhibit migration of said population of cells in the direction of the backing, i.e. away from the target site, or through the backing The critical features of the backing material that it is biocompatible, biodegradable, neutral as defined above, and has sufficient tensile strength as described above. Further, the material may optionally be bioresorbable.

The backing may be further optimized depending on the use. For example, in some embodiments, a patch graft is useful for skin and underlying dermal tissues if it comprises a backing designed to survive the drying effect of air.

Hydrogel matrices as disclosed herein above may also be useful in other parts of the patch graft. For example, should the biocompatible, biodegradable backing be porous, a hydrogel may be used to inhibit migration of said population of cells in the direction of the backing. Such a hydrogel would require a higher viscoelasticity compared to the hydrogel, e.g., between 1.5 and 15 fold greater, for example 2 fold greater. Non-limiting examples of a suitable viscoelasticity include by are not limited a viscoelasticity properties ranging from about 250 to about 600 Pa, for example at least about 250 Pa, at least about 300 Pa, at least about 350 Pa, at least about 400 Pa, at least about 450 Pa, at least about 500 Pa, at least about 550 Pa, at most about 600 Pa, at most about 550 Pa, at most about 500 Pa, at most about 450 Pa, at most about 400 Pa, at most about 350 Pa, at most about 200 Pa and/or any individual value in between such as but not limited to about 250 Pa, about 300 Pa, about 350 Pa, about 400 Pa, about 450 Pa, about 500 Pa, about 550 Pa, and about 600 Pa. Further non-limiting examples of suitable viscoelasticity include by are not limited a viscoelasticity ranging from about 600 to about 800 Pa, for example at least about 600 Pa, at least about 650 Pa, at least about 700 Pa, at least about 750 Pa, at most about 800 Pa, at most about 750 Pa, at most about 700 Pa, at most about 650 Pa, at most about 600 Pa, and/or any individual value in between such as but not limited to about 600 Pa, about 650 Pa, about 700 Pa, about 750 Pa, and about 800 Pa. Still further non-limiting examples include the range from about 250 Pa to about 800 Pa.

Further still, the hydrogels disclosed herein may be useful as a coating to prevent adhesion on the serosal surface of the backing, which is opposite to the side of the backing adjacent to the cells. Such a hydrogel may should have a viscoelasticity between that suitable for the hydrogel in which the cells are comprised and that suitable to seal the backing. Non-limiting examples of a suitable viscoelasticity include by are not limited a viscoelasticity ranging from about 250 to about 400 Pa or about 500 Pa, for example at least about 250 Pa, at least about 300 Pa, at least about 350 Pa, at least about 400 Pa, at least about 450 Pa, at most about 500 Pa, at most about 450 Pa, at most about 400 Pa, at most about 350 Pa, at most about 200 Pa and/or any individual value in between such as but not limited to about 250 Pa, about 300 Pa, about 350 Pa, about 400 Pa, about 450 Pa, and about 500 Pa.

Grafts, In General

In general, a patch graft may be designed using the aforementioned methods and components for transplantation of donor (allogeneic or autologous) cells to a solid organ or tissue and with conditions sustaining and maintaining donor cells at an early maturational lineage stage. More particularly, a patch graft is contemplated, which useful for transplantation of donor cells (allogeneic or autologous) to a solid organ or tissue, with conditions sustaining and maintaining some or all of the donor cells at an early maturational lineage stage. In some embodiments, the donor cells are a mixture of epithelial and mesenchymal cells. In some embodiments both donor cell populations are stem/progenitor cells. In some embodiments, the epithelial cells are mature cells (e.g. hepatocytes, islets, etc.) and the mesenchymal cells are stem/progenitor cells. In some embodiments, the conditions of the graft biomaterials, e.g. the medium and matrix components, enable both the donor cell populations or at least the mesenchymal cell population to remain as stem/progenitor cells. In some embodiments the medium comprises a basal medium and soluble signals. In further embodiments, this basal medium and soluble signals are supportive of maintenance of stemness in both donor populations or at least in the mesenchymal cell population. In some embodiments, the matrix, optionally comprising extracellular matrix components, and its level of rigidity are supportive of maintenance of stemness of both the donor populations or at least the mesenchymal cell population. In some embodiments, the matric comprises hyaluronans, optionally prepared as a soft hydrogel having a viscoelasticity of about 50 Pa to about 150 Pa. In some embodiments, the patch graft comprises a backing which has sufficient mechanical strength to enable the graft to be tethered to the target site and consists of a biocompatible, biodegradable material that does not significantly alter the maturational lineage stage of the donor cells. Optionally, without further modifications, the backing should be adequate on its own to protect the layer containing the donor cells without significantly affecting the donor cells' maturational lineage stage. In some embodiments, the backing is a mesh or scaffold and is further impregnated with a biomaterial such as hyaluronana with a viscoelasticity sufficiently high as to make any cells migrating into it mature enough to abrogate the migration of the donor cells in a direction other than towards the target site. In some embodiments, this viscoelasticity is about 500 Pa or greater. In some embodiments, the serological surface of the graft is coated with a biomaterial to minimize adhesions from adjacent tissue or organs. In some embodiments, these biomaterials have a viscoelasticity of about 200 Pa to about 300 Pa.

The proposed backing is contemplated to have sufficient resilience to withstand mechanical forces, is able to be tethered to the target organ or tissue, and has sufficient flexibility to be tethered to locations with curvature. Also any biomaterial (other than a hydrogel) can be utilized so long as the biomaterial is capable of sustaining and maintaining the cell populations and has viscoelasticity properties sufficient to allow for migration of the cell population within or away from the patch graft.

In another embodiment, the patch graft is useful for sustaining and maintaining a population of cells and comprises: (a) a population of cells (optionally of a single type), supported in a medium in a hydrogel or other biomaterial having viscoelasticity sufficient to allow for migration of the cells within or away from the patch graft; and (b) a backing comprising a biocompatible, biodegradable material having a viscoelasticity sufficient to inhibit (or provide a barrier to) migration of the cell population in a direction of the backing, It is important to note that MMPs can be membrane-associated and/or secreted MMPs; they can be provided by MMP producing cells, derived from such cells, or they can be added to the compositions of interest (e.g., purified or produced recombinantly).

In another embodiment, a covering or coating for a patch graft or tissue is provided which comprises a hydrogel or other biomaterial with sufficient viscoelasticity and resilience to withstand mechanical forces applied against the covering or coating, including such forces being applied from or by other tissues and organs. By use of the covering or coating, a method is provided for inhibiting or preventing a formation of adhesions (which may involve or result from mechanical forces or contact from other organs and tissues), which method comprises covering or coating a surface with a hydrogel or other comparable biomaterial.

In yet another embodiment, a method of engrafting cells into a target tissue is provided, which comprises contacting a target tissue with a patch graft, comprising: (a) a population of cells, including at least one population having an early lineage stage, comprising a single type or multiple types of cells supported in a medium in a hydrogel or other biomaterial having rheological properties (e.g., viscoelasticity) sufficient to allow for migration of cells of the population within or away from the patch graft; and (b) a backing comprising a biocompatible, biodegradable material having rheological properties (e.g., viscoelasticity) sufficient to inhibit (or provide a barrier to) migration of cells of the population in a direction of said backing, the patch graft configured to sustain and maintain said population of cells while inhibiting said at least one population having an early lineage stage from differentiating or further maturing to a later lineage stage. In a further embodiment, a method is provided in which the one population having an early lineage stage is capable of expressing membrane-associated and/or secreted matrix metalloproteinases (MMPs). In another embodiment, the cells do not have this capability but MMPs are present or included from other sources (e.g. recombinant).

Grafts with a Cell Source of MMPs

Aspects of the disclosure relate to a patch graft for sustaining and maintaining a mixed population of cells, comprising: (a) a mixed population having two or more cell types, at least one of which is at an early lineage stage that is capable of expressing secreted and/or membrane-associated and/or secreted matrix metalloproteinases (MMPs), said mixed population supported in a medium present in a hydrogel matrix having a viscoelasticity sufficient to allow for migration of said mixed population, optionally, within or away from said hydrogel and/or within or away from the patch graft; (b) a backing comprising a biocompatible, biodegradable material having a viscoelasticity sufficient to inhibit a migration of said mixed population in a direction of said backing; and, optionally, ((c) a hydrogel overlaid on a serosal (i.e. outside) surface of said backing, which is opposite to that in contact with said mixed population and, in embodiments where the patch graft is tethered to a target site, is opposite the side in contact with the target site (e.g. organ or tissue). In some embodiments, this layer prevents or inhibits adhesions by or from other tissues or organs. In some embodiments, the patch graft is configured to sustain and maintain said mixed population while inhibiting said at least one early lineage stage cell type from differentiating or further maturing to a later lineage stage that is no longer capable of expressing membrane-associated and/or secreted MMPs.

In some embodiments, the graft might contain only one cell type such as an embryonic stem (ES) cell or induced pluripotent stem (iPS) cells. This can be successful as long as this cells are a cellular source of MMPs or, alternatively, other sources such as purified (e.g. recombinant) forms of MMPs are added to the graft.

In some embodiments, said backing is porous or non-porous. In some embodiments, the backing comprises a porous and/or non-porous mesh, scaffold, or membrane. In some embodiments, the backing comprises silk; a synthetic textile; or a natural material such as amnion, placenta, or omentum or derivatives thereof; or a combination thereof. In some embodiments, said backing comprises a porous mesh infused with a hydrogel or other biomaterial used to convert it into a barrier. In further embodiments, such an infusion prevents cell migration away from the target organ or tissue. In some embodiments, In some embodiments, said backing comprises a solid material.

In some embodiments, one or more of said hydrogels comprise hyaluronans.

In some embodiments, said medium comprises Kubota's Medium or another medium supportive of stem cells and able to maintain stemness.

In some embodiments, said mixed population comprises mesenchymal cells and epithelial cells. In some embodiments, said epithelial cells may be ectodermal, endodermal, or mesodermal. In some embodiments, said mesenchymal cells comprise early lineage stage mesenchymal cells (ELSMCs). In some embodiments, said ELSMCs comprise one or more of angioblasts, precursors to endothelia, precursors to stellate cells, and mesenchymal stem cells (MSCs). In some embodiments, said epithelial cells comprise epithelial stem cells. In some embodiments, said epithelial cells comprise biliary tree stem cells (BTSCs). In some embodiments, said epithelial cells comprise committed and/or mature epithelial cells. In some embodiments, said committed and/or mature epithelial cells comprise mature parenchymal cells. In some embodiments, said mature parenchymal cells comprise one or more of hepatocytes, cholangiocytes, and islet cells. In some embodiments, said mesenchymal cells and epithelial cells both comprise stem cells.

In some embodiment said mixed population comprises autologous and/or allogeneic cells.

In some embodiments, one or more cell types are genetically modified.

"Layered" Grafts

In some embodiments, the patch graft is understood as a multi-layered graft. For example, provided herein are patch grafts comprising, consisting of, or consisting essentially of multiple layers including, at least: (a) a soft first layer of hydrogel comprising donor cells, optionally epithelial cells and/or mesenchymal cells; (b) a stiff second layer of hydrogel; and (c) a third layer comprising a biocompatible, biodegradable backing. In some embodiments, particular those where the third layer is porous, the second layer is incorporated, impregnated, and/or infused into the third layer. In some embodiments, the patch grafts further comprise a fourth layer of hydrogel. In some embodiments of the patch graft, the fourth layer is coated or painted onto a serosal surface of the graft. In some embodiments of the patch graft, the first layer is adapted to directly contact a target tissue or organ.

As used herein, "soft" refers to a hydrogel layer that exhibits a low level of internal pressure as determined quantitatively by Pascal (Pa) assays. A Pascal is defined as one newton per square meter. In some embodiments, a soft layer has a viscosity of about 10 Pa to about 300 Pa, about 50 Pa to about 250 Pa, about 100 Pa to about 250 Pa, about 50 Pa to about 200 Pa, about 150 Pa to about 200 Pa, or about 100 Pa to about 200 Pa. In a particular embodiment, a soft hydrogel layer has a viscosity that is less than or about 200 Pa.

As used herein, "stiff" refers to a hydrogel layer that exhibits a high level of internal pressure as determined quantitatively by Pascal (Pa) assays. In some embodiments, a stiff layer has a viscosity of about 300 Pa to about 3000 Pa, about 300 Pa to about 1000 Pa, about 400 Pa to about 750 Pa, about 400 Pa to about 550 Pa, about 450 Pa to about 600 Pa, or about 500 Pa to about 600 Pa. In a particular embodiment, a stiff hydrogel layer has a viscosity that is greater than or about 500 Pa.

Preferably, for the first layer of the layered graft, the insoluble complex of cells and biomaterials possesses a viscosity or viscoelasticity ranging from about 0.1 to 200 Pa, preferably about 0.1 to about 1 Pa, about 1 to about 10 Pa, about 10 to 100 Pa, or about 100 to about 200, or about 50 to about 250 Pa, or about 200 Pa. Preferably, for the first layer of the layered graft, the insoluble complex of cells and biomaterials possesses a viscoelasticity ranging from about 0.1 to 200 Pa, preferably about 0.1 to about 1 Pa, about 1 to about 10 Pa, about 10-100 Pa, or about 100 to about 200.

In some embodiments, one or more of the cells in the mixture is a source of secreted and/or membrane-associated MMPs. In some embodiments, such as but not limited to those involving stem/progenitor cell populations that naturally secrete MMPs, variables that mute MMP expression—optionally secreted MMP expression—are controlled in the patch graft. Non-limiting examples of such variables include variables that result in maturation of stem/progenitor cells, such as but not limited to serum supplementation to media or to the graft biomaterials, hormones or other soluble signals that influence differentiation of the epithelial and/or mesenchymal cells, oxygen levels (as anaerobic conditions keep the cells immature, whereas higher oxygen levels promote differentiation), and the rigidity of graft materials (as mechanical forces such as shear force and compression may drive differentiation).

In some embodiments of the patch graft, the viscosity of the first layer is about 50 to about 250 Pa. In some embodiments of the patch graft, the viscosity of the first layer is about 200 Pa. In some embodiments of the patch graft, the viscosity of the second layer is about 250 Pa to about 600 Pa. In some embodiments of the patch graft, the viscosity of the second layer is about 500 Pa. In some embodiments of the patch graft, the viscosity of the fourth layer is about 250 to about 500 Pa. In some embodiments of the patch graft, the viscosity of the fourth layer is about 400 Pa. In some embodiments of the patch graft, the viscosity of the second layer is greater than the viscosity of layer 1. In some embodiments of the patch graft, the viscosity of the second layer is about 1.5 to about 15 fold greater than the viscosity of the first layer. In some embodiments of the patch graft, the second layer is about 2 fold greater than the viscosity of the first layer.

In one embodiment, a patch graft comprises, consists of, or consists essentially of layers starting with that in contact with the target site and consisting of donor cells embedded into a soft (<200 Pa) hydrogel prepared in a serum-free, defined medium (these cells are to engraft and migrate into the tissue); a second layer of the hydrogel prepared in the same medium and triggered to have a higher rigidity (e.g. ~500 Pa or higher) providing a barrier for the donor cells to migrate in any direction other than towards the target tissue; a third layer, a biocompatible, biodegradable, bioresorable backing that is neutral in effects on the maturational state of the donor cells and can be used surgically or through other means to tether the graft to the target site; and a final layer of the hydrogel that is intermediate in rigidity between the soft hydrogel and the very rigid one and sufficiently fluid to be painted or coated onto the surface to minimize adhesions by nearby tissues.

In some embodiments of the patch graft, the first and second layers each comprise one or more hyaluronans. In some embodiments of the patch graft, the fourth layer comprises one or more hyaluronans.

In some embodiments of the patch graft, the epithelial cells and the mesenchymal cells form one or more aggregates. In some embodiments of the patch graft, the one or more aggregates is an organoid. In some embodiments of the patch graft, the epithelial cells comprise epithelial stem cells. In some embodiments of the patch graft, the epithelial cells comprise biliary epithelial cells. In some embodiments of the patch graft, the epithelial cells comprise committed and/or mature epithelial cells. In some embodiments of the patch graft, the committed and/or mature epithelial cells comprise mature parenchymal cells. In some embodiments of the patch graft, the mature parenchymal cells comprise one or more of hepatocytes, cholangiocytes, and islet cells.

In some embodiments of the patch graft, the mesenchymal cells are supportive mesenchymal cells. In some embodiments of the patch graft, the mesenchymal cells comprise early lineage stage mesenchymal cells (ELSMCs). In some embodiments of the patch graft, the ELSMCs comprise one or more of the group consisting of angioblast, precursor to endothelia, precursor to stellate cells, and mesenchymal stem cell (MSC).

In some embodiments of the patch graft, the epithelial cells and the mesenchymal cells are not lineage stage partners of one another. In some embodiments of the patch graft, the epithelial cells are mature cells. In some embodiments of the patch graft, the mesenchymal cells are ELSMCs.

In some embodiments of the patch graft, at least one of the epithelial cells and the mesenchymal cells are derived from a donor. In some embodiments, the donor is a subject in need of a tissue transplant. In some embodiments, the donor is the source of healthy cells for a tissue transplant. In some embodiments of the patch graft, the at least one of the epithelial cells and the mesenchymal cells are autologous to an intended recipient of the patch graft. In some embodiments, all of the cells (i.e. epithelial and mesenchymal) are autologous to the intended recipient of the graft. In some embodiments, the donor of cells may be one other than the recipient (allograft) or may also be the subject (autologous) having the internal organ in a diseased or dysfunctional condition, optionally, wherein are obtained from a portion of the internal organ that is not diseased or dysfunctional and/or that the cells have been genetically modified to restore function. For establishing a model system to study a disease, the donor cells can be ones that have the disease and that are transplanted onto/into normal tissue in an experimental host.

In some embodiments of the patch graft, at least one of the epithelial cells or the mesenchymal cells are modified. In some embodiments, all of the cells are modified. In some embodiments, the modification is genetic modification. In some embodiments, the one or more cells is modified to express a therapeutic nucleic acid or polypeptide. In some embodiments, the one or more cells is modified to express a wild-type allele of a nucleic acid or polypeptide.

In some embodiments of the patch graft, the biocompatible, biodegradable backing is bioresorbable. In some embodiments of the patch graft, the biocompatible, biodegradable backing comprises a porous material. In some embodiments of the patch graft, the biocompatible, biodegradable backing comprises a scaffold or membrane. In some embodiments of the patch graft, the scaffold or membrane comprises silk, amnion, a synthetic textile, or a combination thereof. In some embodiments, the biocompatible, biodegradable backing does not comprise any factor that induces or prevents differentiation in cells. In some embodiments of the patch graft, the biocompatible, biodegradable backing does not include one or more components derived from mature extracellular matrix. In some embodiments of the patch graft, the component derived from mature extracellular matrix is type I collagen.

In some embodiments of the patch graft, the patch graft further comprises one or more matrix metallo-proteinases (MMPs). In some embodiments of the patch graft, the MMP is a membrane-associated MMP. In some embodiments of the patch graft, the membrane-associated MMP is provided by one or more of the epithelial cells or the mesenchymal cells. In some embodiments of the patch graft, the MMP is a secreted MMP. The secreted MMPs may optionally be produced naturally by the one or more of the epithelial or mesenchymal cells or optionally be produced due to transformation of the one or more of the epithelial or mesenchymal cells with a recombinant expression vector for MMP production.

In some aspects, provided herein is a patch graft comprising, consisting of, or consisting essentially of multiple layers including, at least: a soft first layer of hydrogel comprising biliary tree stem cells; a stiff second layer of hydrogel; and a third layer comprising a biocompatible, biodegradable backing.

In one embodiment, a patch graft consists of layers of materials and cells that collectively form a "bandaid-like graft" that can be tethered surgically or otherwise to a target site. The first layer, that against the target site, comprises a soft hydrogel (under 200 Pa) into which are seeded a mixture of epithelial cells and supportive mesenchymal cells suspended in a defined, serum-free, nutrient-rich medium designed for expansion and/or survival of the cells; a second layer containing a hydrogel prepared in the same medium but gelled to a more rigid level (i.e. higher Pascal levels) and forming a barrier blocking cells from migrating in a direction other than to the target sites; a third level comprising a biocompatible, biodegradable backing that does not affect or minimally affects the differentiation level of the donor cells but acting as a mechanical support structure for the patch; a fourth layer comprised of paintable hydrogel (again such as hyaluronans) that is at a rigidity level intermediate between that of the soft versus rigid hydrogel and serving to minimize adhesions to the graft from cells from neighboring tissues. The hydrogels must consist of a material that is biocompatible, biodegradable and "tunable", meaning regulatable with respect to rigidity. One successful material for the hydrogels is thiol-modified hyaluronan that can be triggered to form hydrogels when exposed to oxygen and/or to poly (ethylene glycol) diacrylate (PEGDA) and readily "tunable" by the precise ratios of hyaluronan and PEGDA concentrations (and/or oxygen levels).

In another embodiment, a patch graft comprises multiple layers. The first layer, that against the target site, is of a soft hydrogel that is minimally sulfated or non-sulfated GAG or other non-sulfated or neutral biomaterial that can be gelled or solidified and into which is placed donor cells. A second layer of a hydrogel or biomaterial that is more rigid and incorporated into/onto or within a backing, a biocompatible, biodegradable, bioresorbable backing that allows the patch to be handled for surgical or other purposes and that serves as a barrier forcing cells to migrate towards the target tissue. The serosal side of the backing is coated at the time of surgery with biomaterials such as hyaluronans (or other minimally or non-sulfated GAGs or other materials that can be gelled or solidified) and in which the Pascal levels are at least twice that of the Pascal levels found in the layer of soft biomaterials; this serves the purpose of minimizing adhesions from neighboring tissues. The patch graft is tethered to the target organ or tissue, and the cells are able to migrate into the tissue or organ and become fully incorporated.

In a particular embodiment, a patch graft comprises a first layer of a soft biomaterial (<200 Pa), such as a soft hyaluronan hydrogel, and into which are placed the donor cells to be transplanted in a serum-free, defined medium tailored to the lineage stage of the cells. This layer is placed atop a more rigid layer (e.g. a more rigid hydrogel) that serves as a barrier forcing the donor cells to be directed in their migration to the target tissue. The more rigid layer is prepared ahead of time on a backing, a biocompatible, biodegradable backing that enables handling the patch for surgical or other procedures so as to affix the patch to the target site. The final layer is a biomaterial that is intermediate in rigidity from that for the donor cells on the target tissue side and that for the barrier. This layer is added on the serosal side of the graft and at the time of surgery and serves to minimize adhesions from neighboring tissues. The biocompatible, biodegradable backing may be Seri-silk or a derivative thereof.

Methods of Use and Delivery for Patch Grafts

Aspects of the disclosure relate to compositions and methods for engrafting cells into an organ. Efforts to transplant cells from solid organs into internal organs typically made use either of direct injection or delivery of cells via a vascular route. Lanzoni, G. et al. Stem Cells 31, 2047-2060 (2013). These methods of transplantation result in small numbers of cells being transplanted to the target site, and in risks of emboli that can be life threatening. Transplantation is improved if the cells are delivered by "injection grafting" in which the cells are suspended in or coated with hyaluronans and then co-injected with a trigger (PEGDA) that causes the hyaluronan to gel in situ as described in Turner R. et al. Hepatology 57, 775-784 (2013). Injection grafting methodologies provide a strategy for localizing cells to a specific site, albeit in small numbers, typically $10^5$-$10^7$, $10^6$-$10^7$, or $10^5$-$10^6$ cells per injection site. This strategy eliminates or minimizes ectopic cellular distribution and optimizes the integration of the cells in the site. However, if mature functional cells are used, they may be highly immunogenic, necessitating long-term immunosuppression. Also, the quantity of cells that are able to be injected may be insufficient to achieve the requisite clinical results.

These hurdles and concerns are overcome by "patch grafting" strategies described herein. In some embodiments, "bandaid-like" grafts are tethered surgically or otherwise to the surface of an organ or tissue; the conditions of the graft are such that the cells engraft fully into the site, migrate throughout the organ/tissue, and then mature into relevant adult cell types. The potential for transplantation of large numbers of cells (>$10^8$ cells) is shaped or determined by the size of the patch, the number or mixture of cells within the graft, and the source of multiple forms of MMPs, ideally cellular sources of the MMPs. Moreover, in some embodiments the use of organoids facilitates the ability to stockpile donor cells given the ease by which the organoids can be cryopreserved under defined, serum-free conditions.

The patch graft composition provided herein is directed to direct grafting of cells onto the tissue or solid organ. The method is safe, avoids emboli and ectopic cell distribution, and optimizes cell number engraftment and distribution into and throughout the tissue.

Accordingly, provided herein are methods of engrafting cells into a target tissue comprising, consisting of, or consisting essentially of contacting the target tissue with a patch graft disclosed herein above.

In some embodiments of the methods, the target tissue is selected from the group consisting of liver, pancreas, biliary tree, thyroid, thymus, gastrointestine, lung, prostate, breast, brain, bladder, spinal cord, skin and underlying dermal tissues, uterus, kidney, muscle, blood vessel, heart, cartilage, tendons, and bone tissue. In some embodiments of the methods, the target tissue is liver tissue. In some embodiments of the methods, the target tissue is pancreatic tissue. In some embodiments of the methods, the target tissue is biliary tree tissue. In some embodiments of the methods, the target tissue is gastrointestinal tissue. In some embodiments, the tissue is diseased, damaged, or has a disorder. In some embodiments of the methods, the target tissue is kidney tissue.

In some embodiments of the methods, the target tissue is an organ. In some embodiments of the methods, the organ is an organ of the musculoskeletal system, the digestive system, the respiratory system, the urinary system, the female reproductive system, the male reproductive system, the endocrine system, the circulatory system, the lymphatic system, the nervous system, or the integumentary system. In some embodiments of the methods, the organ is selected from the group consisting of liver, pancreas, biliary tree, thyroid, thymus, gastrointestines, lung, prostate, breast, brain, bladder, spinal cord, skin and underlying dermal tissues, uterus, kidney, muscle, blood vessel, heart, cartilage, tendon, and bone. In some embodiments, the organ is diseased, damaged, or has a disorder.

Also provided herein are methods of treating a subject with a liver disease or disorder, the methods comprising, consisting of, or consisting essentially contacting the subject's liver a patch graft disclosed herein above. In some embodiments of the methods, the liver disease or disorder is liver fibrosis, liver cirrhosis, hemochromatosis, liver cancer, biliary atresia, nonalcoholic fatty liver disease, hepatitis, viral hepatitis, autoimmune hepatitis, fascioliasis, alcoholic liver disease, alpha 1-antitrypsin deficiency, glycogen storage disease type II, transthyretin-related hereditary amyloidoisis, Gilbert's syndrome, primary biliary cirrhosis, primary sclerosing cholangitis, Budd-Chiari syndrome, liver trauma, or Wilson disease.

In other aspects, provided herein are methods of treating a subject with a disease or disorder of the pancreas, the methods comprising, consisting of, or consisting essentially of contacting the subject's pancreas with a patch graft disclosed herein above. In some embodiments of the methods, the disease or disorder of the pancreas is diabetes mellitus, exocrine pancreatic insufficiency, pancreatitis, pancreatic cancer, sphincter of Oddi dysfunction, cystic fibrosis, pancreas divisum, annular pancreas, pancreatic trauma, or hemosuccus pancreaticus.

In other aspects, provided herein are methods of treating a subject with a gastrointestinal disease or disorder, the method comprising, consisting of, or consisting essentially of contacting one or more of the subject's intestines with a patch graft disclosed herein above. In some embodiments, the gastrointestinal disease or disorder is gastroenteritis, gastrointestinal cancer, ileitis, inflammatory bowel disease, Crohn's disease, ulcerative colitis, irritable bowel syndrome, peptic ulcer disease, celiac disease, fibrosis, angiodysplasia, Hirschsprung's disease, pseudomembranous colitis, or gastrointestinal trauma.

In some aspects, provided herein are methods of treating a subject with a kidney disease or disorder, the methods comprising, consisting of, or consisting essentially of contacting one or more of the subject's kidneys with a patch graft disclosed herein above. In some embodiments of the methods, the kidney disease or disorder is nephritis, nephrosis, nephritic syndrome, nephrotic syndrome, chronic kidney disease, acute kidney injury, kidney trauma, cystic kidney disease, polycystic kidney disease, glomerulonephritis, IgA nephropathy, lupus nephritis, kidney cancer, Alport syndrome, amyloidosis, Goodpasture syndrome, or Wegener's granulomatosis.

In some embodiments of the therapeutic methods, at least one of the epithelial cells and the mesenchymal cells are derived from a donor. In some embodiments, the donor is a subject in need of a tissue transplant. In some embodiments, the donor is the source of healthy cells for a tissue transplant. In some embodiments, at least one of the epithelial cells and the mesenchymal cells are autologous to an intended recipient of the patch graft. In some embodiments, all of the cells (i.e. epithelial and mesenchymal) are autologous to the intended recipient of the graft. In some embodiments, the donor of cells may be one other than the recipient (allograft) or may also be the subject (autologous) having the internal organ in a diseased or dysfunctional condition, optionally, wherein are obtained from a portion of the internal organ that is not diseased or dysfunctional and/or that the cells have been genetically modified to restore function.

In some embodiments, the patch graft used in the methods disclosed herein above is a patch graft comprising multiple layers including, at least: a first layer of hydrogel comprising epithelial cells and mesenchymal cells; a second layer of hydrogel; a third layer comprising a biocompatible, biodegradable backing; and optionally a fourth layer of hydrogel. In some embodiments, the methods further comprise allowing the cells contained in the patch graft to become incorporated into the tissue. In some embodiments of the methods, the first layer of hydrogel is soft. In some embodiments of the methods, the second layer of hydrogel is stiff. In some embodiments of the methods, the mesenchymal cells are supportive mesenchymal cells.

In another aspect, this disclosure provides a method for engrafting cells into an organ comprising use of a patch graft, a bandaid-like composite with multiple layers of materials and cells that collectively can be tethered surgically or otherwise to a target site. The first layer, that against the target site, comprises a soft hydrogel (under 200 Pa) into which are seeded a mixture of epithelial cells and supportive mesenchymal cells suspended in a defined, serum-free, nutrient-rich medium designed for expansion and/or survival of the cells; a second layer containing a hydrogel prepared in the same medium but gelled to a more rigid level (i.e. higher Pascal levels) and forming a barrier blocking cells from migrating in a direction other than to the target sites; a third level comprising a biocompatible, biodegradable backing that does not affect or minimally affects the differentiation level of the donor cells and hence is "neutral;" a fourth layer comprised of paintable hydrogel (again such as hyaluronans) that is at a rigidity level intermediate between that of the soft versus rigid hydrogel and serving to minimize adhesions to the graft from cells from neighboring tissues. The hydrogels must consist of a material that is biocompatible, biodegradable and "tunable", meaning regulatable with respect to rigidity. One successful material for the hydrogels is thiol-modified hyaluronan that can be triggered to form hydrogels when exposed to oxygen and/or to poly (ethylene glycol) diacrylate (PEGDA) and readily "tunable" by the precise ratios of hyaluronan and PEGDA concentrations (and/or oxygen levels). The cells under the conditions of the biomaterials of the graft produce multiple matrix-metallo-proteinases (MMPs) that facilitate engraftment, migration, and integration of the donor cells into the tissue of the recipient. The microenvironment of the recipient tissue dictates the adult fate of the transplanted cells.

In another aspect, this disclosure provides a method for engrafting cells into an organ comprising contacting a patch graft comprising multiple layers including, at least, a first layer comprising a biocompatible, biodegradable backing, a second layer comprising one or more hyaluronans including a mixture of epithelial cells and supportive mesenchymal cells and a third layer comprising one or more hyaluronans, in which the layer in which the cells are embedded is very soft (under 200 Pa); a layer associated with the backing is more rigid (~500 Pa or more); and a third layer is intermediate in the level of Pascals and helps to minimize adhesions from nearby tissues or organs. In yet another aspect, the cells may be engrafted into an organ selected from the group consisting of liver, pancreas, biliary tree, thyroid, thymus intestines, lung, prostate, breast, brain, spinal cord, neural ganglia, skin and underlying dermal tissues, uterus, bone, thymus, intestines, uterus, bone, kidney, muscle, blood vessels, or heart.

In yet another aspect, the cells may be engrafted into an organ selected from the group consisting of liver, pancreas, biliary tree, thyroid, thymus thymus, intestines, lung, prostate, breast, brain, spinal cord, neural ganglia, skin and underlying dermal tissues, uterus, bone, tendon, cartilage, kidney, muscle, blood vessels, or heart.

A non-limiting example of a patch graft suitable for the methods disclosed herein is a patch graft comprising: (a) a mixed population having two or more cell types, at least one of which is at an early lineage stage that is capable of expressing secreted and/or membrane-associated and/or secreted matrix metalloproteinases (MMPs), said mixed population supported in a medium present in a hydrogel matrix having a viscoelasticity sufficient to allow for migration of said mixed population, optionally, within or away from said hydrogel and/or within or away from the patch graft; (b) a backing comprising a biocompatible, biodegradable material having a viscoelasticity sufficient to inhibit or provide a barrier to migration of said mixed population in a direction of said backing; and, optionally, ((c) a hydrogel overlaid on a serosal (i.e. outside) surface of said backing, which is opposite to that in contact with said mixed population and, in embodiments where the patch graft is tethered to a target site, is opposite the side in contact with the target site (e.g. organ or tissue). In some embodiments, this layer prevents or inhibits adhesions by or from other tissues or organs. In some embodiments, the patch graft is configured to sustain and maintain said mixed population while inhibiting said at least one early lineage stage cell type from differentiating or further maturing to a later lineage stage that is no longer capable of expressing membrane-associated and/or secreted MMPs.

In some embodiments, said backing is porous or nonporous. In some embodiments, the backing comprises a porous mesh, scaffold, or membrane. In some embodiments, the backing comprises silk; a synthetic textile; or a natural material such as aminion, placenta, or omentum; or a combination thereof. In some embodiments, said backing comprises a porous mesh infused with a hydrogel. In further embodiments, such an infusion prevents cell migration away from the target organ or tissue. In some embodiments, In some embodiments, said backing comprises a solid material.

In some embodiments, the patch graft further comprises a hydrogel overlaid on a serosal surface of said backing, which is opposite to that in contact with said single cell or mixed cell population.

In some embodiments, one or more of said hydrogels comprise hyaluronans.

In some embodiments, said medium comprises Kubota's medium or another medium supportive of stem cells and able to maintain stemness.

In some embodiments, said mixed population comprises mesenchymal cells and epithelial cells.

In some embodiments, said epithelial cells may be ectodermal, endodermal, or mesodermal. In some embodiments, said mesenchymal cells comprise early lineage stage mesenchymal cells (ELSMCs). In some embodiments, said ELSMCs comprise one or more of angioblasts, precursors to endothelia, precursors to stellate cells, and mesenchymal stem cells (MSCs). In some embodiments, said epithelial cells comprise epithelial stem/progenitor cells. In some embodiments, said epithelial cells comprise biliary tree stem cells (BTSCs). In some embodiments, said epithelial cells comprise committed and/or mature epithelial cells. In some embodiments, said committed and/or mature epithelial cells comprise mature parenchymal cells.

In some embodiments, said mature parenchymal cells comprise one or more of hepatocytes, cholangiocytes, and islet cells. In some embodiments, said mesenchymal cells and epithelial cells both comprise stem cells.

In some embodiment said mixed population comprises autologous and/or allogeneic cells.

In some embodiments, one or more cell types are genetically modified.

EXAMPLES

The following examples are non-limiting and illustrative of procedures which can be used in various instances in carrying the disclosure into effect. Additionally, all reference disclosed herein below are incorporated by reference in their entirety.

Example 1: Porcine Model for Patch Graft Validation

Animals

Animals used as hosts or as donors for cells were maintained in facilities at the College of Veterinary Medicine at NCSU (Raleigh, N.C.). Surgeries, necropsies, and the collection of all biological fluids and tissues were performed at these facilities. All procedures were approved by the IACUC committee at NCSU. The pigs being used as recipients were a mixture of six different breeds: a six-way cross consisting of Yorkshires, Large Whites, Landraces (from the sows), Durocs, Spots, and Pietrans (from the boars). This highly heterogeneous genetic background is desirable in that it parallels the heterogeneous genetic constitutions of human populations. The host animals were all females, approximately six weeks of age and ~15 kg.

There were two categories. a) male pigs, approximately six weeks of age and ~15 kg, were used as donors for cell transplantation into females; b) transgenic donor animals carrying a GFP transgene. The GFP+ donor animals were obtained by breeding a transgenic H2B-GFP boar with a wild type gilt by standard artificial insemination. The model was developed via CRISPR-Cas9 mediated homology-directed repair (HDR) of IRES-pH2B-eGFP into the endogenous β-actin (ACTB) locus. The transgenic animals show ubiquitous expression of pH2B-eGFP in all tissues. Fusion of the GFP to H2B results in localization of the GFP marker to the nucleosome and allows clear nuclear visualization as well as the study of chromosome dynamics. The founder line has been analyzed extensively and ubiquitous and nuclear localized expression has been confirmed. In addition, breeding has demonstrated transmission of the H2B-GFP to the next generation. All animals were healthy, and multiple pregnancies have been established with progeny showing the expected Mendelian ratio for the transmission of the pH2B-eGFP. The male offspring were genotyped at birth, and those that were positive for the transgene were humanely euthanized for tissue collection, and isolation of donor cells.

For each donor and recipient animal, the swine leucocyte antigen class I (SLA-I) and class II (SLA-II) loci have been PCR amplified using primers designed to amplify known alleles in these regions based on the PCR-sequence-specific-primer strategy. The system consists of 47 discriminatory SLA-I primer sets amplifying the SLA-1, SLA-2, and SLA-3 loci[53], and 47 discriminatory SLA-II primer sets amplifying the DRB1, DQB1, and DQA loci. These primer sets have been developed to differentiate alleles by groups that share similar sequence motifs, and have been shown easily and unambiguously to detect known SLA-I and SLA-II alleles. When used together, these primer sets effectively provided a haplotype for each animal that was tested, thus providing an assay to confirm easily a matched or mismatched haplotype in donor and recipient animals.

Media and Solutions

All media were sterile-filtered (0.22 µm filter) and kept in the dark at 4° C. before use. Basal medium and fetal bovine serum (FBS) were purchased from GIBCO/Invitrogen. All growth factors were purchased from R&D Systems. All other reagents, except those noted, were obtained from Sigma.

A cell wash was formulated with 599 mls of basal medium (e.g. RPMI 1640; Gibco #11875-093) supplemented with 0.5 grams of serum albumin (Sigma, #A8896-5G, fatty-acid-free), 10-9 M selenium, and 5 mls of antibiotics (Gibco #35240-062, AAS). It was used for washing tissues and cells during processing.

Collagenase buffer was made and consists of 100 mls of cell wash supplemented with collagenase (Sigma #C5138) with a final concentration of 600 U/ml (R1451 25 mg) for biliary tree (ducts) tissue and 300 U/ml (12.5 mg) for organ-parenchymal tissue (liver, pancreas).

Kubota's medium, a defined, serum-free medium designed for endodermal stem/progenitors was used to prepare cell suspensions, organoids and HA hydrogels. This medium consists of any basal medium (here being RPMI 1640) with no copper, low calcium (0.3 mM), 1 nM selenium, 0.1% bovine serum albumin (purified, fatty-acid-free; fraction V), 4.5 mM nicotinamide, 0.1 nM zinc sulfate heptahydrate, 5 µg/ml transferrin/Fe, 5 µg/ml insulin, 10 jpg/ml high density lipoprotein, and a mixture of purified free fatty acids that are presented complexed with fatty acid free, highly purified albumin. Its preparation is given in detail in a methods review[57]. Also, it is available commercially from PhoenixSongs Biologicals (Branford, Conn.).

Soluble, long chain forms of HA (Sigma Catalog #52747) were used in stabilization of organoid cultures and in cryopreservation Those used to make the hydrogels, thiol-modified HAs, were obtained from Glycosan Biosciences, a subsidiary of Biotime. The components for these thiol-modified HAs were made by a proprietary bacterial-fermentation process using *Bacillus subtilis* as the host in an ISO 9001:2000 process (www.biopolymer.novozymes.com/). The components were produced by Novozymes under the trade name HyaCare® and are 100% free of animal-derived raw materials and organic solvent remnants. No animal-derived ingredients are used in the production, and there are very low protein levels and no endotoxins. The production follows the standards set by the European Pharmacopoeia) The HA hydrogels were prepared using Glycosil (HyStem® HAs, ESI BIO-CG313), the thiol-modified HAs, that can be trigged to form disulfide bridges using polyethylene glycol diacrylate (PEGDA). Glycosil® is reconstituted as a 1% solution of thiolated HA in 1% phosphate buffered saline (PBS) using degassed water, or, in our case, in Kubota's Medium. Upon reconstitution, it remains liquid for several hours but can undergo some gelation if exposed to oxygen. More precise gelation occurs with no temperature or pH changes if Glycosil is treated with a cross-linker such as PEGDA causing gelation to occur within a couple of minutes.

The level of cross-linking dictates the level of rigidity, and can be precisely defined by the ratio of the thiol-modified HAs to PEGDA. In prior studies, stem cell populations were tested in HA hydrogels of varying level of rigidity and were found to remain as stem cells, both antigenically and functionally (e.g. with respect to ability to migrate), only if the level of rigidity was less than 200 Pa[23]. We made use of this finding to design the grafts with a very soft layer and with more rigid layers of hyaluronan hydrogels on the serosal side to form a barrier to migration in directions other than the target tissue as well as to minimize adhesions from cells from nearby tissues. The 3 versions of the hydrogels with distinct levels of rigidity are characterized in FIG. 2, characterizations that included direct measurements of the rheological properties. The most rigid barrier, that of the 10×HA hydrogel (rigidity=760 Pa), was prepared on the backing ahead of time and could be cryopreserved if desired. At the time of the surgery, the donor cells were prepared in the soft, 1×HA hydrogel (rigidity=60 Pa); placed onto the more rigid 10× hydrogel (already on the backing); and the patch tethered to the target site. After tethering, the serosal side of the graft was coated or painted with the 2×HA hydrogel (rigidity=106 Pa) using a NORM-JECT 4010.200V0 Plastic Syringe with a BD Micro-Fine™ IV permanently attached needle.

Macro-scale rheological properties of hydrogels were determined using a stress-controlled cone-and-plate rheometer (TA Instruments, AR-G2, 40 mm cone diameter, 1° angle). Gels actively polymerized on the rheometer while oscillating at 1 rad/s frequency and 0.6 Pa stress amplitude with the modulus monitored continuously to query for sufficient completion of the cross-linking reaction. Once equilibrated, the hydrogels were subjected to an oscillatory frequency sweep (stress amplitude: 0.6 Pa, frequency range: 0.01-100 Hz). The viscoelasticity (rheological) properties of the 3 versions of hyaluronan hydrogels that were used are summarized in FIG. 2.

The most commonly used donor cells were derived from transgenic H2B-GFP pigs as described above. They offer a significant advantage for cell transplantation studies in that all cells are tagged with GFP. The use of fluorescent proteins as molecular tags enabled the donor cells to be tracked in their migration and engraftment after transplantation. This fusion protein is targeted to the nucleosomes resulting in a nuclear/chromatin GFP signal. In the described grafts, the stem cells express GFP entirely in the nucleus, but those lineage restricting to adult cell types can have it in the cytoplasm or nucleus. Note that the level of cytoplasmic GFP is especially high in the first week and is reduced with time. This is because the engraftment/invasion/integration process results in effects on the cells that can cause the H2B-linked GFP to be found cytoplasmically. This does not mean that the cells are dying but rather that they are responding to the high levels of MMPs and associated signaling that are part of the remodeling zones. Indeed, the GFP+ cells detected are clearly viable and proliferate, all expressing various adult functions (e.g. albumin, HNF4a, AFP, insulin, glucagon, or amylase).

As described in more detail in the characterizations of the grafts, autofluorescence both of the backing (spring green color) and also of lipofuscins (dark forest green color) in mature hepatocytes presented a challenge given the overlap in wavelengths with those of GFP. Therefore, Applicants shifted the GFP+ signal to a pink or rose color using an antibody to GFP and secondarily to an antibody with a red fluoroprobe. This resulted in the stem cells being recognized as small cells with pink nuclei (merger of the nuclear blue DAPI staining with the antibody-tagged-rose colored GFP+ label). Any donor cells that matured into hepatocytes were recognized as having a lavender color from the merger of the green autofluorescence (lipofuscins), the blue (DAPI), and the rose-color (GFP) (FIG. 4).

Porcine extrahepatic biliary tree tissue (gall bladder, common duct, hepatic ducts) were obtained from transgenic pigs. Tissues were pounded with a sterilized, stainless steel mallet to eliminate the parenchymal cells, carefully keeping the linkage of the intra-hepatic and extrahepatic bile ducts. The biliary tree was then washed with the "cell wash" buffer comprised of a sterile, serum-free basal medium supplemented with antibiotics, 0.1% serum albumin, and 1 nM selenium ($10^{-9}$ M). It was then mechanically dissociated with crossed scalpels, and the aggregates enzymatically dispersed into a cell suspension in RPMI-1640 supplemented with 0.1% bovine serum albumin (BSA), 1 nM selenium, 300 U/ml type IV collagenase, 0.3 mg/ml deoxyribonuclease (DNAse) and antibiotics. Digestion was done at 32° C. with frequent agitation for 30-60 minutes. Most tissues required two rounds of digestions followed by centrifugation at 1100 rpm at 4° C. Cell pellets were combined and re-suspended in cell wash. The cell suspension was centrifuged at 30 G for 5 minutes at 4° C. to remove red blood cells. The cell pellets were again re-suspended in cell wash and filtered through a 40 μm nylon cell strainer (Becton Dickenson Falcon #352340) and with fresh cell wash. The cell numbers were determined and viability was assessed using Trypan Blue. Cell viability above 90-95% was routinely observed.

In prior studies, Applicants have defined the antigenic profile of populations of mesenchymal cells that provide critical paracrine signals needed for hepatic and biliary tree stem cells versus others required for mature parenchymal cells. The mesenchymal cells that partner with BTSCs are subpopulations devoid of MHC antigens, with low side scatter, and identifiable as angioblasts (CD117+, CD133+, VEGF-receptor+, and negative for CD31), precursors to endothelia (CD133+, VEGF-receptor+, and CD31+), and precursors to stellate cells (CD146+, ICAMl+, VCAM+, alpha-smooth muscle actin (ASMA)+, and negative for vitamin A). These 3 subpopulations are referred to collectively as early lineage stage mesenchymal cells (ELSMCs). By contrast, adult hepatocytes are associated with mature sinusoidal endothelia (CD31+++, type IV collagen+, VEGF-receptor+, and negative for CD117) and those for adult cholangiocytes that are associated with mature stellate and stromal cells (ICAM-1+, ASMA+, Vitamin A++, type I collagen+).

The cell suspensions were added to Multiwell Flat Bottom Cell Culture Plates (Corning #353043) in serum-free Kubota's Medium and incubated for ~an hour at 37° C. to facilitate attachment of mature mesenchymal cells. Mature mesenchymal cells attached to the dishes within 10-15 minutes even though the medium was serum-free. The cells remaining in suspension were transferred to another dish and again incubated for up to an hour. Repeats of this resulted in depletion of a significant fraction of the mature mesenchymal cells. After depletion of mature mesenchymal cells, the remaining floating cells were seeded at $\sim 2 \times 10^5$ cells per wells in serum-free Kubota's Medium in Corning's ultralow attachment dishes (Corning #3471) and were incubated overnight at 37° C. in a CO2 incubator. Organoids comprised of the biliary tree stem cells (BTSCs) and of ELMSCs formed overnight (FIG. 1). These organoid cultures survived for weeks in Kubota's Medium, especially if the medium was supplemented (0.1%) with soluble forms of HAs (Sigma); they could also be cryopreserved as described below. From each gram of neonatal pig biliary tree tissue, we obtained $\sim 1.5 \times 10^7$ cells. We used $\sim 3-6 \times 10^5$ cells per well of a 6-well, ultra-low attachment plate and incubated in the serum-free Kubota's Medium. The cells produced, on average, 6000 to 20,000 small organoids (~50-100 cells/organoid/well). For the grafts, we used at least 100,000 organoids ($>10^7$ cells). Depending on the size of the backing, Applicants were able to increase the number of organoids in the grafts up to $10^8$ organoids (i.e. $\sim 10^9$ cells) or more embedded in ~1 ml of the soft hyaluronan hydrogel on a 3 cm×4.5 cm backing.

Isolated stem cell organoids were cryopreserved in CS10, an isotonic cryopreservation buffer containing antifreeze factors, dextran and DMSO (Bioliife, Seattle, Wash.; https://www.stemcell.com/products/cryostor-cs10.html). The viability of the cells was improved further with supplementation with 0.1% HAs (Sigma #52747). Cryopreservation was done using CryoMed™ Controlled-Rate Freezers. The viability on thawing was greater than 90%, and cells after thawing were able to attach, to expand ex vivo and in vivo and to give rise to the expected mature cells in vitro and in vivo.

Isolating the cells and assembling the grafts are characterized in a schematic in FIG. 1 and with the details summarized in FIG. 2. The grafts were formed by using a backing (TABLE 1) onto which were placed the stem cell organoids embedded in the soft hyaluronan hydrogels. These were readily prepared ahead of time and maintained in a culture dish in an incubator overnight. The grafts proved stable at the target site for the duration of the experiments. Cryopreservation of the organoids was achieved readily, but that of the organoids when within the soft hydrogel was not. This meant that embedding the organoids in the soft hydrogel had to be done just prior to surgery.

Surgeries

Anesthesia was induced by administering a combination of ketamine/xylazine (2-3 mg/kg weight each) injected IV or 20 mg/kg ketamine plus 2 gm/kg xylazine IM, and was maintained by isoflurane in oxygen administered via a closed-circuit gas anesthetic unit.

The animals were positioned in dorsal recumbency, and the ventral abdomen was clipped from xyphoid to pubis. The skin was aseptically prepared with alternating iodinated scrub and alcohol solutions. After entry into the surgery suite, preparation of the skin was repeated using sterile technique, and the area was covered with a topical iodine solution before application of sterile surgical drapes. The surgeons used appropriate aseptic technique. A mid-ventral incision was made through the skin, through subcutaneous tissues and linea alba, starting at the xiphoid process and extending caudally 8-12 cm. The left hepatic division was exposed and a 3×4.5 cm patch graft was applied to the ventral surface of the liver and containing 1×HA (~60 Pa) with embedded organoids placed onto the backing containing 10×HA (~760 Pa), and the patch was placed in direct contact onto the surface of the liver capsule. The patch graft was sutured to the liver using 4-6 simple, interrupted sutures of 4-0 polypropylene. The exposed surface of the graft was then treated with 2 mls of 2×HA hydrogel (~106 Pa), a level of rigidity that was fluid enough to permit it to be painted or coated onto the serosal side of the graft; it served to further minimize adhesions from neighboring tissues. Following placement of the surgical graft, the linea alba was closed with a simple continuous suture using 0-PDS. The linea was blocked with 2 mg/kg 0.5% bupivacaine, IM. The subcutaneous tissues and skin were closed with continuous 2-0 PDS and 3-0 Monocryl sutures, respectively. Tissue adhesive was placed on the skin surface.

The graft transplants from the transgenic pigs to the recipients were allogeneic and so required immunosuppression. The immune-suppression protocols used were ones established by others. All pigs received oral dosages of the immunosuppressive drugs Tacrolimus (0.5 mg/kg) and Mycophenolate (500 mg) twice daily, beginning 24 hours prior to surgery. The drugs were given continuously for the entire experimental period. These could be given to the animals easily if mixed with their favorite foods.

All animals were humanely euthanized at the designated time point by sedation with Ketamine/Xylazine, and isofluorane anesthesia, followed by an intravenous injection of a lethal dose of sodium pentobarbital. Upon confirmation of death, the carcass was carefully dissected, and the target organs were removed, and placed in chilled Kubota's Medium for transportation to the lab. In addition to the liver, the lungs, heart, kidney, and spleen were collected and fixed in 10% neutral formalin.

Characterization of the Grafts

After 48+ hours of fixation, tissues samples were placed in labeled cassettes in 70% ethanol and were processed on a long cycle at 60 degrees in a Leica ASP300S Tissue Processor for approximately 10 hours. After completion of the overnight processing, samples were embedded using the Leica EG1160 Embedding Station. A mold was filled with wax and the sample was placed in the correct orientation so that desired sections could be collected. The cassette was chilled until the block and tissue sample could be removed as one unit from the mold. The block was sectioned at 5 microns using a Leica RM2235 Microtome; the sections were floated in the water bath and placed onto slides. The slides were allowed to air dry overnight before staining. Sections were stained for Haematoxylin and Eosin (H&E; Reagents #7211 and #7111) or Masson's Trichrome (Masson's Trichrome Stain: Blue Collagen Kit#87019) using Richard Allan Scientific Histology Products and following the manufacturer's recommended protocol; the protocol is programed into a Leica Autostainer XL.

Tissue was embedded and frozen in OCT and flash frozen at −20° C. for frozen sectioning. Frozen sections were stained for IHC followed the protocol described above. For immunofluorescence, frozen sections were thawed for 1 hour at room temperature and then fixed in 10% buffered formaldehyde, acetone or methanol according to the antibody specifications. After fixation, sections were washed 3 times in 1% phosphate buffered saline (PBS), followed by blocking with 2.5% horse serum in PBS for 1 hour at room temperature. Primary antibodies diluted in 10% goat serum in PBS were added and incubated overnight at 4° C. The next morning, sections were rinsed 3 times with PBS and incubated with secondary antibodies diluted in 2.5% horse serum in PBS for 2 hours at room temperature. Images were taken using a Zeiss CLSM 710 Spectral Confocal Laser Scanning microscope (Carl Zeiss Microscopy). Antibodies are listed in TABLE 3.

Figure 5A:
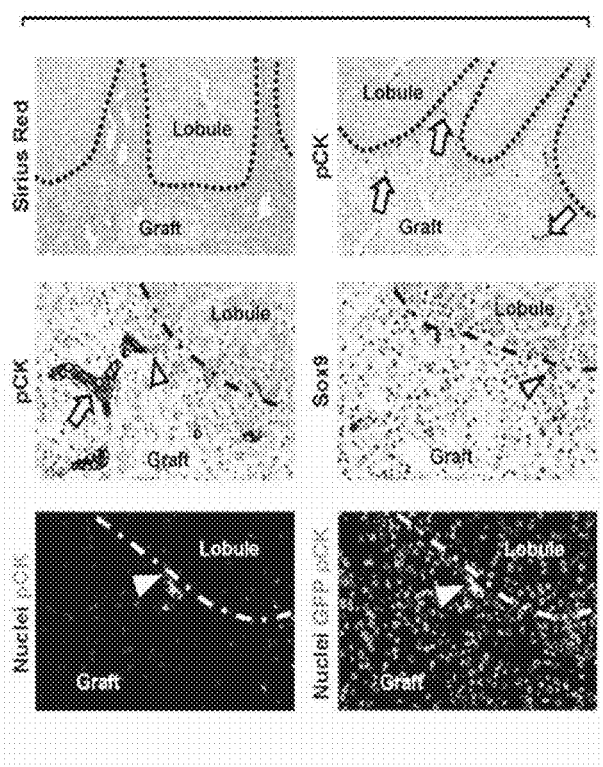
Figure 5B:
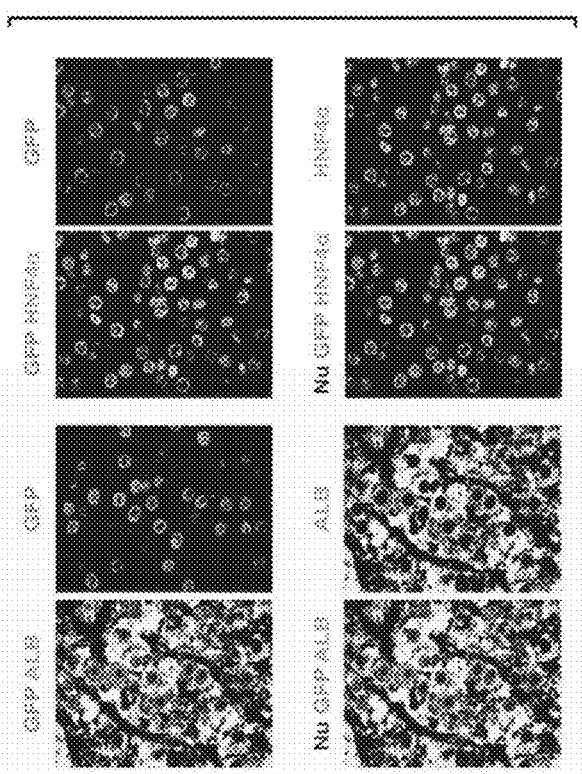

For the images in FIG. 5, sections (3 μm) were stained with hematoxylin-eosin and Sirius red, according to standard protocols. For immunohistochemistry, endogenous peroxidase activity was blocked by a 30 min incubation in methanolic hydrogen peroxide (2.5%). Antigens were retrieved, as indicated by the vendor, by applying Proteinase K (code S3020, Dako, Glostrup, Denmark) for 10 min at room temperature. Sections were then incubated overnight at 4° C. with primary antibodies (pan-Cytokeratin, Dako, code: Z0622, dilution: 1:100; Sox9, Millipore, code: AB5535, dilution: 1:200). Samples were rinsed twice with PBS for 5 min, incubated for 20 min at room temperature with secondary biotinylated antibody (LSAB+ System-HRP, code K0690; Dako, Glostrup, Denmark) and then with Streptavidin-HRP (LSAB+ System-HRP, code K0690, Dako, Glostrup, Denmark). Diaminobenzidine (Dako, Glostrup, Denmark) was used as substrate, and sections were counterstained with hematoxylin (PMID: 29248458). For immunofluorescence, non-specific protein binding was blocked by 5% normal goat serum. Specimens were incubated overnight at 4° C. with primary antibodies (chicken anti-GFP, Abcam, code: ab13970, dilution=1:200; rabbit anti-HNF4a, Abcam, code: 92378, dilution: 1:50, rabbit anti-albumin, ab2406, dilution=1:500). Specimens were washed and incubated for 1 h with labeled isotype-specific secondary antibodies (anti-chicken AlexaFluor-546, anti-mouse Alexafluor-488, anti-rabbit Alexafluor-488, Invitrogen, Life Technologies Ltd, Paisley, UK) and counterstained with 4,6-diamidino-2-phenylindole (DAPI) for visualization of cell nuclei (PMID: 26610370). For all immunoreactions, negative controls (the primary antibody was replaced with pre-immune serum) were also included. Sections were examined in a coded fashion by Leica Microsystems DM 4500 B Light and Fluorescence Microscopy (Leica Microsystems, Weltzlar, Germany), equipped with a Jenoptik Prog Res C10 Plus Videocam (Jena, Germany). Immunofluorescence stains were also analyzed by Confocal Microscopy (Leica TCS-SP2). Slides were further processed with an Image Analysis System (IAS—Delta Sistemi, Roma-Italy) and were independently evaluated by two researchers in a blind fashion. Immunofluorescence stains were scanned by a digital scanner (Aperio Scanscope FL System, Aperio Technologies, Inc, Oxford, UK) and processed by ImageScope.

Frozen sections were problematic given the high autofluorescence in hepatocytes (lipofuscin) and the fluorescence of the Seri-Silk backing. Applicants had greater success by preparing paraffin sections and staining for the GFP using a rabbit polyclonal antibody to GFP (Novus Biologicals, NE600-308); the rabbit anti-GFP antibody was used in combination with a secondary antibody of donkey anti-rabbit IgG H&L (Alexa Fluor 568; ab 175470, Invitrogen), while Donkey anti-Goat IgG Alexa Fluor 488 antibody was used to exclude non-specific staining of hepatic autofluorescence. Autofluorescence was reduced by quenching with the use of dyes and that included Trypan Blue. The Trypan Blue was used on tissues/cells at 0.4% in PBS. This reduces the background significantly.

Total RNA was extracted from the organoids or grafts using Trizol (Invitrogen). First-strand cDNA synthesized using the Primescript 1st strand cDNA synthesis kit (Takara) was used as a template for PCR amplification. Quantitative analyses of mRNA levels were performed using Faststart Universal Probe Master (Roche Diagnostics) with ABI PRISM 7900HT Sequence Detection System (Applied Biosystems). Primers were designed with the Universal Probe Library Assay Design Center (Roche Applied Science). Primer sequences are listed in TABLE 4. The primers were annealed at 50° C. for 2 min and 95° C. for 10 min, followed by 40 cycles of 95 OC (15 s) and 60° C. (1 min). Expression of glyceraldehyde-3-phosphate dehydrogenase (GAPDH) was used generally as a control and a standard.

RNA was purified from cells using the Qiagen RNeasy Kit RNA integrity (RIN) analysis was performed using an Agilent 2000 Bioanalyzer. The cDNA libraries were generated using the Illumina TruSeq Stranded mRNA preparation kit and sequenced on the Illumina HiSeq 2500 platform. Two samples were sequenced per lane, occupying a total of 8 lanes for all of the samples (one flow cell). Quality control analysis was completed using FastQ. Mapping of sequence reads to the human genome (hg19) was performed with MapSplice2 using default parameters. Transcript quantification was carried out by RSEM analysis, and DESeq was used to normalize gene expression and identify differentially expressed genes. MapSplice2 was also used to detect candidate fusion transcripts. Fusion calls were based on the depth and complexity of reads spanning candidate fusion junctions. Gene expression profiles were compared using Pearson's correlation analysis and hierarchical clustering was performed in R. Hierarchical clustering was performed following Variance Stabilizing Transformation provided in the DESeq package. Pathway enrichment analysis was performed with the Ingenuity Pathway Analysis (IPA) software.

Differential gene expression analysis was conducted only on genes with a minimum average normalized count >50 in at least one category.

Statistically significant differences between samples were calculated by using Student's 2-tailed t test and results are presented as the mean±standard deviation (SD). P values of less than 0.05 were considered statistically significant.

Results

In prior studies on injection grafting, it was found that engraftment required co-transplantation of epithelial cells with their lineage-stage-appropriate mesenchymal cell partners. For hepatic and biliary tree stem cells, these mesenchymal cells are comprised of angioblasts (CD117+, CD133+, VEGFr+, CD31-negative) and their immediate descendants, precursors to endothelia (CD133+, VEGFr+, CD31+, Van Willebrand Factor+) and precursors to stellate cells (CD146+, ICAM-1+, alpha-smooth muscle actin+ (ASMA), vitamin A-negative). Applicants refer to these collectively as early lineage stage mesenchymal cells (ELSMCs. Applicants also had partial success also with isolated porcine mesenchymal stem cells (MSCs) prepared by the methods of others and isolating cells from neonatal pig livers.

In prior studies, Applicants achieved isolating matching epithelial and mesenchymal cell stages by using multiparametric flow cytometry to determine the ratios of the lineage stage partners of epithelial and mesenchymal cells in cell suspensions and then used those ratios within grafts using immuno-selected cells. In these studies, Applicants found it more efficient to deplete cell suspensions of mature mesenchymal cells by repeated panning procedures followed by culturing remaining cell suspensions on low attachment dishes and in serum-free Kubota's Medium for 6-8 hours. Organoids self-assembled with each aggregate containing approximately 50-100 cells. Marker analyses indicated partnering of BTSCs with ELSMCs (FIG. 1). As summarized in the schematic in FIG. 1A, they were used immediately or were cryopreserved under defined conditions determined previously and thawed as needed for grafts. Organoids of BTSCs/ELSMCs were characterized using immunofluorescence (IF), qRT-PCR and RNA-seq and shown to express classic traits of BTSCs (FIG. 1) and of ELSMCs (data not shown). BTSCs in the organoids expressed no mature hepatic or pancreatic genes but low levels of pluripotency genes (e.g. OCT4, SOX2) and endodermal stem cell genes (e.g. EpCAM, SOX 9, SOX17, PDX1, LGR5, CXCR4, MAFA, NGN3 and NIS). Representative qRT-PCR assays confirmed the findings from IF and from IHC on cells prior to transplantation (FIG. 1D). IHC assays indicated that more primitive cells (e.g. ones expressing pluripotency genes) were distributed to the interiors of the organoids and later maturational lineage stages at the perimeters (e.g. cells expressing EpCAM or albumin) (FIG. 1C).

Results from patch grafts were compared with those from injection grafts with methods established previously and comprised of injection of cells and with localization to the site by triggering hyaluronans with polyethylene glycol diacrylate (PEGDA) to gel within minutes. Injection grafts into the porcine liver parenchyma resulted in essentially 100% engraftment but with minimal (if any) migration and with integration into the host tissue occurring slowly over weeks (data not shown). The findings were similar to those observed previously with injection grafts of hepatic stem cells[17]. Injection grafts into the mesentery adjacent to hepatic ducts/portal vein branches immediately caudal to the liver lobes were feasible with large ducts but caused smaller ones to occlude from the swelling effects of HA hydrogels and resulting in cholestasis (FIG. 13). Success with patch grafting led us to abandon further efforts with injection grafting strategies.

The composition of the grafts for stem cells involved use of conditions with 3 distinct layers of hyaluronans (HA) hydrogels with precise concentrations of HA to PEGDA to achieve a level of rigidity assessed by rheological assays (FIG. 2C). Donor cells were embedded into a soft HA layer (~100 Pa) and placed against the liver/pancreas surface; the soft hydrogels maintained stemness traits[23] that in these studies proved essential for engraftment. This layer was placed on top of a rigid (10x; ~700 Pa) HA layer prepared ahead of time on the backing and serving as a barrier to migration. The patch was attached to the target site with sutures or surgical glue. A 2xHA hydrogel, soft enough (rigidity=~200 Pa), to permit painting or coating the serosal surface of the graft at the time of the surgery and serving to further minimize adhesions from nearby tissues.

Patch grafts were placed onto the liver surface, i.e. superficial to the Glisson capsule or pancreatic capsule, and attached by sutures or by surgical glue at the corners (FIG. 2F). The stiffness of Seri-Silk resulted in grafts being placed at sites with minimal curvature and away from sites with significant mechanical forces (e.g. near the diaphragm). In the grafts onto pancreas, the graft was wedged between the duodenum and the pancreas.

The only variant of patch grafting attempted and then abandoned was after sharp surgical removal of the capsule. Hemorrhaging was excessive obviating future use in hosts with altered hemostasis associated with hepatic failure or even in normal hosts given the adverse influences of serum on donor cells. Without such efforts to alter the organ capsules, patch grafts proved facile for surgical procedures.

A number of backings were tried with a focus on ones used clinically in abdominal surgeries (TABLE 1 and TABLE 2). All but Seri-Silk caused problems that resulted in their elimination for further consideration. The problems included fragility (e.g. Seprafilm, Retroglyde); induction of necrosis or fibrosis and significant levels of adhesions (e.g. Surgisis, Vetrix); and severe adhesion formations with a filamentous sponge version of Seri-Silk or any of the backings supplemented with carboxymethylcellulose ("belly jelly") to the abdomen. Of the ones tested, SERI Surgical Silk[24-26] (Allergan, Inc. Irvine, Calif.) provided the best combination of mechanical support and minimal adhesions, an effect further enhanced by application of 2xHA to the serosal surface of SeriSilk after attachment to the target site. The product is a purified fibroin of Bombyx moth silk and was developed by David Kaplan (Tuft's University, Boston, Mass.). Applicants found it to be stiff, a property found useful for surgical manipulations and placement on flat/rigid organs like the liver. The stiffness made it difficult to apply to sites with significant curvature or need for flexibility. Still, its stiffness proved neutral with respect to maturational effects on the donor cells, a finding that made this backing acceptable for patch grafting. In grafts at 3 weeks, Seri-Silk was enveloped by bands of collagen, suggesting a mild foreign body reaction. Assessment of other candidate backings, such as synthetic textiles, is ongoing.

Figure 3:
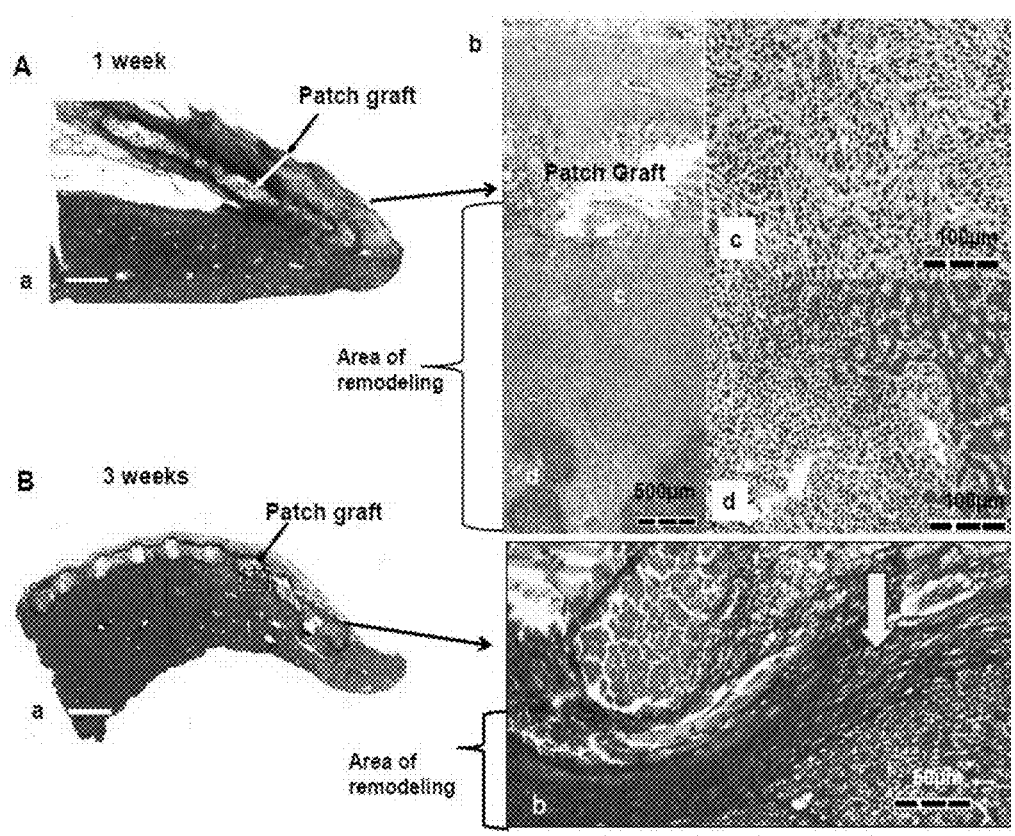
FIGS. 3A-3D depicts the result of immunohistochemistry (IHC) and histology of the liver patch grafts.
Figure 3:
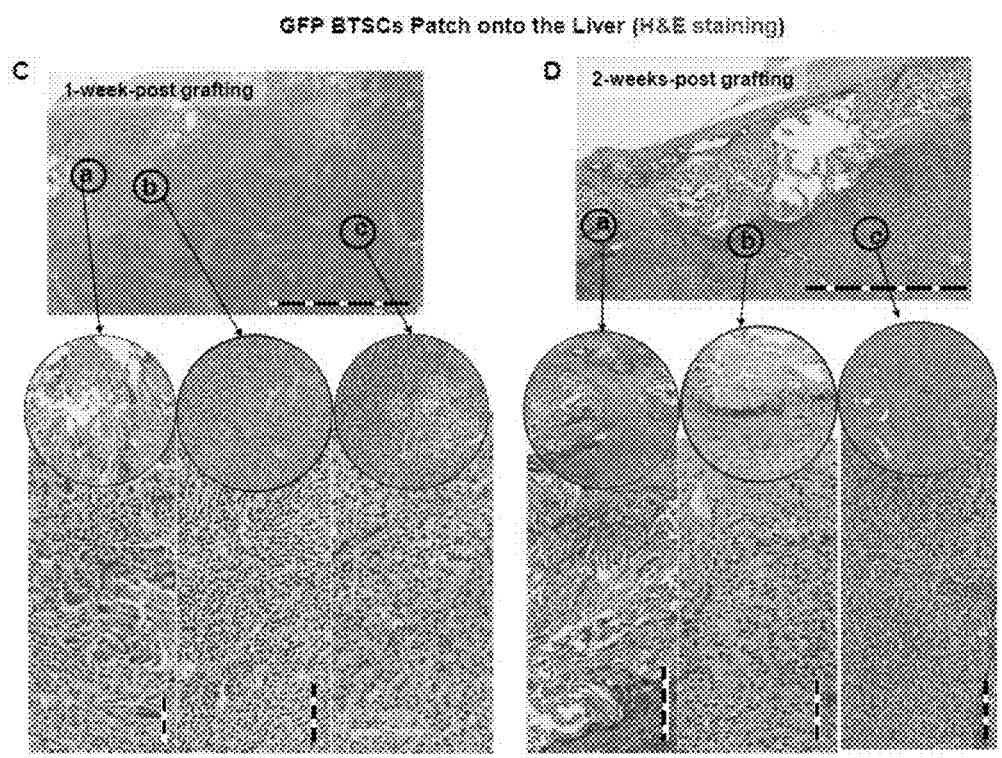

Evidence for remodeling at week one after surgery was validated with Trichrome staining (FIGS. 3, 7) or Safranin O, having dyes that stain collagens and other extracellular matrix components. The images of the graft (FIG. 3A-B) that are stained with Trichrome are compared with ones of the same site and stained with hematoxylin/eosin (FIG. 3 C-D). Reconstitution of the Glisson capsule and of the lobules occurred by 3 weeks in parallel with HAs being resorbed. The bands comprising the area of remodeling were surprisingly large (FIGS. 3-5, 7).

Donor cells deriving from transgenic GFP+ pigs were identified readily by GFP expression through IHC assays. In pancreas, the donor cells were identified by the green fluorescence. However, in liver, the autofluorescence of the lipofuscins in hepatocytes peaks at a wavelength overlapping with that for GFP. Therefore, we identified donor cells in livers with an antibody to GFP (Rabbit anti-GFP antibody; Novus, NB600-308) and coupled to a secondary antibody with a red fluoroprobe (Donkey anti-rabbit 555, Invitrogen) causing donor cells to have pink nuclei (the red fluoroprobe plus the blue DAPI). Host cells were recognized given their blue nuclei (DAPI stain) but without GFP expression (FIG. 4).

Figures 4A, 4B, 4C:
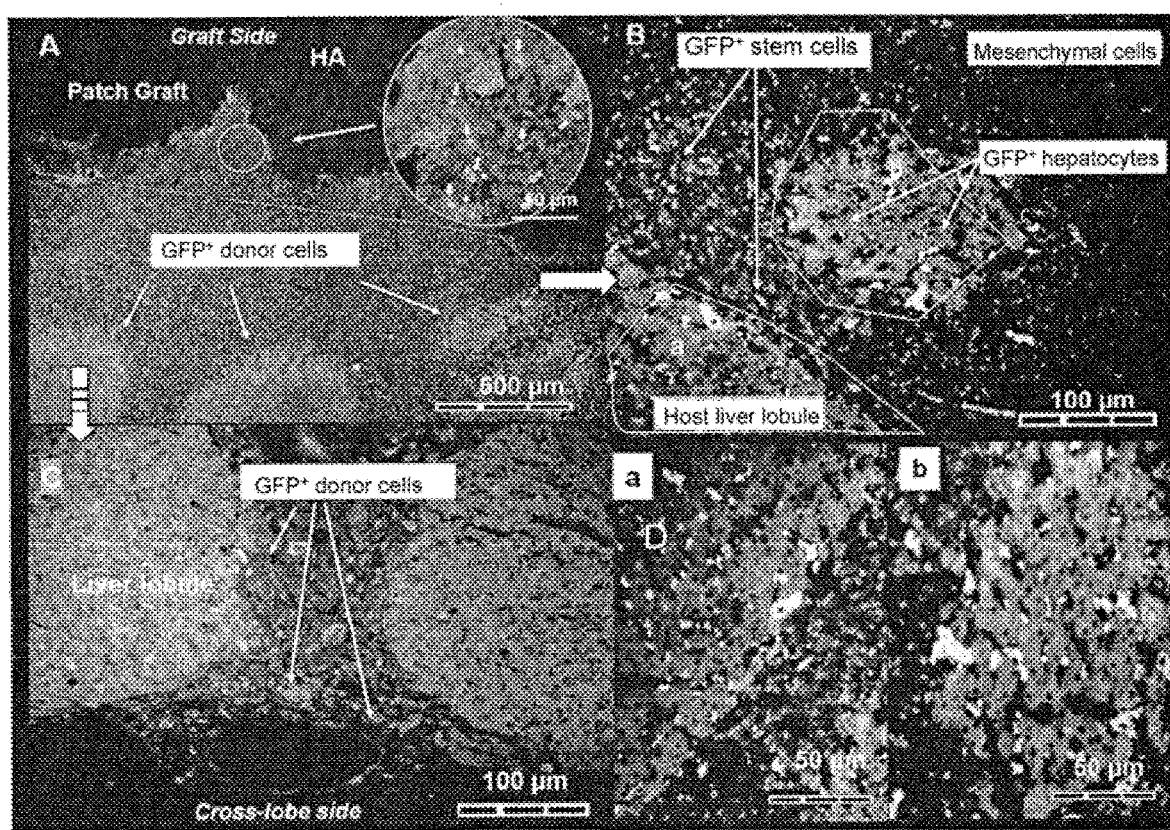
FIGS. 4A-4C shows engraftment, migration and rapid maturation to adult fates within a week.

The liver lobules of mature hepatocytes were forest-green from the autofluorescence (lipofuscins) (FIG. 4B). Donor GFP+ cells that had matured to aggregates of hepatocytes were a lavender color and with pink nuclei (FIG. 4C) due to the merger of the red fluoroprobe from GFP, the blue from DAPI, and the autofluorescent dark green from lipofuscins. Hepatocytes, whether host or donor derived, were clustered around by host mesenchymal cells (endothelia, stellate cells) with bright yellow/green autoflorescence due, we assume, to vitamin A in the mature stellate cells (FIG. 4C); the IHC data for the endothelia and stellate cells are not shown.

Figures 6A, 6B:
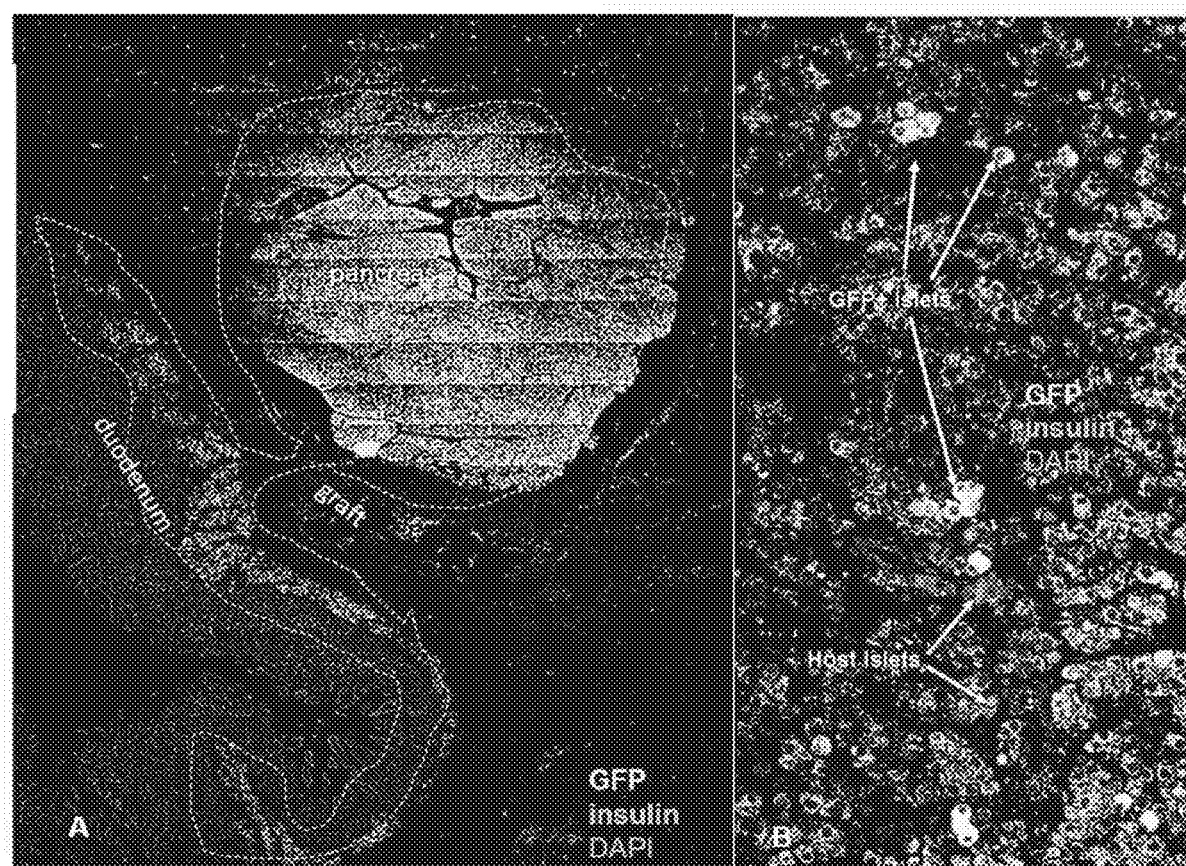
FIGS. 6A-6D provides information about patch grafts of stem cell organoids tethered to pancreas.
Figures 6C, 6D:
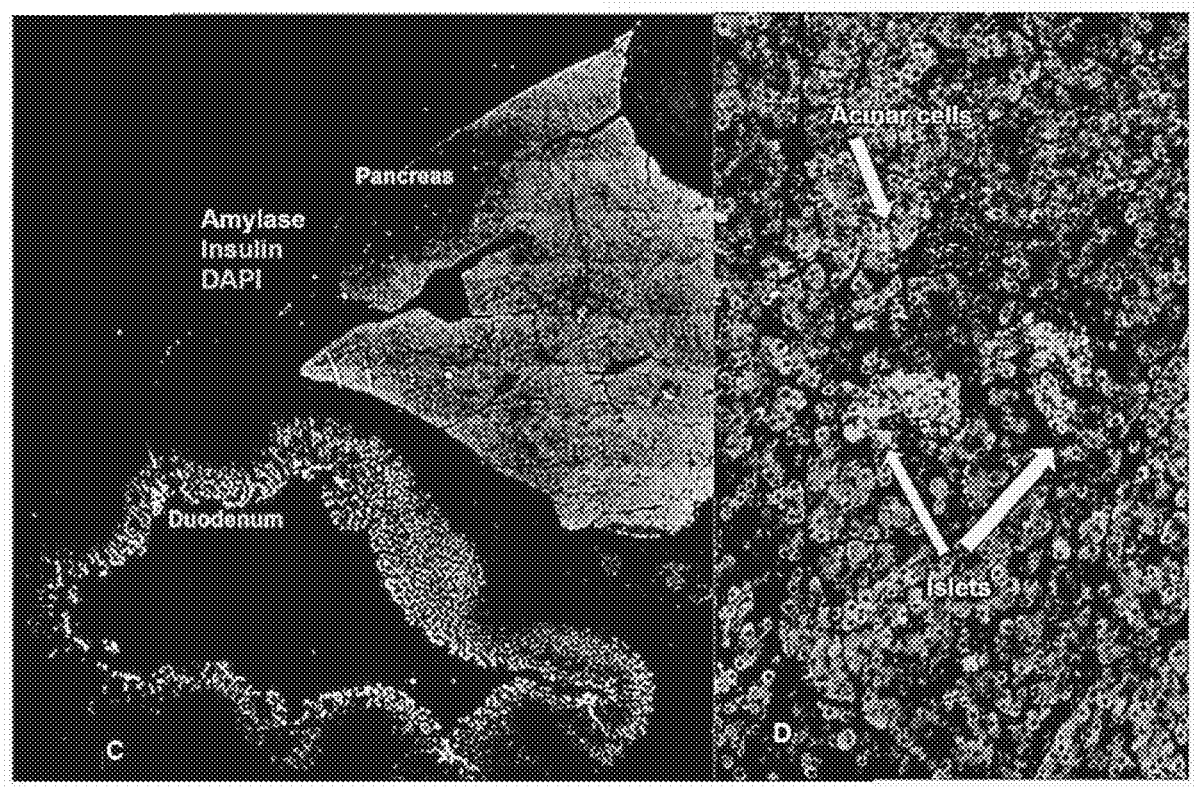
Figure 9A:
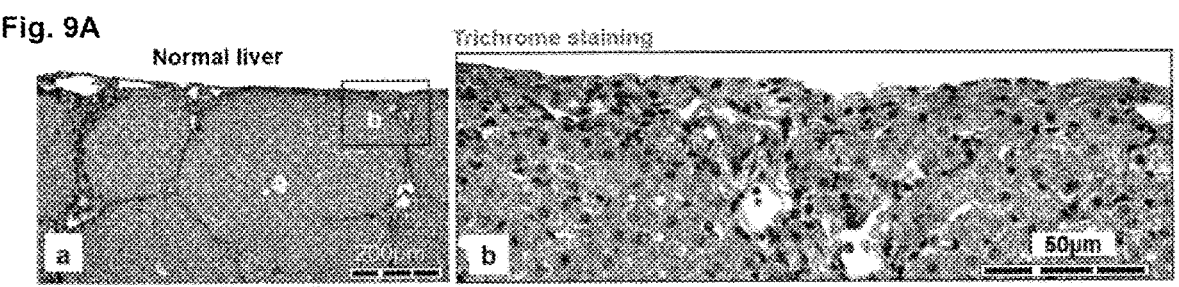
FIGS. 9A-9E provides information about patch grafts of mature (adult) hepatocytes partnered with mature mesenchymal cells (MMCs), such as endothelia or stellate cells. These patch grafts were unable to engraft. Engraftment was achievable if the hepatocytes were partnered with early lineage stage mesenchymal cells (ELSMCs), here being porcine mesenchymal stem cells (MSCs). If presented with ELSMCs, then engraftment occurred but with restriction to regions near to the graft.
Figure 9B:
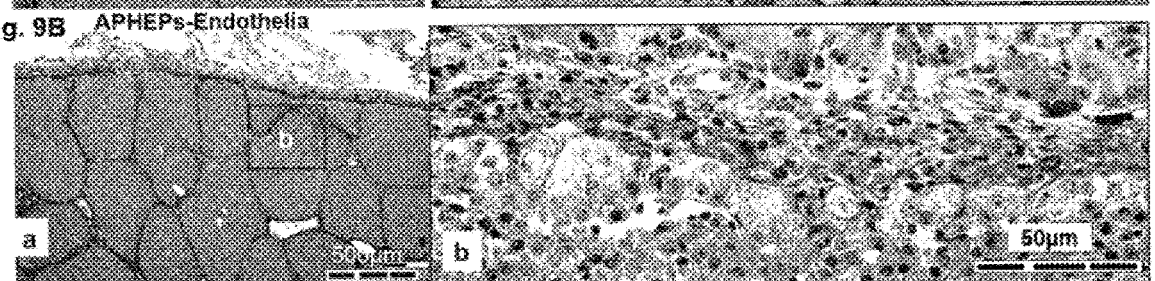
Figure 9C:
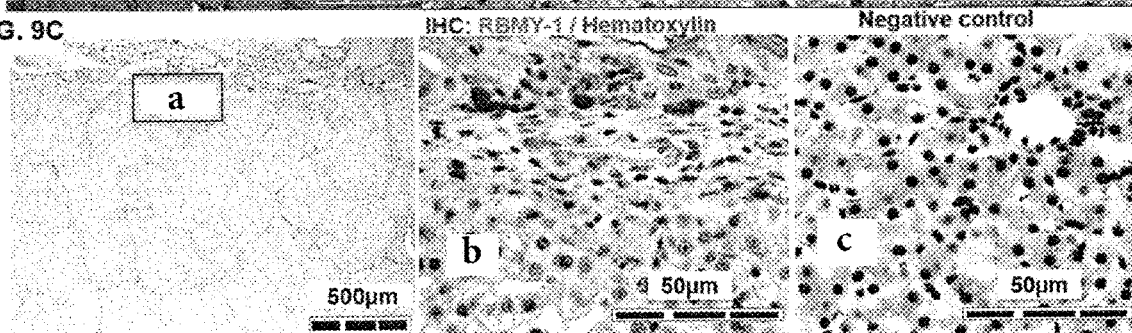
Figure 9D:
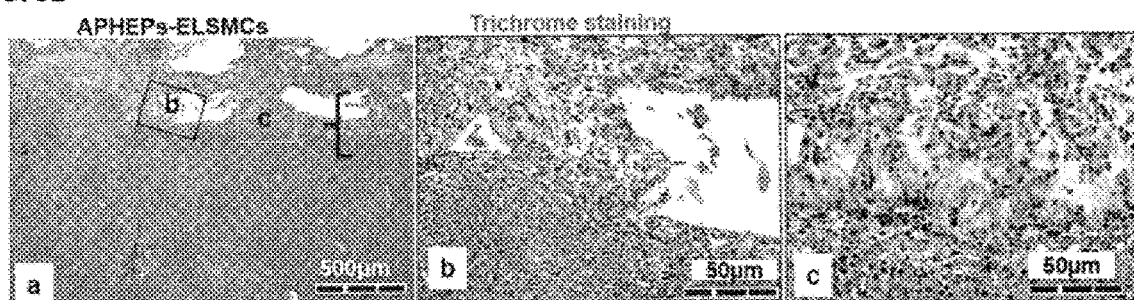
Figure 9E:
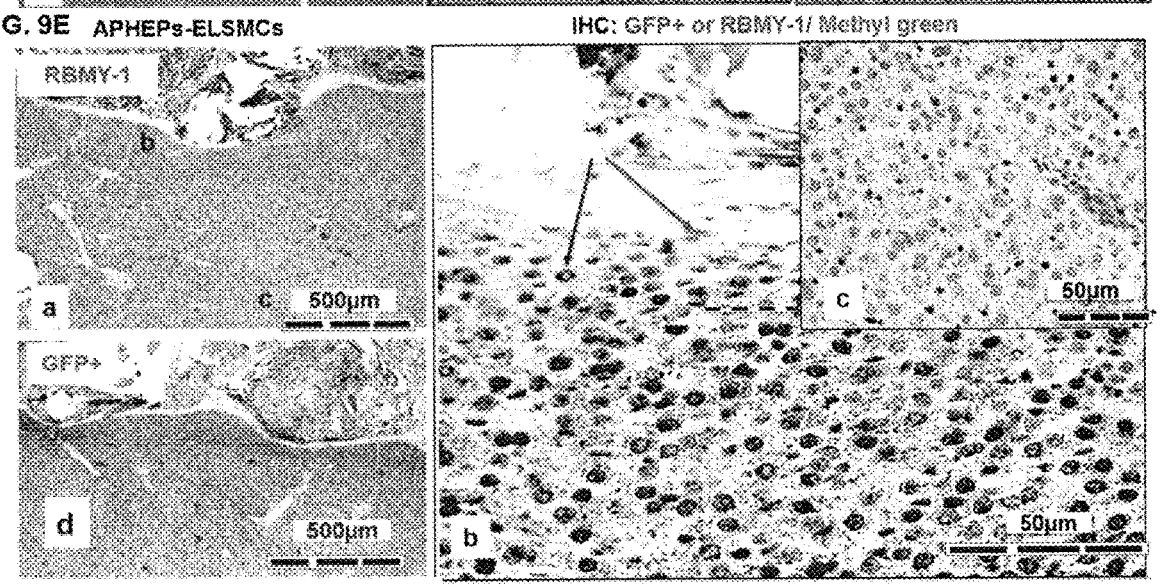
Figure 15:
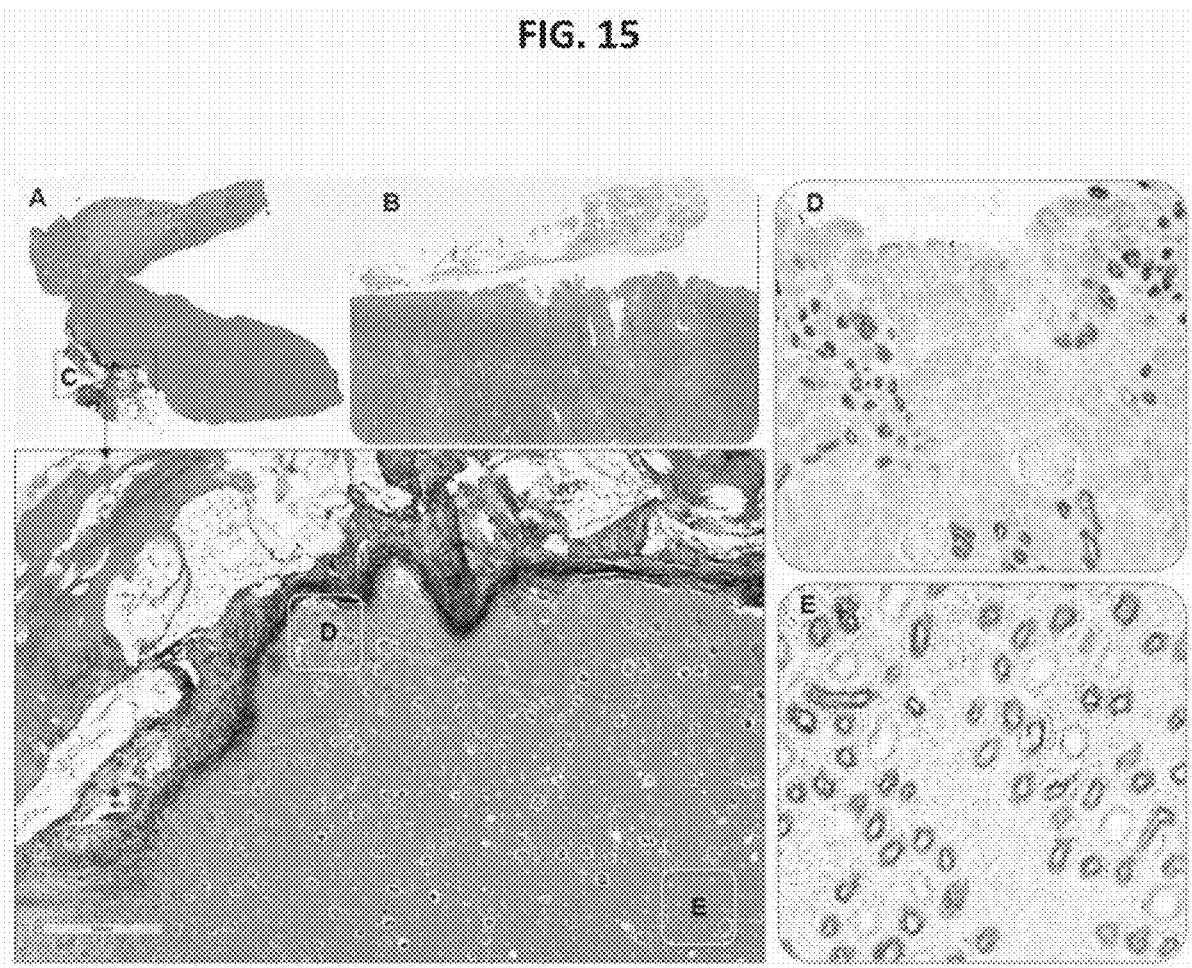
FIG. 15 (Panels A-E) shows organoids of H2B-GFP+ BTSCs/ELSMCs patch grafted onto the Kidney. Evaluation was done at 1-week-post-grafting. Panel A shows Trichrome staining of grafted kidney. The kidney was prepared in cross-section to expose the deeper layer that with the graft as a "V" shape. The lower half "V" with bright blue staining is the graft side on the kidney; the upper "V" in the figure is a deeper layer to the grafted layer. Panel B shows H&E staining for the same section of the grafted kidney. Panel C is the higher magnification of the patch grafted kidney. The capsule of the kidney under the graft was loosened (from dissolution by MMPs) in a fashion similar to that in the liver. Panel D shows IHC staining of GFP+ cells (dark red) that have engrafted into the kidney at a layer under the patch. Panel E shows engraftment of the GFP+ cells (dark red) at deeper layers of the kidney. Necropsy reports indicated that there was no necrosis found in the grafted kidney or elsewhere in the animals that were subjected to patch grafts.

Within a week, patch grafts of BTSCs/ELSMCs organoids resulted in remodeling of the organ capsule and adjacent lobules followed by a merger of host and donor cells (FIGS. 3-5, 7). Finger-like extensions of donor cells extended into the hepatic lobules of the host tissue; in parallel, host cells extended into HAs of the grafts (FIG. 4). In the case of the pancreas, the graft was wedged between the pancreas and the duodenum, and by one week post surgery, engraftment of donor cells occurred both into the pancreas and into the Brunner's glands of the submucosa of the duodenum (FIG. 6). Integration of the cells within large regions of the liver (or the pancreas) was completed by 2 weeks by which time the layers of HAs had been mostly resorbed; donor cells had lineage restricted into adult hepatic parenchymal fates, both cholangiocytic and hepatocytic (FIG. 5) or into pancreatic fates (FIG. 6).

By 3 weeks, the HA layers were resorbed entirely, leaving only the backing. This correlated with reappearance of the organ capsule and of the histological structure of the tissue near to the capsules (FIGS. 3, 5, 6) or of the pancreatic capsule and of the pancreatic histological structures (FIG. 6). In pancreas, mature cells were identified by functional markers that included insulin for islet cells (beta cells) and amylase for acinar cells.

Engraftment efficiency for both the liver and for the pancreas was close to 100% by a week, since all donor cells identified were found to be viable and within the liver or pancreas; not in the remnants of the grafts above the organ capsules; and with negligible or no evidence of ectopic cell distribution in other organs (e.g. lung).

The speed of migration of donor cells in the BTSC/ELSMC grafts through the liver and through the pancreas proved remarkable resulting in donor cells in most regions of the organ (liver or pancreas) by the end of a week and with uniformly dispersed cells throughout the tissue (liver/pancreas) by 2-3 weeks (FIGS. 3-6).

Correlated with the dissolution and remodeling of the Glisson capsule (or pancreatic capsule) and neighboring liver lobules (or pancreatic tissue) and correlating with significant engraftment was elevated expression of multiple MMPs, enzymes known to dissolve extracellular matrix components and to be associated with cell migration. In FIG. 7 are summarized data from RNA-seq studies and IHC assays on MMPs expressed by stem/progenitors versus adult cells. BTSCs expressed high levels of multiple MMPs, comprised of both secreted forms (e.g. MMP2, MMP7) as well as membrane-associated forms (e.g. MMP14 and MMP15). The ELSMCs, precursors of endothelia and of stellate cells, also contributed to multiple MMPs.

The findings from RNA-seq data were confirmed by IHC assays for the proteins encoded by MMP genes (FIG. 7). IHC assays confirmed the presence of the secreted forms of MMPs (e.g. MMP1, MMP2, MMP7, MMP9) especially in the regions of remodeling. Protein expression of MMP1 was found in BTSCs/ELSMCs organoids and also in remodeling regions of grafts; however, existing data banks of RNA-seq findings do not include MMP1 because of a lack of an annotated species of porcine MMP1 to be used for the analyses. Therefore, recognition of its expression is based on IHC assays.

Variables causing differentiation of donor cells resulted in a muting of expression of MMPs, especially the secreted forms, and, in parallel, a loss in potential for engraftment and migration (data not shown). These factors included serum, various soluble regulatory signals (growth factors, cytokines, hormones) known to influence differentiation of the donor cells, extracellular matrix components whether in the hydrogels or in the backings (especially type I collagen-containing backings), and the stiffness of the HA hydrogels (i.e. the Pa levels). If differentiation of the ELSMCs progressed preferentially to stroma, the grafts became fibrotic; if to endothelia, the grafts retained viable cells and tissue but remained superficial to the organ capsule (data not shown).

Organoids of BTSCs/ELSMCs proved the most successful arrangement for the cells for grafting. In the past, we had co-transplanted epithelial-mesenchymal partners by immuno-selecting them from cell suspensions by flow cytometry using their distinctive surface antigens, and then mixing them according to the ratios found in cells suspensions from freshly isolated tissues[17]. Here we found that letting them self-select into organoids, after removal by panning of mature mesenchymal cells, proved more efficient and effective in establishing lineage-stage appropriate epithelial-mesenchymal partners with relevant paracrine signaling for the grafts and yielding organoids under defined (serum-free) conditions, that made them easily and safely cryopreserved.

The primary design of the grafts consisted of mixing of cells with appropriate biomaterials that can become insoluble and keep cells localized to the target site. For grafts, the ideal biomaterials proved to be non-sulfated or minimally sulfated glycosaminoglycans (GAGs), such as hyaluronans (HAs), found in all stem cell niches, with receptors to HAs being classic stem cell traits. Maintenance of cells as stem/progenitors optimized expression of secreted and membrane-associated MMPs effective for engraftment.

Evidence of engraftment processes was particularly dramatic within regions of remodeling that occurred at the interface of the graft and the host tissue. To validate the findings of remodeling, Trichrome staining and Safranin O were used having dyes that stain extracellular matrix components and analyzed in parallel with adjacent sections stained with hematoxylin/eosin (FIG. 3, 7). It confirmed remodeling of the organ capsule and of adjacent tissue within a week after surgery. By 3 weeks post-surgery, these assays demonstrated reconstitution of the organ capsules and of the normal tissue histology following clearance of HAs. The remodeling zone was surprisingly large (FIG. 3, 7), especially at one week after surgery and was shown to involve multiple forms of MMPs (FIG. 7)

Although there are many sources and types of HAs, among the most useful are thiol-modified ones established by Glenn Prestwich (University of Utah, Salt Lake City, Utah) and that can be triggered with PEGDA to form a hydrogel with precise biochemical and mechanical properties. These properties of HAs confer perfect elasticity, allow access into the graft of all soluble signals in blood, lymph or interstitial fluid, and minimize the maturation of donor cells until engraftment and migration have occurred. The ability to vary the rheological factors with simple changes in HA and PEGDA concentrations provided additional advantages in guiding the direction of migration of the cells and in minimizing adhesions. Soft HA hydrogels, ones mimicking properties in stem cell niches, were permissive for expression of the stem/progenitor cell-associated repertoire of MMPs. Thus, the mechanical properties of HAs, studied for years in the functions of skeletal tissues, are important also in managing grafting strategies[23].

Patch grafts containing stem/progenitors resulted in a striking phenomena of grafts "melting" into tissues within a few days, followed by a merger of donor and host cells, and a distribution of cells throughout most regions of the organ by one to two weeks. Thereafter, maturation of donor cells and restoration of the organ capsules occurred in parallel with the tissue clearance of HAs.

The engraftment and integration process correlated with expression of multiple MMPs, a family of calcium-dependent, zinc-containing endopeptidases that degrade extracellular matrix components. Using RNA-seq studies, we found a pattern of stem/progenitor-associated MMPs, comprised of high levels of secreted forms (e.g. MMP2, MMP7) as well as membrane-associated forms (e.g. MMP14, MMP15). IHC assays indicated that protein levels of secreted MMPs (e.g. MMP1, MMP2, MMP7) were found richly expressed in areas of remodeling (FIG. 7). Conditions (soluble growth factors, cytokines, serum, matrix components, mechanical forces) that caused donor cells to differentiate resulted in reduction in MMPs, especially the secreted forms, and, in parallel, abrogation of the engraftment process.

The biomaterials of the grafts, especially the HAs, have been shown ex vivo and in vivo to maintain stemness traits in cells. Since the grafts are devoid of known signals that can trigger fate determination, the findings of donor cells that had matured into distinct adult fates, depending whether the graft was placed onto the liver or the pancreas, implicate the local microenvironment of the host tissue as the logical source of relevant factors for the maturational processes.

The numbers of cells that can be engrafted are considerable ($>10^8$) and dictated by the dimensions of the graft, the numbers of cells, and the repertoire of secreted and plasma-membrane-associated MMPs. These findings are in contrast to the limited numbers of cells (e.g. $10^5$-$10^6$) feasible with vascular delivery or by injection grafting.

Patch grafting is a safe strategy by which to transplant large numbers of cells into a solid organ, including internal organs, and may prove useful for treatment of patients especially if engraftment can occur sufficiently under disease conditions. Although, there is concern that aberrant engraftment may occur where tissue is fibrotic or affected by cirrhosis. Accordingly, examples are provided herein to determine efficacy of patch grafts for the method aspects.

Example 2: Treatment of Liver Disease

This example describes an exemplary method of treating a subject having a liver disease or disorder using a patch graft. Donor cells are prepared as organoids of biliary tree stem cells (BTSCs), precursors to liver and to pancreas, aggregated with early lineage stage mesenchymal cells (ELSMCs) consisting of angioblasts and their early lineage stage descendants, precursors to endothelia and precursors to stellate cells as described herein. The BTSC/ELSMCs organoids are embedded into soft hyaluronan hydrogels (<200 Pa) placed onto a backing that is tethered to a target site of the subject's liver.

Following administration of the patch graft, the subject is monitored for improvement in liver function. Commonly used tests to check liver function include but are not limited to the alanine transaminase (ALT), aspartate aminotransferase (AST), alkaline phosphatase (ALP), albumin, and bilirubin tests. The ALT and AST tests measure enzymes that are released by the liver in response to damage or disease. The albumin and bilirubin tests measure how well the liver creates albumin, a protein, and how well it disposes of bilirubin, a waste product of the blood. It is expected that after about 2 weeks to about 36 weeks, an improvement in liver function will be detected. Improvement is determined by detecting an improved value of one or more of the liver function tests relative to the value prior to administration of the graft and/or an improvement or amelioration of one or more symptoms of the liver disease or disorder.

Example 3: Treatment of Pancreatic Disease

This example describes an exemplary method of treating a subject having a disease or disorder of the pancreas using a patch graft. Donor cells are prepared as organoids of biliary tree stem cells (BTSCs), aggregated with early lineage stage mesenchymal cells (ELSMCs) consisting of angioblasts and their early lineage stage descendants, precursors to endothelia and precursors to stellate cells as described herein. The BTSC/ELSMCs organoids are embedded into soft hyaluronan hydrogels (<200 Pa) placed onto a backing that is tethered to a target site of the subject's pancreas.

Following administration of the patch graft, the subject is monitored for improvement in pancreatic function. Commonly used tests to check pancreatic function include but are not limited to blood tests for levels of the pancreatic enzymes amylase and lipase, the direct pancreatic function test following administration of secretin or cholecystokinin, fecal elastase test, CT scan with contrast dye, abdominal ultrasound, endoscopic retrograde cholangiopancreatography (ERCP), endoscopic ultrasound, and magnetic resonance cholangiopancreatography. It is expected that after about 2 weeks to about 36 weeks, an improvement in pancreatic function will be detected. Improvement is determined by detecting an improved value of one or more of the pancreatic function tests relative to the value prior to administration of the graft and/or an improvement or amelioration of one or more symptoms of the disease or disorder of the pancreas.

Example 4: Treatment of Kidney Disease

This example describes an exemplary method of treating a subject having a disease or disorder of the kidney using a patch graft. Donor cells are prepared as organoids of biliary tree stem cells (BTSCs), aggregated with early lineage stage mesenchymal cells (ELSMCs) consisting of angioblasts and their early lineage stage descendants, precursors to endothelia and precursors to stellate cells as described herein. The BTSC/ELSMCs organoids are embedded into soft hyaluronan hydrogels (<200 Pa) placed onto a backing that is tethered to a target site of the subject's kidney.

Following administration of the patch graft, the subject is monitored for improvement in kidney function. Commonly used tests to check pancreatic function include but are not limited to clinically relevant endpoints of kidney function known in the art. It is expected that after about 2 weeks to about 36 weeks, an improvement in kidney function will be detected. Improvement is determined by detecting an improved value of one or more of the kidney function tests relative to the value prior to administration of the graft and/or an improvement or amelioration of one or more symptoms of the disease or disorder of the kidney.

Example 5: Treatment of GI Disease

This example describes an exemplary method of treating a subject having a gastrointestinal disease or disorder using a patch graft. Donor cells are prepared as organoids of biliary tree stem cells (BTSCs), aggregated with early lineage stage mesenchymal cells (ELSMCs) consisting of angioblasts and their early lineage stage descendants, precursors to endothelia and precursors to stellate cells as described herein. The BTSC/ELSMCs organoids are embedded into soft hyaluronan hydrogels (<200 Pa) placed onto a backing that is tethered to a target site of the subject's intestines.

Following administration of the patch graft, the subject is monitored for improvement in intestinal function. Commonly used tests to check intestinal function include but are not limited clinically relevant endpoints of intestinal function known in the art. It is expected that after about 2 weeks to about 36 weeks, an improvement in intestinal function will be detected. Improvement is determined by detecting an improved value of one or more of the intestinal function tests relative to the value prior to administration of the graft and/or an improvement or amelioration of one or more symptoms of the gastrointestinal disease or disorder.

TABLE 1

| Index | Surgical Approach 1 | Surgical Approach 2 | Surgical Approach 3 | Surgical Approach 4 |
|---|---|---|---|---|
| Details for treatment | Patch graft directly on liver surface | Direct injection into liver parenchyma | Periductal injection at ductal bifurcation | Direct injection under the capsule around the bile ducts (e.g. common bile duct) |
| Animal in group | n = 23 | N = 3 | N = 3 | N = 3 |
| Cells per grafts* | 0.5~5E7 per ml | 0.5-5E7 per ml by multiple Injections | 0.5-2E7 per 0.5 ml | 0.5-2E7 per 0.5 ml |
| Outcomes | Good | Good | Good, but limited | Bad. |
| Limitations/ contraindications | Safe for normal liver and for injured animal, efficient for delivery of large number of donor cells into the liver; The components of patch grafts can be adapted due to the stages of liver dysfunctions | Cell numbers/per injection are limited**; multiple injections might cause higher risk of bleeding. | Cell numbers per injection are limited due to limitation of proper injection sites in hosts. Multiple injections can not be achieved. | Resulted in occlusion of ducts and subsequent cholestasis symptoms. |
| Indications for Application | Any liver dysfunctions, especially inborn errors of metabolism | Potential to be used for inborn errors of metabolism and early stage cirrhosis | Recommended for left lobe grafts | Not recommended |

*Cells per grafts are cell numbers per ml cross-linked HA
**In this study, for 10 kg BW healthy piglets recipient, no more than 0.5 ml per injection was found tolerated.

TABLE 2

Comparison of Backings tested for Patch Grafts

| Backings | Ease in handling | Adverse reactions | Adhesions | Information on backing |
|---|---|---|---|---|
| SERI ® Surgical Scaffold Silk | Yes | No | Minimal* | Bombyx Moth Silk David Kaplan (Tuft's University, Boston, MA), Sofragen (Boston, MA) |
| Vetrix BioSIS ECM | Yes | Tended to become dislodged and to fold over, Necrosis, Discoloration, Fibrosis | 2-3 | Regenerative Medicine Tech. |
| Surgisis ® ES ™ Soft Tissue Graft | Yes | | 2-3 | www.cooksurgical/1470 |
| Alloderm | Yes | | 2-3 | Decellularized tissue from human dermis |
| Vicryl Knitted Mesh | Yes | | Severe | Ethicon |

TABLE 2-continued

Comparison of Backings tested for Patch Grafts

| Backings | Ease in handling | Adverse reactions | Adhesions | Information on backing |
|---|---|---|---|---|
| Seprafilm | Too fragile | No | 2 | https://www.seprafilm.us/ |
| Reglyde | Too fragile | No | 2 | http://www.biotimeinc)com/technologies/hystem-hydrogels/ |

**Adhesions: These ranged in extent of severity. We assigned a number to indicate that severity: 0 = no adhesions; 1 = thin and easily disrupted adhesions; 2 = adhesions requiring blunt force dissection to disrupt; 3 = Dense adhesions that were dispersed only with the use of considerable force, resulting in partial or total injury to the viscera.

*The filamentous sponge version of Seri-Silk caused significant adhesions. Most severe adhesions observed with any of the backings used in combination with "belly jelly", carboxymethylcellulose. Coating of serosal surface of backing with more concentrated HA reduced and minimized adhesions Immunosuppression. All pigs received oral dosages of the immunosuppressive drugs Tacrolimus (0.5 mg/kg) and Mycophenolate (500 mg) twice daily, beginning 24 hours prior to surgery, and continuously given thorough the post-surgical period.

TABLE 3

Antibodies

| Category | Antibody | Host | Clonality/Conjugation | Isotype | Supplier | Catalogue Number | Dilution/Application |
|---|---|---|---|---|---|---|---|
| Primary Antibodies | | | | | | | |
| Pluripotent | OCT4 | Gt | Poly, non-conjugated | IgG | Santa Cruz Biotechnology | SC-9081 | IHC-P (1:100) |
| Multipotent endoderm | EpCAM | Rb | Poly, non-conjugated | IgG | Abcam | ab71916 | IHC-P (1:200) IF (1:200) |
| | SOX9 | Rb | Poly, non-conjugated | IgG | Chemicon | AB5535 | ICC (1:800) IF (1:500) |
| | PDX1 | Gt | Poly, non-conjugated | IgG | R&D System | AF2419 | IHC-P/ICC (1:200) IF (1:50) |
| | NIS | Ms | Mono-C#: SPM186 | IgG1 | Abcam | ab17795 | IHC-P/ICC (1:50) |
| | SOX17 | Ms | Mono-C#: OTI3B10 | IgG1 | Abcam | ab84990 | IHC-P (1:100) IF/ICC (1:50) |
| Y chromosome | RBMY1 | Rb | Poly, non-conjugated | IgG | Santa Cruz Biotechnology | sc-28727 | IHC-P (1:400) |
| GFP | GFP | Rb | Poly, non-conjugated | IgG | Novus Biologicals | NB600-308 | IHC-P (1:500) IF (1:200) |
| GFP-555 | GFP Tag | Rb | Poly, Alexa-555 | IgG | Thermo Fisher Scientific | A-31851 | IF-P/IF-F/ICC (1:350) |
| Pancreatic markers | Insulin | Gp | Poly, non-conjugated | IgG | Abcam | Ab195956 | IF (1:100) |
| | Glucagon | Ms | Mono | IgG1 | Sigma-Millipore | G2654 | IF (1:100) |
| | alpha-Amylase | Rb | Poly, non-conjugated | | Sigma-Millipore | A8273 | IF (1:200) |
| Matrix Metalloproteinases | MMP1 | Gt | Poly, non-conjugated | IgG | Sigma-Millipore | M4696-100UG | 10 µg/mL |
| | MMP 2 (C-terminal) | Ms | Mono-C#: 6E3F8 | IgG | Abcam | ab86607 | IHC-P (1:300) |
| Secondary Antibodies | | | | | | | |
| Fluorogenic assay (Cross Adsorbed) | Anti-Gt-488 | Dk | Poly, DyLight 488 | IgG (H + L) | Thermo Fisher Scientific | SA5-10086 | 1:1000 |
| | Anti-Rb-594 | Dk | Poly, DyLight 594 | IgG (H + L) | Thermo Fisher Scientific | SA5-10040 | 1:1000 |
| | Anti-Ms-488 | Dk | Poly, DyLight 488 | IgG (H + L) | Thermo Fisher Scientific | SA5-10166 | 1:1000 |
| | Anti-Gt-350 | Dk | Poly, DyLight 350 | IgG (H + L) | Thermo Fisher Scientific | SA5-10085 | 1:1000 |
| | Anti-Rb-488 | Dk | Poly, Alexa Fluor 488 | IgG (H + L) | Thermo Fisher Scientific | A21206 | 1:400 |
| | Anti-Gp-647 | Dk | Poly, Alexa Fluor 647 | IgG (H + L) | Jackson Immuno Research | 706-605-148 | 1:400 |
| | Anti-Ms-594 | Dk | Poly, Alexa Fluor 594 | IgG (H + L) | Thermo Fisher Scientific | A21207 | 1:400 |
| Chromogenic assay | Anti-Rb Detection Kit | Hs | Micropolymer HRP | IgG | Vector laboratories | MP-7401 | Ready-to-use |
| | Anti-Ms Detection Kit | Hs | Micropolymer HRP | IgG | Vector laboratories | MP-7402 | Ready-to-use |

TABLE 3-continued

Antibodies

| Category | Antibody | Host | Clonality/Conjugation | Isotype | Supplier | Catalogue Number | Dilution/Application |
|---|---|---|---|---|---|---|---|
| | Anti-Gt Detection Kit | Hs | Micropolymer HRP | IgG | Vector laboratories | MP-7405 | Ready-to-use |
| | Anti-Ms Detection Kit | Hs | Micropolymer HRP | IgG | Vector laboratories | MP-7402 | Ready-to-use |

Abbreviations
Host: Gt, goat; Rb, rabbit; DK, donkey; Hs, horse; Ms, mouse; Gp, Guniea Pig
Clonality or Conjugation: Poly, polyclonal Mono-C #, monoclonal clone number
Application: IHC, immunohistochemistry IHC-F, immunohistochemistry-frozen sections IHC-P, immunohistochemistry-paraffin embedded samples ICC, immunocytochemistry IF, immunofluorescence HRP, horseradish peroxidase

TABLE 4

Primers (qPCR)

| Category | Name | Accession Number | Sequence (5' to 3') | Length (bp) | Tm (° C.) |
|---|---|---|---|---|---|
| Housekeeping gene | GAPDH | NM_001206359.1 | Sense: ATCCTGGGCTACACTGAGGAC<br>Anti-sense:. AAGTGGTCGTTGAGGGCAATG | 473 | 63° C. |
| Pluripotent genes | Nanog | NM_001129971.1 | Sense: TTCCTTCCTCCATGGATCTG<br>Anti-sense: ATCTGCTGGAGGCTGAGGTA | 214 | 62° C. |
| | Sox2 | NM:_001123197 | Sense: GCCCTGCAGTACAACTCCAT<br>Anti-sense: GCTGATCATGTCCCGTAGGT | 216 | 60° C. |
| | Oct4 | JN633978.1 | Sense: CGAAGCTGGACAAGGAGAAG<br>Anti-sense: GCTGAACACCTTCCCAAAGA | 176 | 60° C. |
| Endodermal primitive genes | EpCAM | NM_214419.1 | Sense: ACCAGAGAATGCTATCCAGAAC<br>Anti-sense: CTCACTCGCTCCAAACAGG | 314 | 53° C. |
| | Lgr5 | NM_001315762.1 | Sense: CCTTGGCCCTGAACAAAATA<br>Anti-sense: ATTTCTTTCCCAGGGAGTGG | 110 | 60° C. |
| | Sox9 | NM_213843.2 | Sense: CGGTTCGAGCAAGAATAAGC<br>Anti-sense: GTAATCCGGGTGGTCCTTCT | 229 | 60° C. |
| | Bmi1 | NM_001285971.1 | Sense: TCATTGATGCCACAACCATT<br>Anti-sense: TGAAAAGCCCCGGAACTAAT | 189 | 60° C. |
| GI tract-related genes | Muc2 | NC_010444.3 | Sense: GGCTGCTCATTGAGAGGAGT<br>Anti-sense: ATGTTCCCGAACTCCAAGG | 249 | 60° C. |
| | CDX2 | NC_010453.4 | Sense: AGAACCCCCAGGTCTCTGTCTT<br>Anti-sense: CAGTCCGAAACACTCCCTCACA | 115 | 56° C. |
| Hepatic parenchymal cells related genes | AFP | NM_21431.1 | Sense: CGCGTTTCTGGTTGCTTACAC<br>Anti-sense: ACTTCTTGCTCTTGGCCTTGG | 609 | 60 |
| | Albumin | AY663543.1 | Sense: AGTCTGCCAAGCTGCTGATA<br>Anti-sense: AGCCTTGGGAAATCTCTGGC | 115 | 56 |
| Pancreatic endocrine- related genes | PDX-1 | NM_001141664.2 | Sense: AGTGATACTGGATTGGCGTTG<br>Anti-sense: TAGGGAGCCTTCCAATGTGT | 139 | 62 |
| | MAFA | NC_010446.4 | Sense: GCTTCAGCAAGGAGGAGGTC<br>Anti-sense: TCTCGCTCTCCAGAATGTGC | 120 | 62 |

What is claimed is:

1. A method of treating a subject with a disease or disorder of the pancreas, the method comprising contacting the subject's pancreas with a patch graft comprising:
   (a) a mixed population comprising mesenchymal and epithelial cells, wherein the epithelial cells are endodermal cells or stem cells capable of endodermal differentiation, wherein at least the mesenchymal cells or the epithelial cells are at an early lineage stage that is capable of expressing membrane-associated and/or secreted matrix metalloproteinases (MMPs), wherein said mixed population is supported in a first hydrogel having viscoelasticity from 0.1 to 200 Pa that allows migration of said mixed population towards and into the subject's pancreas and that allows for the expression of membrane-associated and/or secreted matrix MMPs from at least one of the cell types; and
   (b) a backing comprising a biocompatible, biodegradable material having a viscoelasticity sufficient to inhibit a migration of said mixed population in a direction away from the target tissue and through said backing, and
   allowing the cells contained in the patch graft to become incorporated into the pancreas.

2. The method of claim 1 in which the disease or disorder of the pancreas is diabetes mellitus, exocrine pancreatic insufficiency, pancreatitis, pancreatic cancer, sphincter of Oddi dysfunction, cystic fibrosis, pancreas divisum, annular pancreas, pancreatic trauma, or hemosuccus pancreaticus.

3. The method of claim 1, in which said backing further comprises a porous mesh infused with a second hydrogel.

4. The method of claim 1, in which the patch graft further comprises:
   (c) a third hydrogel overlaid on a serosal surface of said backing, the serosal surface being opposite to that in contact with said mixed population.

5. The method of claim 1 in which the first hydrogel comprises one or more hyaluronans.

6. The method of claim 3, in which the second hydrogel comprises one or more hyaluronans.

7. The method of claim 4, in which the third hydrogel comprises one or more hyaluronans.

8. The method of claim 1 in which said the first hydrogel comprises Kubota's Medium or other medium that supports stemness.

9. The method of claim 1 in which the mesenchymal cells comprise early lineage stage mesenchymal cells (ELSMCs).

10. The method of claim 9 in which said ELSMCs comprise one or more cells selected from the group consisting of angioblasts, precursors to endothelia, or precursors to stellate cells or mesenchymal stem cells (MSCs).

11. The method of claim 1 in which said epithelial cells further comprise epithelial stem cells.

12. The method of claim 11 in which said epithelial stem cells further comprise biliary tree stem cells (BTSCs).

13. The method of claim 1 in which said epithelial cells further comprise committed and/or mature epithelial cells.

14. The method of claim 13 in which said committed and/or mature epithelial cells further comprise mature parenchymal cells.

15. The method of claim 14 in which said mature parenchymal cells further comprise one or more of hepatocytes, cholangiocytes, and islet cells.

16. The method of claim 1 in which said mesenchymal cells and epithelial cells both further comprise stem cells.

17. The method of claim 1 in which said mixed population further comprises autologous and/or allogeneic cells.

18. The method of claim 1 in which one or more of said cells is genetically modified.

19. The method of claim 1 in which the backing further comprises a porous mesh, scaffold, or membrane.

20. The method of claim 1 in which the backing further comprises non-porous material.

21. The method of claim 20 in which the non-porous material is a material selected from the group consisting of silk, amnion, placenta, omentum, a synthetic textile, a derivative of the foregoing, or combinations thereof.

22. The method of claim 1 in which the backing has sufficient resilience to withstand mechanical forces, is able to be tethered to a target organ or tissue, and has sufficient flexibility to be tethered to locations with curvature.

23. The method of claim 1, wherein the first hydrogel has a viscoelasticity from 0.1 to 150 Pa.

24. The method of claim 1, wherein the first hydrogel has a viscoelasticity from 10 to 150 Pa.

25. The method of claim 3, wherein the second hydrogel has a viscoelasticity from 200 to 800 Pa.

26. The method of claim 4, wherein the third hydrogel overlaid on the serosal surface of said backing has viscoelasticity from 200 to 500 Pa.

\* \* \* \* \*